United States Patent
Sommer et al.

(10) Patent No.: US 9,296,739 B2
(45) Date of Patent: *Mar. 29, 2016

(54) FORMULATIONS AND PHARMACOKINETICS OF DEUTERATED BENZOQUINOLINE INHIBITORS OF VESICULAR MONOAMINE TRANSPORTER 2

(71) Applicant: Auspex Pharmaceuticals, Inc., La Jolla, CA (US)

(72) Inventors: Andreas Sommer, Carlsbad, CA (US); Chengzhi Zhang, San Diego, CA (US); John Carter, Vista, CA (US); John Arthur, Vista, CA (US); Margaret Bradbury, Vista, CA (US); Thomas Gant, Carlsbad, CA (US); Manouchehr Shahbaz, San Diego, CA (US)

(73) Assignee: Auspex Pharmaceuticals, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/245,024

(22) Filed: Apr. 4, 2014

(65) Prior Publication Data

US 2014/0341994 A1    Nov. 20, 2014

Related U.S. Application Data

(63) Continuation of application No. 14/030,322, filed on Sep. 18, 2013.

(60) Provisional application No. 61/702,586, filed on Sep. 18, 2012.

(51) Int. Cl.
| | |
|---|---|
| *C07D 471/04* | (2006.01) |
| *C07D 401/14* | (2006.01) |
| *A61K 45/06* | (2006.01) |
| *A61K 31/501* | (2006.01) |
| *C07D 455/06* | (2006.01) |
| *A61K 31/4745* | (2006.01) |
| *A61K 9/00* | (2006.01) |
| *A61K 9/16* | (2006.01) |
| *A61K 9/20* | (2006.01) |
| *A61K 9/28* | (2006.01) |
| *A61K 9/48* | (2006.01) |
| *A61K 9/50* | (2006.01) |
| *A61K 31/473* | (2006.01) |

(52) U.S. Cl.
CPC ............ *C07D 455/06* (2013.01); *A61K 9/0065* (2013.01); *A61K 9/1676* (2013.01); *A61K 9/2018* (2013.01); *A61K 9/2031* (2013.01); *A61K 9/2054* (2013.01); *A61K 9/2072* (2013.01); *A61K 9/2077* (2013.01); *A61K 9/2095* (2013.01); *A61K 9/288* (2013.01); *A61K 9/2846* (2013.01); *A61K 9/2866* (2013.01); *A61K 9/4808* (2013.01); *A61K 9/5047* (2013.01); *A61K 9/5073* (2013.01); *A61K 9/5078* (2013.01); *A61K 9/5084* (2013.01); *A61K 31/473* (2013.01); *A61K 31/4745* (2013.01); *A61K 45/06* (2013.01); *C07B 2200/05* (2013.01)

(58) Field of Classification Search
CPC . A61K 2300/00; A61K 45/06; A61K 31/451; A61K 31/501; C07D 471/04; C07D 401/04; C07D 401/14
USPC .................. 514/255.05, 210.21; 424/474
See application file for complete search history.

(56) References Cited

U.S. PATENT DOCUMENTS

| | | | |
|---|---|---|---|
| 2,830,993 A | 4/1958 | Brossi et al. | |
| 2,843,591 A | 7/1958 | Brossi et al. | |
| 3,045,021 A | 7/1962 | Brossi | |
| 4,193,998 A | 3/1980 | Szantay et al. | |
| 4,316,897 A | 2/1982 | Lotz | |
| 5,451,409 A * | 9/1995 | Rencher et al. | 424/468 |
| 6,221,335 B1 | 4/2001 | Foster | |
| 6,287,599 B1 | 9/2001 | Burnside et al. | |
| 6,440,710 B1 | 8/2002 | Keinan et al. | |
| 6,488,962 B1 | 12/2002 | Berner et al. | |
| 6,603,008 B1 | 8/2003 | Ando et al. | |
| 7,517,990 B2 | 4/2009 | Ito et al. | |
| 7,897,768 B2 | 3/2011 | Rishel et al. | |
| 7,976,870 B2 | 7/2011 | Berner et al. | |
| 8,008,500 B2 | 8/2011 | Rishel et al. | |
| 8,053,578 B2 | 11/2011 | Rishel et al. | |

(Continued)

FOREIGN PATENT DOCUMENTS

| | | |
|---|---|---|
| CN | 102936246 A | 2/2013 |
| EP | 1716145 B1 | 8/2008 |

(Continued)

OTHER PUBLICATIONS

Bauer, LA et. al.; 0Influence of long-term infusions on lidocaine kinetics, Clin. Pharmacol. Ther. 1982, 433-7.

(Continued)

*Primary Examiner* — Frederick Krass
*Assistant Examiner* — Tracy Liu
(74) *Attorney, Agent, or Firm* — Dennis A. Bennett; Cynthia Hathaway

(57) ABSTRACT

The present invention relates to new pharmaceutical compositions comprising benzoquinoline compounds, and methods to inhibit vesicular monoamine transporter 2 (VMAT2) activity in a subject for the treatment of chronic hyperkinetic movement disorders.

27 Claims, 12 Drawing Sheets

(56) References Cited

U.S. PATENT DOCUMENTS

| | | |
|---|---|---|
| 8,524,733 B2 | 9/2013 | Gant et al. |
| 2002/0013372 A1 | 1/2002 | Ekins |
| 2005/0064034 A1 | 3/2005 | Li et al. |
| 2007/0197695 A1 | 8/2007 | Potyen et al. |
| 2008/0033011 A1 | 2/2008 | Tung |
| 2008/0050312 A1 | 2/2008 | Kung et al. |
| 2008/0167337 A1 | 7/2008 | Gano |
| 2008/0212839 A1 | 9/2008 | Salla et al. |
| 2008/0299204 A1* | 12/2008 | Nangia et al. .............. 424/489 |
| 2009/0018191 A1 | 1/2009 | Alken et al. |
| 2009/0142265 A1 | 6/2009 | Rishel et al. |
| 2009/0297599 A1* | 12/2009 | Viragh et al. .............. 424/465 |
| 2010/0055133 A1* | 3/2010 | Duffield et al. ............ 424/239.1 |
| 2010/0113496 A1 | 5/2010 | Gant et al. |
| 2010/0130408 A1 | 5/2010 | Kohjima et al. |
| 2010/0189698 A1 | 7/2010 | Willis |
| 2010/0204258 A1 | 8/2010 | Harris et al. |
| 2011/0053866 A1 | 3/2011 | Duffield et al. |
| 2011/0118300 A1 | 5/2011 | Harris et al. |
| 2011/0182818 A1 | 7/2011 | Fallon |
| 2011/0206782 A1 | 8/2011 | Zhang |
| 2012/0003330 A1 | 1/2012 | Gant et al. |
| 2012/0053159 A1 | 3/2012 | Muller et al. |
| 2012/0077839 A1 | 3/2012 | Gano |
| 2013/0116215 A1 | 5/2013 | Coma et al. |
| 2013/0197067 A1 | 8/2013 | Anderson |
| 2013/0197227 A1 | 8/2013 | Min et al. |
| 2013/0296360 A1 | 11/2013 | Gant et al. |
| 2014/0206712 A1 | 7/2014 | Gant et al. |
| 2014/0206713 A1 | 7/2014 | Gant et al. |
| 2014/0336386 A1 | 11/2014 | Gant et al. |
| 2014/0350044 A1 | 11/2014 | Gant et al. |
| 2015/0004231 A1 | 1/2015 | Gant et al. |
| 2015/0080426 A1 | 3/2015 | Gant et al. |
| 2015/0080427 A1 | 3/2015 | Gant et al. |
| 2015/0152099 A1 | 6/2015 | Zhang |

FOREIGN PATENT DOCUMENTS

| | | |
|---|---|---|
| EP | 02326643 B1 | 5/2013 |
| WO | WO9526325 A2 | 10/1995 |
| WO | WO0008020 A2 | 2/2000 |
| WO | WO2005051389 | 6/2005 |
| WO | WO2005077946 A1 | 8/2005 |
| WO | WO2006053067 A2 | 5/2006 |
| WO | WO2006078846 A1 | 7/2006 |
| WO | WO2007130365 A2 | 11/2007 |
| WO | WO2008058261 A1 | 5/2008 |
| WO | WO2008064274 A1 | 5/2008 |
| WO | WO2008112278 A2 | 9/2008 |
| WO | WO2008154243 A1 | 12/2008 |
| WO | WO2009003226 A1 | 1/2009 |
| WO | WO2009070552 A1 | 6/2009 |
| WO | WO2009124357 A1 | 10/2009 |
| WO | WO2010018408 A2 | 2/2010 |
| WO | WO2010018408 A3 | 2/2010 |
| WO | WO2010044981 A2 | 4/2010 |
| WO | WO 2010044981 A2 * | 4/2010 |
| WO | WO2010044981 A3 | 4/2010 |
| WO | WO2011019956 A2 | 2/2011 |
| WO | WO2011106248 A2 | 9/2011 |
| WO | WO2011106248 A3 | 9/2011 |
| WO | WO2011153157 A2 | 12/2011 |
| WO | WO2011153157 A3 | 4/2012 |
| WO | WO2012079022 A1 | 6/2012 |
| WO | WO2012081031 A1 | 6/2012 |
| WO | WO2013142816 A1 | 9/2013 |
| WO | WO2014047167 A1 | 3/2014 |
| WO | WO2014047167 A3 | 3/2014 |
| WO | WO2014120654 A1 | 8/2014 |
| WO | WO2014120654 A3 | 8/2014 |
| WO | WO2015048370 A1 | 4/2015 |
| WO | WO2015048370 A3 | 4/2015 |
| WO | WO2015077520 A1 | 5/2015 |
| WO | WO2015077520 A3 | 5/2015 |
| WO | WO2015077521 A1 | 5/2015 |
| WO | WO2015077521 A3 | 5/2015 |
| WO | WO2015084622 A1 | 6/2015 |
| WO | WO2015084622 A3 | 6/2015 |
| WO | WO2015112707 A1 | 7/2015 |
| WO | WO2015112707 A3 | 7/2015 |

OTHER PUBLICATIONS

Borgstrom, L et al.; Comparative Pharmacokinetics of Unlabeled and Deuterium-Labeled Terbutaline: Demonstration of a Small Isotope Effect, J Pharm Sci, 1988, 77(11), 952-4.

Browne, T.R.; Chapter 2. Isotope Effect: Implications for Pharmaceutical Investigations, Pharm Lib 13, 1997.

Browne, T.R. et al.; Pharmacokinetic Equivalence of Stable-Isotope-Labeled and Unlabeled Drugs. Phenobarbital in Man, J Clin Pharmacol, 1982, 22, 309-315.

Burm, AGL et al.; Pharmacokinetics of Lidocaine and bupivacaine and stable isotope-labeled analogs: a study in healthy volunteers, Biopharmaceutics and Drug Disposition, 1988, 9, 85-95.

Elison, C et al.;Effect of Deuteration of N-CH$_{3}$ Group on Potency and Enzymatic N-Demethylation of Morphine, Science, 1961, 134(3485), 1078-9.

Farmer, PB, et al.; Synthesis, Metabolism, and Antitumor Activity of Deuterated Analogues of 1-(2-Choloroethyl)-3-cyclohexyl-1-nitrosourea, Journal of Medicinal Chemistry, 1978, vol. 21, No. 6, 514-20.

Fisher, MB, et al.; The complexities inherent in attempts to decrease drug clearance by blocking sites of CYP-mediated metabolism, Curr Opin Drug Discov Develop; 2006, 9(1), 101-9.

Foster, AB; Deuterium Isotope Effects in Studies of Drug Metabolism, Trends in Pharmacological Sciences, Dec. 1984, 524-7.

Helfenbein, J et al.; Isotopic Effect Study of Propofol Deuteration on the Metabolism, Activity, and Toxicity of the Anesthetic, J. Med. Chem. 2002, 45, 5806-5808.

Kushner, DJ et al.; Pharmacological uses and perspectives of heavy water and deuterated compounds, Can J Phys Pharm 1999, 77, 79-88.

Lee, H et al.; Deuterium Magic Angle Spinning Studies of Substrates Bound to Cytochrome P450, Biochemistry 1999, 38, 10808-10813.

Mamada, K et al.; Pharmacokinetic Equivalence of Deuterium-Labeled and Unlabeled Phenytoin, Drug Metabolism and Disposition, 1986, 14(4), 509-11.

Nelson, SD et al.; The Use of Deuterium Isotope Effect to Probe the Active Site Properties, Mechanism of Cytochrome P450-catalyzed Reactions, and Mechanisms of Metabolically Dependent Toxicity, Drug metabolism and disposition 31:1481-1498, 2003.

Nelson, SD et al.; Primary and B-Secondary Deuterium Isotope Effects in N-Deethylation Reactions, Journal of Medicinal Chemistry, 1975, vol. 18, No. 11.

Pohl, LR et al.; Determination of toxic Pathways of Metabolism by Deuterium Substitution, Drug Metabolism Rev 1985, 1335.

Rampe, D et al.; Deuterated Analogs of verapamil and nifedipine. Synthesis and biological activity, Eur J Med Chem (1993) 28, 259-263.

Toronto Research Chemicals, Inc., Tetrabenazine-d7, http://www.trc-canada.com/details.php?CatNumber=T284002. Downloaded 2009.

DaSilva, JN et al., Synthesis of [11C]Tetrabenazine, a Vesicular Monoamine Uptake Inhibitor, for PET Imaging Studies, Appl. Radiat. Isot. vol. 44, No. 4, pp. 673-676, 1993.

Kilbourn, MR et al., Absolute Configuration of (+)-a-Dihydrotetrabenazine, an Active Metabolite of Tetrabenazine, CHIRALITY 9:59-62 1997.

Mehvar, R et al., pharmacokinetics of tetrabenazine and its major metabolite in man and rat Bioavailability and Dose Dependency Studies, Drug Met Disp. 1987, 15(2), 250-255.

Popp, FD et al., Synthesis of potential antineoplastic agents XXVI: 1,3,4,6,7,11b-hexahydro-9,10-dimethoxy-2H-benzo[a]2-quinolizinone derivatives, Journal of Pharmaceutical Sciences, 1978, 67(6), 871-873.

(56) References Cited

OTHER PUBLICATIONS

Roberts, MS et al., The Pharmacokinetics of Tetrabenazine and its Hydroxy Metabolite in Patients Treated for Involuntary Movement Disorders, Eur J Clin Pharmacol (1986) 29: 703-708.
Schwartz, DE et al., Metabolic studies of tetrabenazine, a psychotropic drug in animals and man, Biochemical Pharmacology, 1966, 15, 645-655.
Zheng, G et al., Vesicular Monoamine Transporter 2: Role as a Novel Target for Drug Development, The AAPS Journal 2006; 8 (4) Article 78.
Paleacu et al., Tetrabenazine Treatment in Movement Disorders, Clin. Neuropharmacol., 2004, 27(5), 230-233.
Baillie, Thomas, The use of stable isotopes in pharmaceutical research, Pharmacological Reviews, 1981, 33(2), 81-132.
Browne, Thomas; Stable isotope techniques in early drug development: an economic evaluation, J. Clin. Pharmacol., 1998, 38, 213-220.
Cherrah et al.; Study of deuterium isotope effects on protein binding by gas chromatography/mass spectrometry. caffeine and deuterated isomers, Biomedical and Environmental Mass Spectrometry, 1987, 14, 653-657.
Dyck et al.; Effects of deuterium substitution on the catabolism of beta-phenethylamine: an in vivo study', J. Neurochem., 1986, 46(2), 399-404.
Gouyette, Alain; Use of deuterium-labelled elliptinium and its use in metabolic studies, Biomedical and Environmental Mass Spectrometry, 1988, 15, 243-247.
Haskins, N.J.; The application of stable isotopes in biomedical research, Biomedical Mass Spectrometry, 1982, 9(7), 269-277.
Honma et al.; The metabolism of roxatidine acetate hydrochloride, Drug Metabolism and Disposition, 1987, 15(4), 551-559.
Pieiaszek et al.; Moricizine bioavailability via simultaneous, dual, stable isotope administration: bioequivalence implications, J. Clin. Pharmacol., 1999, 39, 817-825.
Tonn et al.; Simultaneous analysis of diphenylhydramine and a stable isotope analog (2H10) diphenylhydramine using capillary gas chromatography with mass selective detection in biological fluids from chronically instrumented pregnant ewes, Biomedical Mass Spectrometry, 1993, 22, 633-642.
Wolen et al.; The application of stable isotopes to studies of drug bioavailibility and bioequivalence, J. Clin. Pharmacol., 1986, 26, 419-424.
Gant et al., Benzoquinoline Inhibitors of Vesicular Monoamine Transporter 2, WO 2010044981 International Preliminary Report on Patentability, Auspex Pharmaceuticals, Inc. Apr. 22, 2010.
Gant et al., Benzoquinoline Inhibitors of VMAT2, WO 2011106248 International Preliminary Report on Patentability, Auspex Pharmaceuticals, Inc., Sep. 1, 2011.
Foster, A.B., Deuterium Isotope Effects in the Metabolism of Drugs and Xenobiotics: Implications for Drug Design, Adv. Drug Res., Academic Press, London, GB, vol. 14, Jan. 1, 1985, pp. 1-40.
Jindal et al., Mass Spectrometric Determination of Tetrabenazine Using a Stable Isotope-labeled Analogue as an Internal Standard, Jindal et al., J. Chromatography, 1989, 493, 392-97.
cis (2,3)—Dihydro Tetrabenazine-d6, Chemical Book, Jan. 1, 2009.
Buteau K. C., Deuterated Drugs: Unexpectedly Nonobvious, Buteau K. C.,J. High Tech. L., 2009, pp. 22-74.
A Study of the Effectiveness and safety of Tetrabenazine MR in Pediatric Subjects With Tourette's Syndrome (TBZ-MR), https://clinicaltrials.gov/ct2/show/NCT01133353?term=tetrabenazine &rank=3, Downloaded Feb. 16, 2015.
Yao et al., Preparation and evaluation of tetrabenazine enantiomers and all eight stereoisomers of dihydrotetrabenazine as VMAT2 inhibitors, Eur. J. Med. Chem, 2011, 46, 1841-1848.
Goswami et al., Fluoroalkyl derivatives of dihydrotetrabenazine as positron emission tomography imaging agents targeting vesicular monoamine transporters, Nucl. Med. Biol., 2006, 33, 685-694.
Abrahamsson et al., Absorption, Gastrointestinal Transit, and Tablet Erosion of Felodipine Extended-Release (ER) Tablets, Pharmaceutical Rsearch, 1993, 10(5) 709-714.
Wingstrand et al., Bioavailability from felodipine extended-release tablets with different dissolution properties, Int. J. Pharmaceutics, 1990, 60, 151-156.
Lundbeck, Inc., Xenazine Prescibing Information, 2008.
Duffield et al., Pharmaceutical Compositions, WO 2010/018408—International Preliminary Report on Patentability, Biovail Laboratories International, Feb. 18, 2010.
Gant of al., Formulations pharmacokinetics of deuterated benzoquinoline inhibitors of vesicular monoamine transporter 2, Auspex Pharmaceuticals, Inc., WO2014047167A1, International Preliminary Report on Patentability, Received Mar. 27, 2014.
Gant et al., Formulations pharmacokinetics of deuterated benzoquinoline inhibitors of vesicular monoamine transporter 2, Auspex Pharmaceuticals, Inc., US20140336386A1, Non-Final Rejection, Nov. 28, 2014.
Kenny C et al., Tetrabenazine in the treatment of hyperkinetic movement disorders, Informa Healthcare, 2006, vol. 6, No. 1 ,pp. 7-17.
Gant et al., Benzoquinoline Inhibitors of Vesicular Monoamine Transporter 2, Auspex Pharmaceuticals, Inc., US8524733B2, Non Final Rejection, Apr. 10, 2012.
Gant et al., Benzoquinoline Inhibitors of Vesicular Monoamine Transporter 2, Auspex Pharmaceuticals, Inc., US8524733B2, Final Rejection, Nov. 5, 2012.
Gant et al., Benzoquinoline Inhibitors of Vesicular Monoamine Transporter 2, Auspex Pharmaceuticals, Inc., US8524733B2, Applicant Initiated Interview Summary, Apr. 24, 2013.
Gant et al., Benzoquinoline Inhibitors of Vesicular Monoamine Transporter 2, Auspex Pharmaceuticals, Inc., US8524733B2, Examiner initiated interview summary, Jun. 28, 2013.
Gant et al., Benzoquinoline Inhibitors of Vesicular Monoamine Transporter 2, Auspex Pharmaceuticals, Inc., US8524733B2, Notice of Allowance and Fees Due, Jun. 28, 2013.
Gant et al., Benzoquinoline Inhibitors of Vesicular Monoamine Transporter 2, Auspex Pharmaceuticals, Inc., US 20130296360 A1, Non-Final Rejection, Sep. 8, 2013.
Gant et al., Benzoquinoline Inhibitors of Vesicular Monoamine Transporter 2, Auspex Pharmaceuticals, Inc., US 20130296360 A1, Examiner initiated interview summary, Apr. 16, 2014.
Gant et al., Benzoquinoline Inhibitors of Vesicular Monoamine Transporter 2, Auspex Pharmaceuticals, Inc., US 20130296360 A1, Final Rejection, Apr. 16, 2014.
Gant et al., Benzoquinoline Inhibitors of Vesicular Monoamine Transporter 2, Auspex Pharmaceuticals, Inc., US 20140206712 A1, Non-Final Rejection, Dec. 3, 2014.
Gant et al., Benzoquinoline Inhibitors of Vesicular Monoamine Transporter 2, Auspex Pharmaceuticals, Inc., US 20140206712 A1, Examiner initiated interview summary, Jan. 23, 2015.
Gant et al., Benzoquinoline Inhibitors of Vesicular Monoamine Transporter 2, Auspex Pharmaceuticals, Inc., US 20140206712 A1, Final Rejection, Jan. 23, 2015.
Gant et al., Benzoquinoline Inhibitors of Vesicular Monoamine Transporter 2, Auspex Pharmaceuticals, Inc., US 20140206713 A1, Non-Final Rejection, Apr. 30, 2014.
Gant et al., Benzoquinoline Inhibitors of Vesicular Monoamine Transporter 2, Auspex Pharmaceuticals, Inc., US 20140206713 A1, Final Rejection, Sep. 8, 2014.
Gant et al., Benzoquinoline Inhibitors of Vesicular Monoamine Transporter 2, Auspex Pharmaceuticals, Inc., US 20140206713 A1, Notice of Allowance, Dec. 16, 2014.
Gant et al., Benzoquinoline Inhibitors of Vesicular Monoamine Transporter 2, Auspex Pharmaceuticals, Inc., US 20140350044 A1, Non-Final Rejection, Sep. 15, 2014.
Gant et al., Benzoquinoline Inhibitors of Vesicular Monoamine Transporter 2, Auspex Pharmaceuticals, Inc., US 20140350044 A1, Examiner initiated interview summary, Jan. 13, 2015.
Gant et al., Benzoquinoline Inhibitors of Vesicular Monoamine Transporter 2, Auspex Pharmaceuticals, Inc., US 20140350044 A1, Notice of Allowance, Jan. 13, 2015.
Gant et al., Benzoquinoline Inhibitors of VMAT2, Auspex Pharmaceuticals, Inc., WO2011153157A2, International Preliminary Report on Patentability, publication date Dec. 4, 2012.

(56) References Cited

OTHER PUBLICATIONS

Gant et al., Benzoquinoline Inhibitors of VMAT2, Auspex Pharmaceuticals, Inc., US20120003330 A1, Non-Final Rejection, Jan. 16, 2014.

Gant et al., Benzoquinoline Inhibitors of VMAT2, Auspex Pharmaceuticals, Inc., US20150080426 A1, Examiner initiated interview summary, Feb. 6, 2015.

Gant et al., Benzoquinoline Inhibitors of VMAT2, Auspex Pharmaceuticals, Inc., US20150080426 A1, Non-Final Rejection, Feb. 6, 2015.

Lee et al., In Vitro and in Vivo Studies of Benzisoquinoline Ligands for the Brain Synaptic Vesicle Monoamine Transporter, Journal Med. Chem., 1996, 39, 191-96.

Kilbourn et al., Binding of alpha-Dihydrotetrabenazine to the Vesicular Monoamine Transporter is Stereospecific, Eur. J. Pharmacol., 1995, 278, 249-52.

Scifinder Database Search, Dihydrotetrabenazine Scifinder Structure Search, Search Performed on May 22, 2010.

Rishel et al., Asymmetric synthesis of Tetrabenazine and Dihydrotetrabenazine, J. Org. Chem., 2009, 74, 4001-04.

Sommer et al., Benzoquinolone Inhibitors of VMAT2, Auspex Pharmaceuticals, Inc., WO2014120654A1, International Preliminary Report on Patentability, publication date Aug. 4, 2015.

PUBCHEM, Compound Summary for AGN-PC-01VNZU, https://pubchem.ncbi.nlm.nfttgov/compoundll84l2o75> entire document, created Jan. 16, 2012.

PUBCHEM, Compound Summary for 54765059, https-J/pubchem.ncbi.nlm.nih.gov/compound/54765059>. entire document, created Jan. 16, 2012.

Nutt et all., Evidence-based guidelines for management of attention-deficit/hyperactivity disorder in adolescents in transition to adult services and in adults: recommendations from the British Association for Psychopharmacology, J Psychopharmacol. Jan. 2007;21(1):10-41. Epub Nov. 8, 2006.

Gant et al., Formulations pharmacokinetics of deuterated benzoquinoline inhibitors of vesicular monoamine transporter 2, Auspex Pharmaceuticals, Inc., US 20150004231 A1, Non-Final Rejection, Oct. 29, 2014.

Gant et al., Formulations pharmacokinetics of deuterated benzoquinoline inhibitors of vesicular monoamine transporter 2, Auspex Pharmaceuticals, Inc., US 20150004231 A1, Notice of Allowance.And Fees Due, Apr. 15, 2015.

Gant et al., Benzoquinoline inhibitors of vesicular monoamine transporter 2, Auspex Pharmaceuticals,.Inc., US 20150080427A1, Non-Final Rejection, Dec. 29, 2014.

Gant et al., Benzoquinoline inhibitors of vesicular monoamine transporter 2, Auspex Pharmaceuticals, Inc., US 20150080427A1, Final Rejection, Aug. 11, 2015.

\* cited by examiner

Tetrabenazine Tablet Manufacturing Flow Chart

Single dose mean plasma concentrations of total (α+β)-HTBZ
From 3 dose levels of d₆-tetrabenazine ER and one dose level of tetrabenazine

Steady state plasma concentrations of total (α+β)-HTBZ
From 3 dose levels of $d_6$-tetrabenazine ER and one dose level of tetrabenazine Data from CTP-07 Part 2 Interim Analysis Thermogravimetric analysis (TGA) profile of $d_6$-tetrabenazine, Form I Differential scanning calorimetry (DSC) profile of $d_6$-tetrabenazine, Form I Powder X-ray diffraction (pXRD) profile of $d_6$-tetrabenazine, Form I Thermogravimetric analysis (TGA) profile of $d_6$-tetrabenazine, Form II Differential scanning calorimetry (DSC) profile of d$_6$-tetrabenazine, Form II Powder X-ray diffraction (pXRD) profile of d₆-tetrabenazine, Form II

FORMULATIONS AND PHARMACOKINETICS OF DEUTERATED BENZOQUINOLINE INHIBITORS OF VESICULAR MONOAMINE TRANSPORTER 2

This application is a continuation of U.S. patent application Ser. No. 14/030,322, filed Sep. 18, 2013, which claims the benefit of priority of U.S. provisional application No. 61/702,586, filed Sep. 18, 2012, the disclosures of which are hereby incorporated by reference as if written herein in their entireties.

Disclosed herein are new pharmaceutical compositions comprising benzoquinoline compounds, methods to inhibit vesicular monoamine transporter 2 (VMAT2) activity in a subject, and methods for the treatment of chronic hyperkinetic movement disorders.

Tetrabenazine ((+/−)-cis-tetrabenazine, Nitoman®, Xenazine®, Ro 1-9569), is a racemic mixture of (3R,11bR)-1,3,4,6,7,11b-Hexahydro-9,10-dimethoxy-3-(2-methylpropyl)-2H-benzo[a]quinolizin-2-one, and (3S,11bS)-1,3,4,6,7,11b-hexahydro-9,10-dimethoxy-3-(2-methylpropyl)-2H-benzo[a]quinolizin-2-one. Tetrabenazine is a vesicular monoamine transporter 2 (VMAT2) inhibitor. Tetrabenazine is commonly prescribed for the treatment of chorea associated with Huntington's disease (Savani et al., *Neurology* 2007, 68(10), 797; and Kenney et al., *Expert Review of Neurotherapeutics* 2006, 6(1), 7-17).

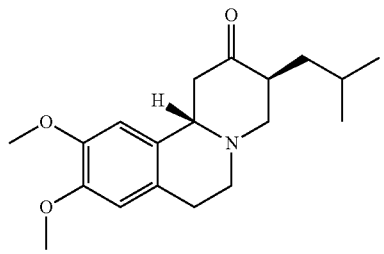 [SMILES: COc1cc2c(cc1OC)[C@@H]1CC(=O)[C@@H](CC(C)C)CN1CC2]

(3S,11bS)-1,3,4,6,7,11b-hexahydro-9,10-dimethoxy-3-(2-methylpropyl)-2H-benzo[a]quinolizin-2-one

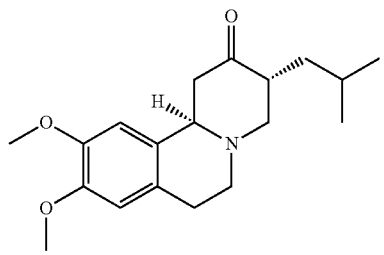 [SMILES: COc1cc2c(cc1OC)[C@H]1CC(=O)[C@H](CC(C)C)CN1CC2]

(3R,11bR)-1,3,4,6,7,11b-hexahydro-9,10-dimethoxy-3-(2-methylpropyl)-2H-benzo[a]quinolizin-2-one $d_6$-Tetrabenazine ((+/−)-cis-$d_6$-tetrabenazine) is a racemic mixture of (3R,11bR)-1,3,4,6,7,11b-hexahydro-9,10-di(methoxy-$d_3$)-3-(2-methylpropyl)-2H-benzo[a]quinolizin-2-one and (3S,11bS)-1,3,4,6,7,11b-hexahydro-9,10-di(methoxy-$d_3$)-3-(2-methylpropyl)-2H-benzo[a]quinolizin-2-one. $d_6$-Tetrabenazine is a selectively deuterium-substituted, stable, non-radioactive isotopic form of tetrabenazine in which the six hydrogen atoms on the two O-linked methyl groups have been replaced with deuterium atoms (i.e. —OCD$_3$ rather than —OCH$_3$ moieties).

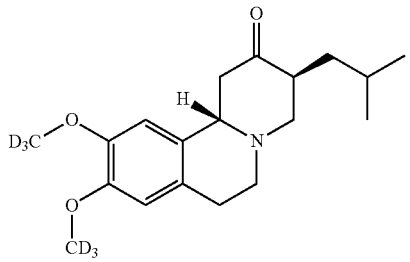 [SMILES: [2H]C([2H])([2H])Oc1cc2c(cc1OC([2H])([2H])[2H])[C@@H]1CC(=O)[C@@H](CC(C)C)CN1CC2]

(3S,11bS)-1,3,4,6,7,11b-hexahydro-9,10-di(methoxy-$d_3$)-3-(2-methylpropyl)-2H-benzo[a]quinolizin-2-one

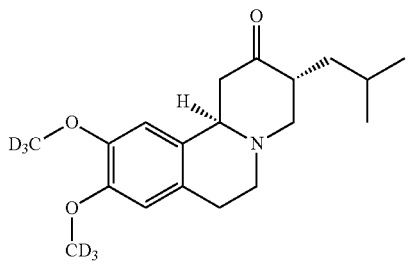 [SMILES: [2H]C([2H])([2H])Oc1cc2c(cc1OC([2H])([2H])[2H])[C@H]1CC(=O)[C@H](CC(C)C)CN1CC2]

(3R,11bR)-1,3,4,6,7,11b-hexahydro-9,10-di(methoxy-$d_3$)-3-(2-methylpropyl)-2H-benzo[a]quinolizin-2-one Tetrabenazine and its major metabolites alpha-dihydrotetrabenazine (α-HTBZ) and beta-dihydrotetrabenazine (β-HTBZ) are selective and potent inhibitors of the VMAT2. Scherman et al., *Mol. Pharmacol.* 1988, 33(1):72-7. In humans, extensive hepatic metabolism of tetrabenazine to α-HTBZ and β-HTBZ by carbonyl reductase results in plasma concentrations of tetrabenazine that are very low and are often below the limit of detection. Thus, α-HTBZ and β-HTBZ are thought to confer the pharmacological and therapeutic activity of orally administered tetrabenazine in patients. In human plasma, α-HTBZ and β-HTBZ have half-lives of 7 hours and 5 hours, respectively (Xenazine® US Prescribing Information). Alpha(α)-HTBZ and β-HTBZ are each metabolized into pairs of mono-O-desmethyl metabolites (9-O-desmethyl-HTBZ and 10-O-desmethyl-HTBZ) which are, in turn, conjugated by sulfonation and/or glucuronidation for excretion. The 9-O-desmethyl-β-HTBZ metabolite, which is derived from β-HTBZ, is also a major circulating metabolite. CYP2D6 is primarily responsible for 0-demethylation of α-HTBZ and β-HTBZ in humans.

$d_6$-Tetrabenazine has been designed with the intent to improve the pharmacokinetic profile of active metabolites α-HTBZ and β-HTBZ. The CYP mediated cleavage of the carbon-deuterium bonds within the trideuterated methyl groups (CD$_3$) of $d_6$-tetrabenazine is slower than the cleavage of the carbon-hydrogen bonds in the methyl groups (CH$_3$) of tetrabenazine, an effect that selectively attenuated O-demethylation of deuterated α-HTBZ and β-HTBZ (d$_6$-α-HTBZ and d$_6$-β-HTBZ) in in vitro studies. An increase in the stability of deuterated α-HTBZ and β-HTBZ and a corresponding reduction of O-desmethyl metabolites have been demonstrated in in vitro metabolism assays. In contrast, the conversion of tetrabenazine to its HTBZ metabolites does not involve carbon-hydrogen bond cleavage and, as such, is not altered by the presence of deuterium in the molecule.

The spectrum of metabolites produced by d$_6$-tetrabenazine is expected to be similar to that in patients with reduced CYP2D6 metabolism who receive tetrabenazine. This is based on in vitro metabolism studies and a drug interaction study of tetrabenazine and paroxetine. In the drug interaction study, co-administration of tetrabenazine and paroxetine increased systemic exposure to the α-HTBZ and β-HTBZ metabolites by 3- to 9-fold, respectively, compared to tetrabenazine alone (Xenazine® U.S. prescribing information). In vitro studies have demonstrated that digestion of deuterated α-HTBZ and -β-HTBZ produced 69-87% less of the O-desmethyl metabolites compared to non-deuterated α-HTBZ and β-HTBZ. Administration of d$_6$-tetrabenazine to healthy volunteers led to an approximate 2-fold increase in systemic exposure to α-HTBZ and β-HTBZ and proportional reductions in O-desmethyl metabolites compared to tetrabenazine. The increased exposure to α-HTBZ and β-HTBZ resulting from deuteration was not as pronounced as when tetrabenazine was administered with a strong CYP2D6 inhibitor such as paroxetine. Therefore, the metabolite profile associated with d$_6$-tetrabenazine should be qualitatively similar to that observed in subjects with reduced CYP2D6 metabolism who receive tetrabenazine (e.g. patients on paroxetine) and no new metabolites are anticipated.

d$_6$-Tetrabenazine has been formulated as an extended release (ER) tablet. d$_6$-tetrabenazine ER is expected to provide a benefit to patients, through a combination of extended release and attenuated metabolism, by reducing peak-to-trough ratios and improving tolerability compared with tetrabenazine. Since the effect of deuteration is expected to be reduced in subjects with no functional CYP2D6 metabolism, e.g., poor metabolizers, it is likely that the inter-subject variability in the pharmacokinetics of α- and β-HTBZ will be lower for d$_6$-tetrabenazine than for tetrabenazine. Thus, deuteration has the potential reduce the impact of drug interactions and further improve the safety profile of d$_6$-tetrabenazine ER. Finally, the increased half-life resulting from deuteration in conjunction with the extended release provided by the formulation, also has the potential to reduce dose frequency and improve overall patient compliance as compared to the TID dosing regimen commonly used with tetrabenazine.

Novel pharmaceutical compositions have been discovered, together with methods of synthesizing and using the compositions, including methods for the treatment of VMAT2-mediated disorders in a patient by administering the compositions as disclosed herein.

Figure 1:
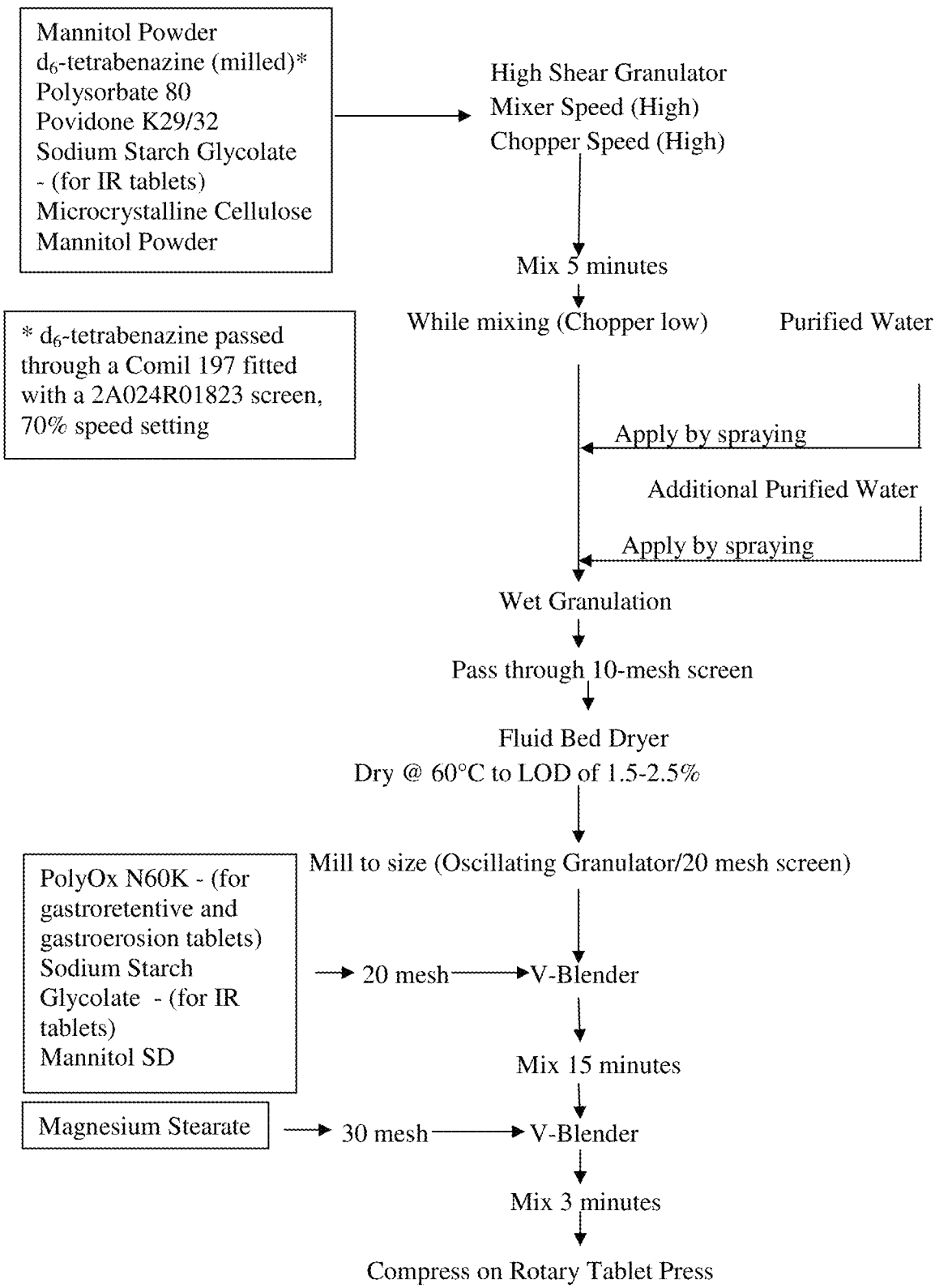
FIG. 1: Method of preparation of d$_6$-tetrabenazine extended release formulations and tetrabenazine extended release formulations.

In certain embodiments, disclosed herein is a pharmaceutical composition comprising a deuterated analogue of tetrabenazine which yields, when orally administered to a subject, at least one of the following:

an increase of the AUC of the total combined amount of deuterated dihydrotetrabenazine of at least 50% as compared to a pharmaceutical composition comprising an equivalent amount of non-deuterated tetrabenazine; or an increase in half-life of deuterated dihydrotetrabenazine of at least 50%;

as compared to a pharmaceutical composition comprising an equivalent amount of non-deuterated tetrabenazine.

In certain embodiments, the dihydrotetrabenazine is deuterated alpha-dihydrotetrabenazine, deuterated beta-dihydrotetrabenazine, or a combination of deuterated alpha-dihydrotetrabenazine and deuterated beta-dihydrotetrabenazine.

In certain embodiments, the deuterated analogue of tetrabenazine is selected from the group consisting of (3R,11bR)-1,3,4,6,7,11b-hexahydro-9,10-di(methoxy-d$_3$)-3-(2-methylpropyl)-2H-benzo[a]quinolizin-2-one, (3R,11bS)-1,3,4,6,7,11b-hexahydro-9,10-di(methoxy-d$_3$)-3-(2-methylpropyl)-2H-benzo[a]quinolizin-2-one, (3S,11bR)-1,3,4,6,7,11b-hexahydro-9,10-di(methoxy-d$_3$)-3-(2-methylpropyl)-2H-benzo[a]quinolizin-2-one, and (3S,11bS)-1,3,4,6,7,11b-hexahydro-9,10-di(methoxy-d$_3$)-3-(2-methylpropyl)-2H-benzo[a]quinolizin-2-one.

In certain embodiments, the deuterated analogue of tetrabenazine is d$_6$-tetrabenazine.

In certain embodiments, the deuterated analogue of tetrabenazine is (+/−)-trans-d$_6$-tetrabenazine.

In certain embodiments, the pharmaceutical composition yields an increase of the AUC of the total combined amount of deuterated alpha-dihydrotetrabenazine and deuterated beta-dihydrotetrabenazine of at least 100%; or an increase in half-life of the total combined amount of deuterated alpha-dihydrotetrabenazine and deuterated beta-dihydrotetrabenazine of at least 70%;

as compared to a pharmaceutical formulation comprising an equivalent amount of non-deuterated tetrabenazine.

In certain embodiments, the pharmaceutical composition yields an increase in half-life of the total combined amount of deuterated alpha-dihydrotetrabenazine and deuterated beta-dihydrotetrabenazine at least 100% as compared to a pharmaceutical composition comprising an equivalent amount of non-deuterated tetrabenazine.

In certain embodiments, the pharmaceutical composition yields a reduced AUC or $C_{max}$ of O-desmethyl metabolites of deuterated alpha-dihydrotetrabenazine and deuterated beta-dihydrotetrabenazine as compared to a pharmaceutical composition comprising an equivalent amount of non-deuterated tetrabenazine.

In certain embodiments, the AUC of 9-O-desmethyl metabolites of deuterated alpha-dihydrotetrabenazine and 9- and 10-O-desmethyl metabolites of deuterated beta-dihydrotetrabenazine is reduced by at least 25%.

In certain embodiments, the AUC of 9-O-desmethyl metabolites of deuterated alpha-dihydrotetrabenazine and 9- and 10-O-desmethyl metabolites of deuterated beta-dihydrotetrabenazine is reduced by at least 50%.

In certain embodiments, the AUC of 9-O-desmethyl metabolites of deuterated alpha-dihydrotetrabenazine and 9- and 10-O-desmethyl metabolites of deuterated beta-dihydrotetrabenazine is reduced by at least 70%.

In certain embodiments, the $C_{max}$ of O-desmethyl metabolites of deuterated alpha-dihydrotetrabenazine and deuterated beta-dihydrotetrabenazine is reduced by at least 25%.

In certain embodiments, the $C_{max}$ of O-desmethyl metabolites of deuterated alpha-dihydrotetrabenazine and deuterated beta-dihydrotetrabenazine is reduced by at least 40%.

In certain embodiments, the $C_{max}$ of O-desmethyl metabolites of deuterated alpha-dihydrotetrabenazine and deuterated beta-dihydrotetrabenazine is reduced by at least 55%.

In certain embodiments, the pharmaceutical composition yields a reduced ratio of $C_{max}$ to AUC of the total combined amount of deuterated alpha-dihydrotetrabenazine and deuterated beta-dihydrotetrabenazine as compared to a pharmaceutical composition comprising non-deuterated tetrabenazine.

In certain embodiments, the ratio of $C_{max}$ to AUC of the total combined amount of deuterated alpha-dihydrotetrabenazine and deuterated beta-dihydrotetrabenazine is reduced by at least 20% as compared to a pharmaceutical composition comprising non-deuterated tetrabenazine.

In certain embodiments, the ratio of $C_{max}$ to AUC of the total combined amount of deuterated alpha-dihydrotetrabenazine and deuterated beta-dihydrotetrabenazine is reduced by at least 40% as compared to a pharmaceutical composition comprising non-deuterated tetrabenazine.

In certain embodiments, the $C_{max}$ of the total combined amount of deuterated alpha-dihydrotetrabenazine and deuterated beta-dihydrotetrabenazine is reduced compared the $C_{max}$ of the total combined amount of alpha-dihydrotetrabenazine and beta-dihydrotetrabenazine at a dose of non-deuterated tetrabenazine that yields an equivalent AUC of total combined alpha-dihydrotetrabenazine and beta-dihydrotetrabenazine and total combined deuterated alpha-dihydrotetrabenazine and deuterated beta-dihydrotetrabenazine.

In certain embodiments, the $C_{max}$ of the total combined amount of deuterated alpha-dihydrotetrabenazine and deuterated beta-dihydrotetrabenazine is reduced by at least 25% as compared the $C_{max}$ of the total combined amount of alpha-dihydrotetrabenazine and beta-dihydrotetrabenazine at a dose of non-deuterated tetrabenazine that yields an equivalent AUC of total combined alpha-dihydrotetrabenazine and beta-dihydrotetrabenazine and total combined deuterated alpha-dihydrotetrabenazine and deuterated beta-dihydrotetrabenazine.

In certain embodiments, the pharmaceutical composition yields, when orally administered to a patient population, reduced interpatient variability in AUC of the total combined amount of alpha-dihydrotetrabenazine and beta-dihydrotetrabenazine as compared with non-deuterated tetrabenazine.

In certain embodiments, the pharmaceutical composition yields, when orally administered to a patient population, reduced interpatient variability in AUC of the total combined amount of alpha-dihydrotetrabenazine and beta-dihydrotetrabenazine between CYP2D6 poor metabolizers and CYP2D6 extensive and intermediate metabolizers as compared with non-deuterated tetrabenazine.

In certain embodiments, disclosed herein is an extended-release pharmaceutical formulation of $d_6$-tetrabenazine which permits a reduction in dose relative to non-deuterated tetrabenazine while maintaining at least equivalent AUC of total combined alpha-dihydrotetrabenazine and beta-dihydrotetrabenazine.

In certain embodiments, the reduction in dose is at least 30%.

In certain embodiments, the reduction in dose is at least 40%.

In certain embodiments, the extended-release pharmaceutical formulation yields an increase in half-life of total combined deuterated alpha-dihydrotetrabenazine and deuterated beta-dihydrotetrabenazine of at least 65% relative to the half-life of alpha-dihydrotetrabenazine and beta-dihydrotetrabenazine resulting from the administration of an equivalent formulation comprising non-deuterated tetrabenazine.

In certain embodiments, the extended-release pharmaceutical formulation yields a reduction in $C_{max}$ of total combined deuterated alpha-dihydrotetrabenazine and deuterated beta-dihydrotetrabenazine of at least 50% relative to the $C_{max}$ of alpha-dihydrotetrabenazine and beta-dihydrotetrabenazine resulting from the administration of an equivalent formulation comprising non-deuterated tetrabenazine.

In certain embodiments, the extended-release pharmaceutical formulation reduces the $C_{max}$ of total combined deuterated alpha-dihydrotetrabenazine and deuterated beta-dihydrotetrabenazine by at least 50% relative to the $C_{max}$ of alpha-dihydrotetrabenazine and beta-dihydrotetrabenazine achieved upon administration of an immediate-release formulation of tetrabenazine that yields at least equivalent AUC of total combined alpha-dihydrotetrabenazine and beta-dihydrotetrabenazine.

In certain embodiments, the $C_{max}$ of total combined deuterated alpha-dihydrotetrabenazine and deuterated beta-dihydrotetrabenazine is reduced by at least 60% relative to the $C_{max}$ of alpha-dihydrotetrabenazine and beta-dihydrotetrabenazine.

In certain embodiments, the $C_{max}$ of total combined deuterated alpha-dihydrotetrabenazine and deuterated beta-dihydrotetrabenazine is reduced by at least 70% relative to the $C_{max}$ of alpha-dihydrotetrabenazine and beta-dihydrotetrabenazine.

In certain embodiments, the $C_{max}$ of total combined deuterated alpha-dihydrotetrabenazine and deuterated beta-dihydrotetrabenazine is reduced by at least 75% relative to the $C_{max}$ of alpha-dihydrotetrabenazine and beta-dihydrotetrabenazine.

In certain embodiments, disclosed herein is an extended-release pharmaceutical formulation comprising, in a solid dosage form for oral delivery of between about 100 mg and about 1 g total weight:

between about 2 and about 18% of $d_6$-tetrabenazine;
between about 70% and about 96% of one or more diluents;
between about 1% and about 10% of a water-soluble binder; and
between about 0.5 and about 2% of a surfactant.

In certain embodiments, the total weight is about 350 mg and about 750 mg.

In certain embodiments, the diluent or diluents are chosen from mannitol, lactose, and microcrystalline cellulose;
the binder is a polyvinylpyrrolidone; and
the surfactant is a polysorbate.

In certain embodiments, the extended-release pharmaceutical formulation comprises between about 2.5% and about 11% of $d_6$-tetrabenazine.

In certain embodiments, the extended-release pharmaceutical formulation comprises:
between about 60% and about 70% mannitol or lactose;
between about 15% and about 25% microcrystalline cellulose
about 5% of polyvinylpyrrolidone K29/32; and
between about 1 and about 2% of Tween 80.

In certain embodiments, the extended-release pharmaceutical formulation comprises:
between about 4% and about 9% of a $d_6$-tetrabenazine;
between about 60% and about 70% mannitol or lactose;
between about 20% and about 25% microcrystalline cellulose
about 5% of polyvinylpyrrolidone K29/32; and
about 1.4% of Tween 80.

In certain embodiments, the extended-release pharmaceutical formulation comprises about 7.5 mg of $d_6$-tetrabenazine.

In certain embodiments, the extended-release pharmaceutical formulation comprises about 15 mg of $d_6$-tetrabenazine.

In certain embodiments, the extended-release pharmaceutical formulation comprises about 19.5 mg of $d_6$-tetrabenazine.

In certain embodiments, the extended-release pharmaceutical formulation comprises, in a solid dosage form for oral delivery of between about 100 mg and about 1 g total weight:
between about 70 and about 95% of a granulation of $d_6$-tetrabenazine, wherein the $d_6$-tetrabenazine comprises between about 1 and about 15% of the granulation;
between about 5% and about 15% of one or more diluents;
between about 5% and about 20% of sustained-release polymer; and
between about 0.5 and about 2% of a lubricant.

In certain embodiments, the extended-release pharmaceutical formulation comprises:
between about 5% and about 15% of one or more spray-dried mannitol or spray-dried lactose;
between about 5% and about 20% of sustained-release polymer; and between about 0.5 and about 2% of a magnesium stearate.

In certain embodiments, the sustained-release polymer is chosen from a polyvinyl acetate-polyvinylpyrrolidone mixture and a poly(ethylene oxide) polymer.

In certain embodiments, the sustained-release polymer is chosen from Kollidon® SR, POLYOX® N60K, and Carbopol®.

In certain embodiments, the sustained-release polymer is Kollidon® SR.

In certain embodiments, the sustained-release polymer is POLYOX® N60K.

In certain embodiments, the sustained-release polymer is Carbopol®.

In certain embodiments, the total weight is about 350 mg and about 700 mg.

In certain embodiments, the extended-release pharmaceutical formulation comprises from about 5 mg to about 30 mg of $d_6$-tetrabenazine.

In certain embodiments, the extended-release pharmaceutical formulation comprises about 6 mg of $d_6$-tetrabenazine.

In certain embodiments, the extended-release pharmaceutical formulation comprises about 12 mg of $d_6$-tetrabenazine.

In certain embodiments, the extended-release pharmaceutical formulation comprises about 18 mg of $d_6$-tetrabenazine.

In certain embodiments, the extended-release pharmaceutical formulation comprises about 7.5 mg $d_6$-tetrabenazine.

In certain embodiments, the extended-release pharmaceutical formulation comprises about 15 mg of $d_6$-tetrabenazine.

In certain embodiments, the extended-release pharmaceutical formulation comprises about 22.5 mg of $d_6$-tetrabenazine.

In certain embodiments, disclosed herein is a method of treating a VMAT2-mediated disease comprising the administration of an extended release pharmaceutical composition comprising 7.5 mg $d_6$-tetrabenazine wherein the $C_{max}$ of the total combined amount of deuterated dihydrotetrabenazine is about 21.37±6.78 ng/mL.

In certain embodiments, disclosed herein is an extended release pharmaceutical composition comprising 7.5 mg $d_6$-tetrabenazine for use in treatment of a VMAT2-mediated disease wherein the $C_{max}$ of the total combined amount of deuterated dihydrotetrabenazine is about 21.37±6.78 ng/mL.

In certain embodiments, disclosed herein is the use of an extended release pharmaceutical composition comprising 7.5 mg $d_6$-tetrabenazine for the manufacture of a medicament to treat a VMAT2-mediated disease wherein the $C_{max}$ of the total combined amount of deuterated dihydrotetrabenazine is about 21.37±6.78 ng/mL.

In certain embodiments, the $AUC_{inf}$ of the total combined amount of deuterated dihydrotetrabenazine is about 176.2±69.3 hr*ng/mL.

In certain embodiments, the $AUC_{(0-12)}$ of the total combined amount of deuterated dihydrotetrabenazine is about 110.2±32.1 hr*ng/mL.

In certain embodiments, the $T_{max}$ of the total combined amount of deuterated dihydrotetrabenazine is about 3.17±0.68 hr.

In certain embodiments, the $T_{half}$ of the total combined amount of deuterated dihydrotetrabenazine is about 7.18±1.35 hr.

In certain embodiments, disclosed herein is a method of treating a VMAT2-mediated disease comprising the administration of an extended release pharmaceutical composition comprising 15 mg $d_6$-tetrabenazine wherein the $C_{max}$ of the total combined amount of deuterated dihydrotetrabenazine is about 45.33±8.31 ng/mL.

In certain embodiments, disclosed herein is an extended release pharmaceutical composition comprising 15 mg $d_6$-tetrabenazine for use in treatment of a VMAT2-mediated disease wherein the $C_{max}$ of the total combined amount of deuterated dihydrotetrabenazine is about 45.33±8.31 ng/mL.

In certain embodiments, disclosed herein is the use of an extended release pharmaceutical composition comprising 15 mg $d_6$-tetrabenazine for the manufacture of a medicament to treat a VMAT2-mediated disease wherein the $C_{max}$ of the total combined amount of deuterated dihydrotetrabenazine is about 45.33±8.31 ng/mL.

In certain embodiments, the $AUC_{inf}$ of the total combined amount of deuterated dihydrotetrabenazine is about 408.3±147.2 hr*ng/mL.

In certain embodiments, the $AUC_{(0-12)}$ of the total combined amount of deuterated dihydrotetrabenazine is about 250.4±64.0 hr*ng/mL.

In certain embodiments, the $T_{max}$ of the total combined amount of deuterated dihydrotetrabenazine is about 3.21±0.45 hr.

In certain embodiments, the $T_{half}$ of the total combined amount of deuterated dihydrotetrabenazine is about 7.66±1.36 hr.

In certain embodiments, disclosed herein is a method of treating a VMAT2-mediated disease comprising the administration of an extended release pharmaceutical composition comprising 22.5 mg $d_6$-tetrabenazine wherein the $C_{max}$ of the total combined amount of deuterated dihydrotetrabenazine is about 67.49±16.72 ng/mL.

In certain embodiments, disclosed herein is an extended release pharmaceutical composition comprising 22.5 mg $d_6$-tetrabenazine for use in treatment of a VMAT2-mediated disease wherein the $C_{max}$ of the total combined amount of deuterated dihydrotetrabenazine is about 67.49±16.72 ng/mL.

In certain embodiments, disclosed herein is the use of an extended release pharmaceutical composition comprising 22.5 mg $d_6$-tetrabenazine for the manufacture of a medicament to treat a VMAT2-mediated disease wherein the $C_{max}$ of the total combined amount of deuterated dihydrotetrabenazine is about 67.49±16.72 ng/mL.

In certain embodiments, the $AUC_{inf}$ of the total combined amount of deuterated dihydrotetrabenazine is about 610±291 hr*ng/mL.

In certain embodiments, the $AUC_{(0-12)}$ of the total combined amount of deuterated dihydrotetrabenazine is about 370±123.7 hr*ng/mL.

In certain embodiments, the $T_{max}$ of the total combined amount of deuterated dihydrotetrabenazine is about 3.79±0.84 hr.

In certain embodiments, the $T_{half}$ of the total combined amount of deuterated dihydrotetrabenazine is about 8.38±2.17 hr.

In certain embodiments, disclosed herein is a method of treating a VMAT2-mediated disease comprising the administration of an extended release pharmaceutical composition comprising 6 mg $d_6$-tetrabenazine with food, wherein the $C_{max}$ of the total combined amount of deuterated dihydrotetrabenazine is about 15.5±3.5 ng/mL.

In certain embodiments, disclosed herein is an extended release pharmaceutical composition comprising 6 mg $d_6$-tetrabenazine for use in treatment of a VMAT2-mediated disease wherein the pharmaceutical composition is administered with food and the $C_{max}$ of the total combined amount of deuterated dihydrotetrabenazine is about 15.5±3.5 ng/mL.

In certain embodiments, disclosed herein is the use of an extended release pharmaceutical composition comprising 6 mg $d_6$-tetrabenazine for the manufacture of a medicament to treat a VMAT2-mediated disease wherein the pharmaceutical composition is administered with food and the $C_{max}$ of the total combined amount of deuterated dihydrotetrabenazine is about 15.5±3.5 ng/mL.

In certain embodiments, the $AUC_{inf}$ of the total combined amount of deuterated dihydrotetrabenazine is about 132±47 hr*ng/mL.

In certain embodiments, the $AUC_t$ of the total combined amount of deuterated dihydrotetrabenazine is about 122±46 hr*ng/mL.

In certain embodiments, the $T_{max}$ of the total combined amount of deuterated dihydrotetrabenazine is about 3.74±0.99 hr.

In certain embodiments, the $T_{half}$ of the total combined amount of deuterated dihydrotetrabenazine is about 8.64±1.84 hr.

In certain embodiments, disclosed herein is a method of treating a VMAT2-mediated disease comprising the administration of an extended release pharmaceutical composition comprising 12 mg $d_6$-tetrabenazine with food, wherein the $C_{max}$ of the total combined amount of deuterated dihydrotetrabenazine is about 32.1±8.1 ng/mL.

In certain embodiments, disclosed herein is an extended release pharmaceutical composition comprising 12 mg $d_6$-tetrabenazine for use in treatment of a VMAT2-mediated disease wherein the pharmaceutical composition is administered with food and the $C_{max}$ of the total combined amount of deuterated dihydrotetrabenazine is about 32.1±8.1 ng/mL.

In certain embodiments, disclosed herein is the use of an extended release pharmaceutical composition comprising 12 mg $d_6$-tetrabenazine for the manufacture of a medicament to treat a VMAT2-mediated disease wherein the pharmaceutical composition is administered with food and the $C_{max}$ of the total combined amount of deuterated dihydrotetrabenazine is about 32.1±8.1 ng/mL.

In certain embodiments, the $AUC_{inf}$ of the total combined amount of deuterated dihydrotetrabenazine is about 289±115 hr*ng/mL.

In certain embodiments, the $AUC_t$ of the total combined amount of deuterated dihydrotetrabenazine is about 279±114 hr*ng/mL.

In certain embodiments, the $T_{max}$ of the total combined amount of deuterated dihydrotetrabenazine is about 3.90±1.27 hr.

In certain embodiments, the $T_{half}$ of the total combined amount of deuterated dihydrotetrabenazine is about 9.79±2.45 hr.

In certain embodiments, disclosed herein is a method of treating a VMAT2-mediated disease comprising the administration of an extended release pharmaceutical composition comprising 18 mg $d_6$-tetrabenazine with food, wherein the $C_{max}$ of the total combined amount of deuterated dihydrotetrabenazine is about 47.8±12 ng/mL.

In certain embodiments, disclosed herein is an extended release pharmaceutical composition comprising 18 mg $d_6$-tetrabenazine for use in treatment of a VMAT2-mediated disease wherein the pharmaceutical composition is administered with food and the $C_{max}$ of the total combined amount of deuterated dihydrotetrabenazine is about 47.8±12 ng/mL.

In certain embodiments, disclosed herein is the use of an extended release pharmaceutical composition comprising 18 mg $d_6$-tetrabenazine for the manufacture of a medicament to treat a VMAT2-mediated disease wherein the pharmaceutical composition is administered with food and the $C_{max}$ of the total combined amount of deuterated dihydrotetrabenazine is about 47.8±12 ng/mL.

In certain embodiments, the $AUC_{inf}$ of the total combined amount of deuterated dihydrotetrabenazine is about 419±165 hr*ng/mL.

In certain embodiments, the $AUC_t$ of the total combined amount of deuterated dihydrotetrabenazine is about 407±163 hr*ng/mL.

In certain embodiments, the $T_{max}$ of the total combined amount of deuterated dihydrotetrabenazine is about 3.63±0.85 hr.

In certain embodiments, the $T_{half}$ of the total combined amount of deuterated dihydrotetrabenazine is about 10.2±3.3 hr.

In certain embodiments, disclosed herein is a method of treating a VMAT2-mediated disease comprising the administration of an extended release pharmaceutical composition comprising 24 mg $d_6$-tetrabenazine with food, wherein the $C_{max}$ of the total combined amount of deuterated dihydrotetrabenazine is about 60.9±13.8 ng/mL.

In certain embodiments, disclosed herein is an extended release pharmaceutical composition comprising 24 mg $d_6$-tetrabenazine for use in treatment of a VMAT2-mediated disease wherein the pharmaceutical composition is administered with food and the $C_{max}$ of the total combined amount of deuterated dihydrotetrabenazine is about 60.9±13.8 ng/mL.

In certain embodiments, disclosed herein is the use of an extended release pharmaceutical composition comprising 24 mg $d_6$-tetrabenazine for the manufacture of a medicament to treat a VMAT2-mediated disease wherein the pharmaceutical composition is administered with food and the $C_{max}$ of the total combined amount of deuterated dihydrotetrabenazine is about 60.9±13.8 ng/mL.

In certain embodiments, the $AUC_{inf}$ of the total combined amount of deuterated dihydrotetrabenazine is about 580±229 hr*ng/mL.

In certain embodiments, the $AUC_t$ of the total combined amount of deuterated dihydrotetrabenazine is about 569±225 hr*ng/mL.

In certain embodiments, the $T_{max}$ of the total combined amount of deuterated dihydrotetrabenazine is about 3.92±1.19 hr.

In certain embodiments, the $T_{half}$ of the total combined amount of deuterated dihydrotetrabenazine is about 6.00±1.60 hr.

In certain embodiments, disclosed herein is a method of treating a VMAT2-mediated disease comprising the administration of an extended release pharmaceutical composition comprising 18 mg $d_6$-tetrabenazine with a high-fat meal, wherein the $C_{max}$ of the total combined amount of deuterated dihydrotetrabenazine is about 49.0±8.1 ng/mL.

In certain embodiments, disclosed herein is an extended release pharmaceutical composition comprising 18 mg $d_6$-tetrabenazine for use in treatment of a VMAT2-mediated disease wherein the pharmaceutical composition is administered with a high-fat meal and the $C_{max}$ of the total combined amount of deuterated dihydrotetrabenazine is about 49.0±8.1 ng/mL.

In certain embodiments, disclosed herein is the use of an extended release pharmaceutical composition comprising 18 mg $d_6$-tetrabenazine for the manufacture of a medicament to treat a VMAT2-mediated disease wherein the pharmaceutical composition is administered with a high-fat meal and the $C_{max}$ of the total combined amount of deuterated dihydrotetrabenazine is about 60.9±13.8 ng/mL.

In certain embodiments, the $AUC_{inf}$ of the total combined amount of deuterated dihydrotetrabenazine is about 436±129 hr*ng/mL.

In certain embodiments, the $AUC_t$ of the total combined amount of deuterated dihydrotetrabenazine is about 425±127 hr*ng/mL.

In certain embodiments, the $T_{max}$ of the total combined amount of deuterated dihydrotetrabenazine is about 4.09±1.25 hr.

In certain embodiments, the $T_{half}$ of the total combined amount of deuterated dihydrotetrabenazine is about 10.2±2.5 hr.

In certain embodiments, disclosed herein is a method of treating a VMAT2-mediated disease comprising the administration of an extended release pharmaceutical composition comprising 15 mg $d_6$-tetrabenazine with food, wherein the $C_{max}$ of the total combined amount of deuterated dihydrotetrabenazine is about 33.3±11 ng/mL.

In certain embodiments, disclosed herein is an extended release pharmaceutical composition comprising 15 mg $d_6$-tetrabenazine for use in treatment of a VMAT2-mediated disease wherein the pharmaceutical composition is administered with food and the $C_{max}$ of the total combined amount of deuterated dihydrotetrabenazine is about 33.3±11 ng/mL.

In certain embodiments, disclosed herein is the use of an extended release pharmaceutical composition comprising 15 mg $d_6$-tetrabenazine for the manufacture of a medicament to treat a VMAT2-mediated disease wherein the pharmaceutical composition is administered with food and the $C_{max}$ of the total combined amount of deuterated dihydrotetrabenazine is about 33.3±11 ng/mL.

In certain embodiments, the $AUC_{inf}$ of the total combined amount of deuterated dihydrotetrabenazine is about 305±141 hr*ng/mL.

In certain embodiments, the $AUC_{(0-12)}$ of the total combined amount of deuterated dihydrotetrabenazine is about 189±65 hr*ng/mL.

In certain embodiments, the $T_{max}$ of the total combined amount of deuterated dihydrotetrabenazine is about 6.00 hr.

In certain embodiments, the $T_{half}$ of the total combined amount of deuterated dihydrotetrabenazine is about 6.00±1.60 hr.

In certain embodiments, disclosed herein is a method of treating a VMAT2-mediated disease comprising the administration of an extended release pharmaceutical composition comprising $d_6$-tetrabenazine with food, wherein the ratio of fed to fasted $C_{max}$ of the total combined amount of deuterated dihydrotetrabenazine is greater than 1.

In certain embodiments, disclosed herein is an extended release pharmaceutical composition comprising $d_6$-tetrabenazine for use in treatment of a VMAT2-mediated disease wherein the pharmaceutical composition is administered with food and the ratio of fed to fasted $C_{max}$ of the total combined amount of deuterated dihydrotetrabenazine is greater than 1.

In certain embodiments, disclosed herein is an extended release pharmaceutical composition comprising $d_6$-tetrabenazine for use in the manufacture of a medicament to treat a VMAT2-mediated disease wherein the pharmaceutical composition is administered with food and the ratio of fed to fasted $C_{max}$ of the total combined amount of deuterated dihydrotetrabenazine is greater than 1.

In certain embodiments, the ratio of fed to fasted $C_{max}$ is greater than about 1.4.

In certain embodiments, the ratio of fed to fasted $C_{max}$ is greater than about 1.9.

In certain embodiments, disclosed herein is a method of treating a VMAT2-mediated disease comprising the administration of an extended release pharmaceutical composition comprising $d_6$-tetrabenazine with food, wherein the ratio of fed to fasted $AUC_{inf}$ of the total combined amount of deuterated dihydrotetrabenazine is greater than 1.

In certain embodiments, disclosed herein is an extended release pharmaceutical composition comprising $d_6$-tetrabenazine for use in treatment of a VMAT2-mediated disease wherein the pharmaceutical composition is administered with food and the ratio of fed to fasted $AUC_{inf}$ of the total combined amount of deuterated dihydrotetrabenazine is greater than 1.

In certain embodiments, disclosed herein is an extended release pharmaceutical composition comprising $d_6$-tetrabenazine for use in the manufacture of a medicament to treat a VMAT2-mediated disease wherein the pharmaceutical composition is administered with food and the ratio of fed to fasted $AUC_{inf}$ of the total combined amount of deuterated dihydrotetrabenazine is greater than 1.

In certain embodiments, the ratio of fed to fasted $AUC_{inf}$ is greater than about 1.1.

In certain embodiments, the ratio of fed to fasted $AUC_{inf}$ is greater than about 1.2.

In certain embodiments, disclosed herein is a method of treating a VMAT2-mediated disease comprising the administration of an extended release pharmaceutical composition comprising d₆-tetrabenazine with food, wherein the ratio of fed to fasted $AUC_t$ of the total combined amount of deuterated dihydrotetrabenazine is greater than 1.

In certain embodiments, disclosed herein is an extended release pharmaceutical composition comprising d₆-tetrabenazine for use in treatment of a VMAT2-mediated disease wherein the pharmaceutical composition is administered with food and the ratio of fed to fasted $AUC_t$ of the total combined amount of deuterated dihydrotetrabenazine is greater than 1.

In certain embodiments, disclosed herein is an extended release pharmaceutical composition comprising d₆-tetrabenazine for use in the manufacture of a medicament to treat a VMAT2-mediated disease wherein the pharmaceutical composition is administered with food and the ratio of fed to fasted $AUC_t$ of the total combined amount of deuterated dihydrotetrabenazine is greater than 1.

In certain embodiments, the ratio of fed to fasted $AUC_t$ is greater than about 1.1.

In certain embodiments, the ratio of fed to fasted $AUC_t$ is greater than about 1.2.

In certain embodiments, disclosed herein is a method of treating a VMAT2-mediated disease comprising the administration of multiple doses of an extended release pharmaceutical composition comprising 7.5 mg d₆-tetrabenazine wherein the steady state $C_{max}$ of the total combined amount of deuterated dihydrotetrabenazine is about 31.5±8.16 ng/mL.

In certain embodiments, disclosed herein is an extended release pharmaceutical composition comprising 7.5 mg d₆-tetrabenazine for use in treatment of a VMAT2-mediated disease wherein the steady state $C_{max}$ of the total combined amount of deuterated dihydrotetrabenazine is about 31.5±8.16 ng/mL.

In certain embodiments, disclosed herein is an extended release pharmaceutical composition comprising 7.5 mg d₆-tetrabenazine for use in the manufacture of a medicament to treat a VMAT2-mediated disease wherein the steady state $C_{max}$ of the total combined amount of deuterated dihydrotetrabenazine is about 31.5±8.16 ng/mL.

In certain embodiments, the steady state $AUC_{(0-12)}$ of the total combined amount of deuterated dihydrotetrabenazine is about 203±69.2 hr*ng/mL.

In certain embodiments, the steady state $T_{max}$ of the total combined amount of deuterated dihydrotetrabenazine is about 3.17±0.49 hr.

In certain embodiments, the steady state $T_{half}$ of the total combined amount of deuterated dihydrotetrabenazine is about 8.8±1.97 hr.

In certain embodiments, disclosed herein is a method of treating a VMAT2-mediated disease comprising the administration of multiple doses of an extended release pharmaceutical composition comprising 15 mg d₆-tetrabenazine wherein the steady state $C_{max}$ of the total combined amount of deuterated dihydrotetrabenazine is about 72.0±14.5 ng/mL.

In certain embodiments, disclosed herein is an extended release pharmaceutical composition comprising 15 mg d₆-tetrabenazine for use in treatment of a VMAT2-mediated disease wherein the steady state $C_{max}$ of the total combined amount of deuterated dihydrotetrabenazine is about 72.0±14.5 ng/mL.

In certain embodiments, disclosed herein is an extended release pharmaceutical composition comprising 15 mg d₆-tetrabenazine for use in the manufacture of a medicament to treat a VMAT2-mediated disease wherein the steady state $C_{max}$ of the total combined amount of deuterated dihydrotetrabenazine is about 72.0±14.5 ng/mL.

In certain embodiments, the steady state $AUC_{(0-12)}$ of the total combined amount of deuterated dihydrotetrabenazine is about 443±125.8 hr*ng/mL.

In certain embodiments, the steady state $T_{max}$ of the total combined amount of deuterated dihydrotetrabenazine is about 2.78±0.41 hr.

In certain embodiments, the steady state $T_{half}$ of the total combined amount of deuterated dihydrotetrabenazine is about 9.06±2.53 hr.

In certain embodiments, disclosed herein is a method of treating a VMAT2-mediated disease comprising the administration of multiple doses of an extended release pharmaceutical composition comprising 22.5 mg d₆-tetrabenazine wherein the steady state $C_{max}$ of the total combined amount of deuterated dihydrotetrabenazine is about 111.0±47.2 ng/mL.

In certain embodiments, disclosed herein is an extended release pharmaceutical composition comprising 22.5 mg d₆-tetrabenazine for use in treatment of a VMAT2-mediated disease wherein the steady state $C_{max}$ of the total combined amount of deuterated dihydrotetrabenazine is about 111.0±47.2 ng/mL.

In certain embodiments, disclosed herein is an extended release pharmaceutical composition comprising 22.5 mg d₆-tetrabenazine for use in the manufacture of a medicament to treat a VMAT2-mediated disease wherein the steady state $C_{max}$ of the total combined amount of deuterated dihydrotetrabenazine is about 111.0±47.2 ng/mL.

In certain embodiments, the steady state $AUC_{(0-12)}$ of the total combined amount of deuterated dihydrotetrabenazine is about 769±357 hr*ng/mL.

In certain embodiments, the steady state $T_{half}$ of the total combined amount of deuterated dihydrotetrabenazine is about 3.75±0.79 hr.

In certain embodiments, the steady state $T_{half}$ of the total combined amount of deuterated dihydrotetrabenazine is about 9.50±2.32 hr.

In certain embodiments, the VMAT2-mediated disorder is a chronic hyperkinetic movement disorder.

In certain embodiments, the VMAT2-mediated disorder is selected from the group consisting of Huntington's disease, hemiballismus, senile chorea, tic disorders, tardive dyskinesia, dystonia, Tourette's syndrome, depression, cancer, rheumatoid arthritis, psychosis, multiple sclerosis, and asthma.

In certain embodiments, the VMAT2-mediated disorder is Huntington's disease.

In certain embodiments, the VMAT2-mediated disorder is hemiballismus.

In certain embodiments, the VMAT2-mediated disorder is senile chorea.

In certain embodiments, the VMAT2-mediated disorder is a tic disorder.

In certain embodiments, the VMAT2-mediated disorder is tardive dyskinesia.

In certain embodiments, the VMAT2-mediated disorder is dystonia.

In certain embodiments, the VMAT2-mediated disorder is Tourette's syndrome.

In certain embodiments, the VMAT2-mediated disorder is depression.

In certain embodiments, the VMAT2-mediated disorder is cancer.

In certain embodiments, the VMAT2-mediated disorder is rheumatoid arthritis.

In certain embodiments, the VMAT2-mediated disorder is psychosis.

In certain embodiments, the VMAT2-mediated disorder is multiple sclerosis.

In certain embodiments, the VMAT2-mediated disorder is asthma.

In certain embodiments, disclosed herein is a compound which is $d_6$-tetrabenazine polymorph Form I.

In certain embodiments, the compound is identifiable by reference to an X-ray diffractogram that includes the major peaks, in terms of 2θ, at about 8.3, about 11.6, about 13.9, about 20.0, and about 23.7.

In certain embodiments, the compound is identifiable by reference to an X-ray diffractogram that includes the major peaks, in terms of 2θ, at about 8.3, about 9.8, about 11.6, about 12.0, about 13.9, about 20.0, about 22.0, about 23.7, about 24.4, about 33.5, and about 42.3.

Figure 9:
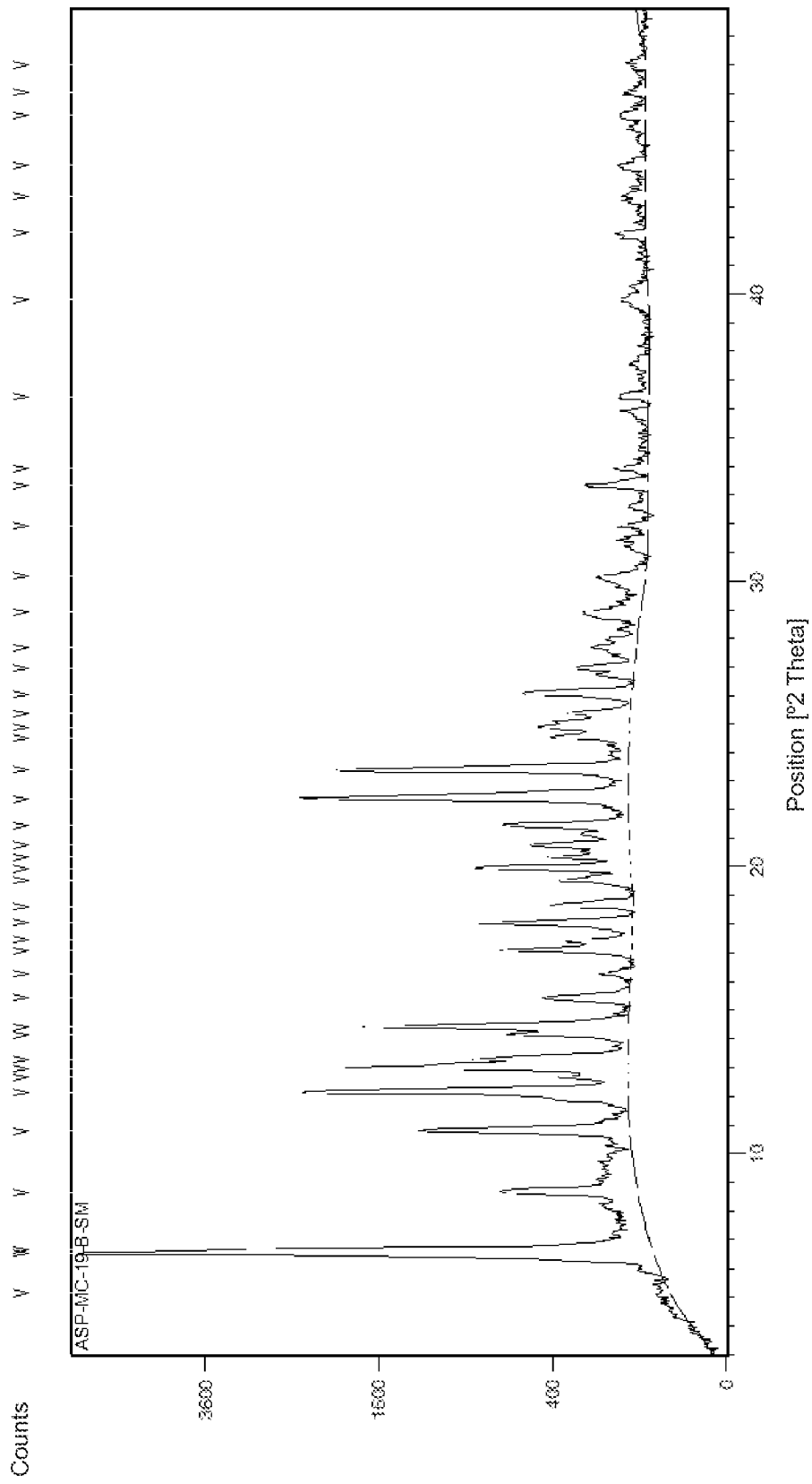
FIG. 9: Powder X-ray diffraction (pXRD) profile of d$_6$-tetrabenazine, Form I.

In certain embodiments, the compound is identifiable by reference to a X-ray powder diffraction pattern substantially as shown in FIG. 9.

In certain embodiments, the compound has a differential calorimetry trace comprising an endotherm between about 115 and about 135° C.

Figure 8:
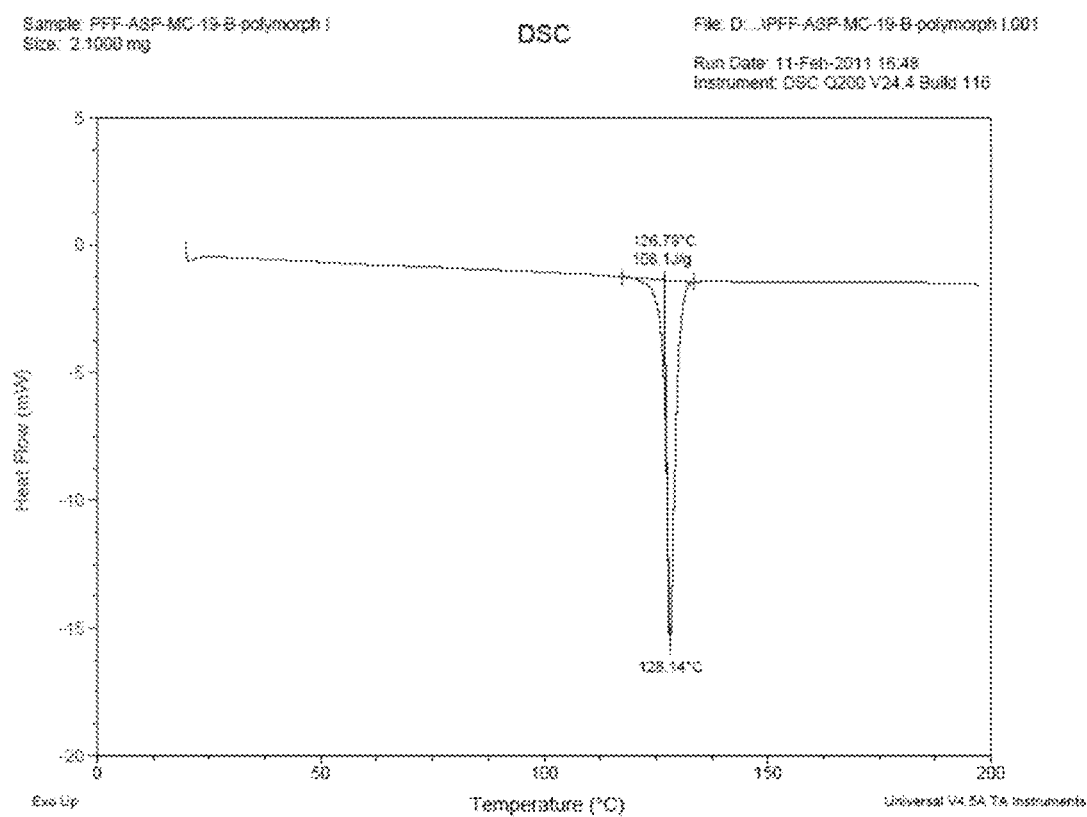
FIG. 8: Differential scanning calorimetry (DSC) profile of d$_6$-tetrabenazine, Form I.

In certain embodiments, the compound has a differential calorimetry trace substantially as shown in FIG. 8.

In certain embodiments, the compound has a thermogravimetric analysis profile showing about 1.5% weight loss below about 150° C.

Figure 7:
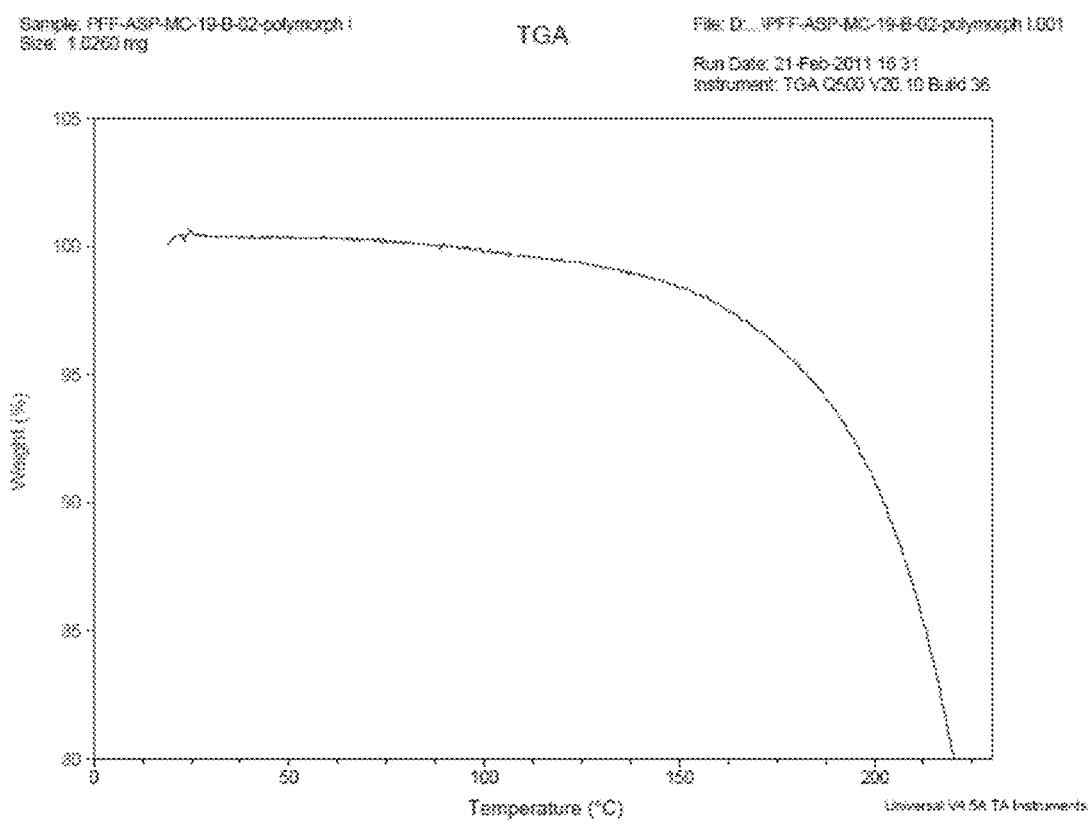
FIG. 7: Thermogravimetric analysis (TGA) profile of d$_6$-tetrabenazine, Form I.

In certain embodiments, the compound has a thermogravimetric analysis profile substantially as shown in FIG. 7.

In certain embodiments, disclosed herein is a process of preparing a compound which is $d_6$-tetrabenazine polymorph Form I, comprising the step of cooling a saturated ethanol solution of $d_6$-tetrabenazine.

In certain embodiments, the $d_6$-tetrabenazine is dissolved in 3 volumes of ethanol, then cooled to room temperature at the rate of 20° C./hr.

In certain embodiments, the process further comprises formulating the $d_6$-tetrabenazine polymorph Form I to yield a pharmaceutical composition.

In certain embodiments, disclosed herein is a compound which is $d_6$-tetrabenazine polymorph Form I, prepared by a process comprising the step of cooling a saturated ethanol solution of $d_6$-tetrabenazine.

In certain embodiments, disclosed herein is a pharmaceutical composition comprising $d_6$-tetrabenazine polymorph Form I.

In certain embodiments, disclosed herein is a pharmaceutical composition comprising $d_6$-tetrabenazine polymorph Form I, wherein the $d_6$-tetrabenazine polymorph Form I is prepared by a process comprising the step of cooling a saturated ethanol solution of $d_6$-tetrabenazine.

In certain embodiments, disclosed herein is a method of treating a VMAT2-mediated disorder comprising the administration, to a patient in need thereof, a therapeutically effective amount of $d_6$-tetrabenazine polymorph Form I.

In certain embodiments, disclosed herein is a method of treating a VMAT2-mediated disorder comprising the administration, to a patient in need thereof, a therapeutically effective amount of $d_6$-tetrabenazine polymorph Form I prepared by a process comprising the step of cooling a saturated ethanol solution of $d_6$-tetrabenazine.

In certain embodiments, disclosed herein is a compound which is $d_6$-tetrabenazine polymorph Form I for use in the treatment of a VMAT2-mediated disorder.

In certain embodiments, disclosed herein is a pharmaceutical composition comprising a compound which is $d_6$-tetrabenazine polymorph Form I for use in the treatment of a VMAT2-mediated disorder.

In certain embodiments, disclosed herein is the use of a compound which is $d_6$-tetrabenazine polymorph Form I for the manufacture of a medicament for the treatment of a VMAT2-mediated disorder.

In certain embodiments, disclosed herein is the use of a pharmaceutical composition comprising a compound which is $d_6$-tetrabenazine polymorph Form I for the manufacture of a medicament for the treatment of a VMAT2-mediated disorder.

In certain embodiments, disclosed herein is a compound which is $d_6$-tetrabenazine polymorph Form II.

In certain embodiments, the compound is identifiable by reference to an X-ray diffractogram that includes the major peaks, in terms of 2θ, at about 8.3, about 11.6, about 13.9, about 20.0, and about 23.7.

In certain embodiments, the compound is identifiable by reference to an X-ray diffractogram that includes the major peaks, in terms of 2θ, at about 8.3, about 9.8, about 11.6, about 12.0, about 13.9, about 20.0, about 22.0, about 23.7, about 24.4, about 33.5, and about 42.3.

Figure 12:
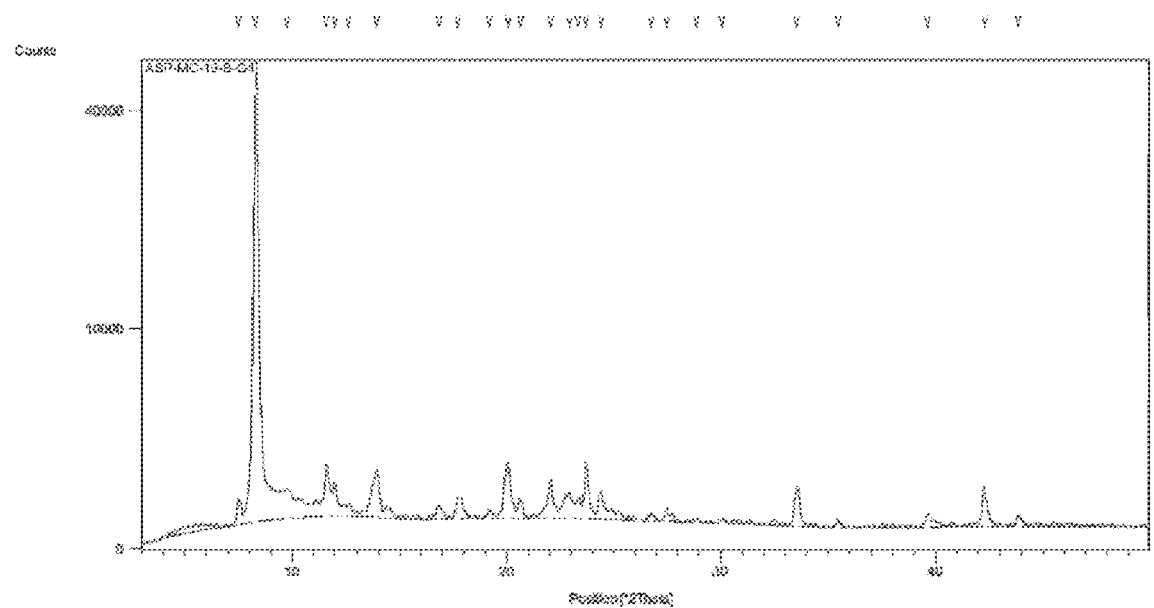
FIG. 12: Powder X-ray diffraction (pXRD) profile of d$_6$-tetrabenazine, Form II.

In certain embodiments, the compound is identifiable by reference to a X-ray powder diffraction pattern substantially as shown in FIG. 12.

In certain embodiments, the compound has a differential calorimetry trace comprising an endotherm between about 120 and about 140° C.

Figure 11:
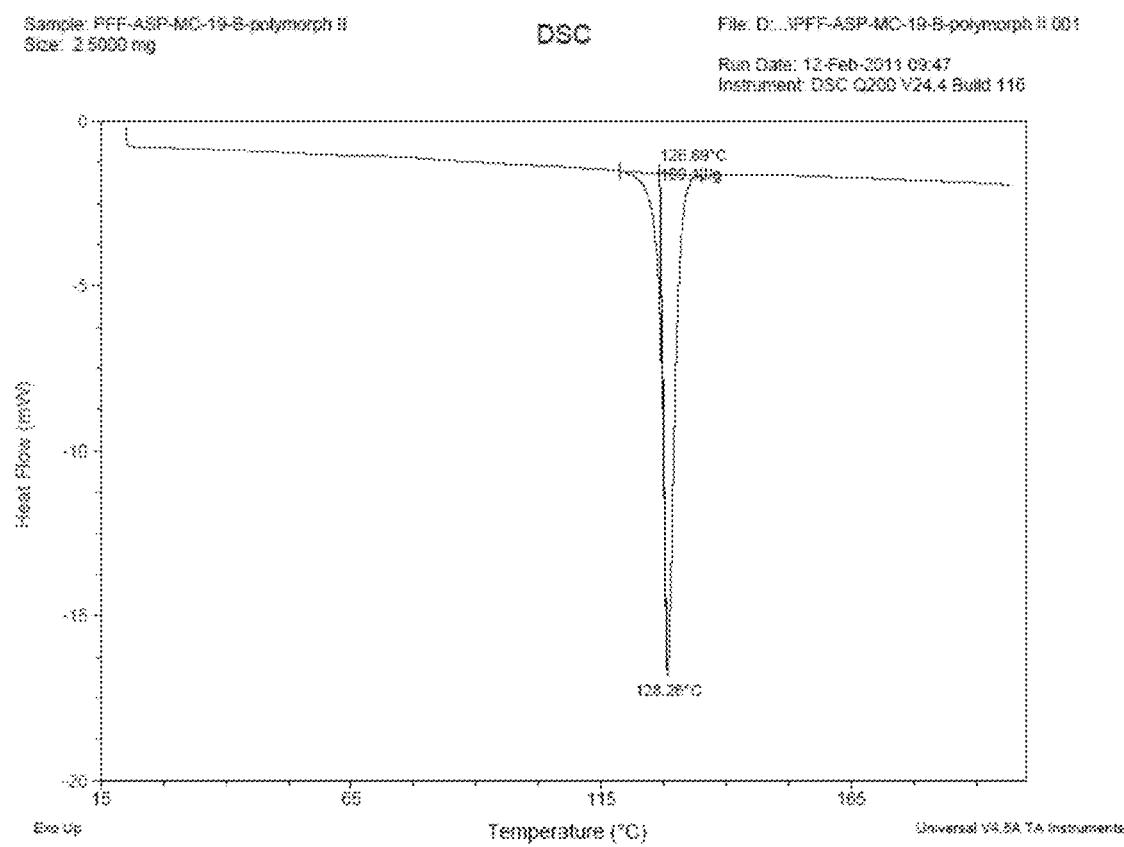
FIG. 11: Differential scanning calorimetry (DSC) profile of d$_6$-tetrabenazine, Form II.

In certain embodiments, the compound has a differential calorimetry trace substantially as shown in FIG. 11.

In certain embodiments, the compound has a thermogravimetric analysis profile showing about 1.5% weight loss below about 160° C.

Figure 10:
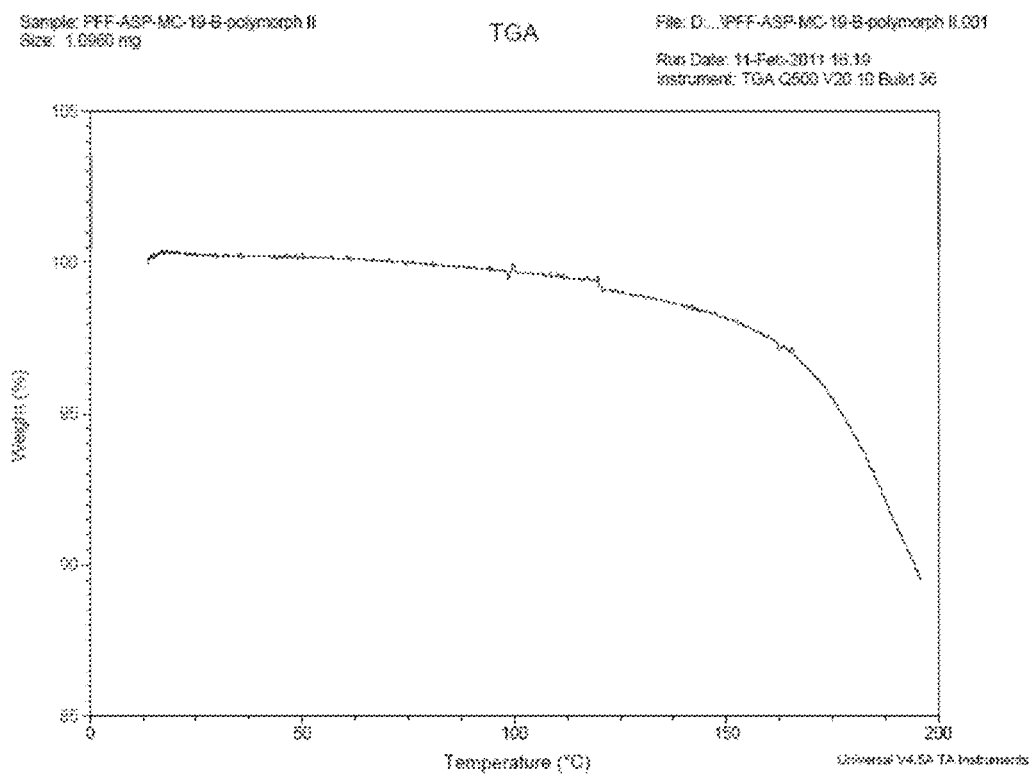
FIG. 10: Thermogravimetric analysis (TGA) profile of d$_6$-tetrabenazine, Form II.

In certain embodiments, the compound has a thermogravimetric analysis profile substantially as shown in FIG. 10.

In certain embodiments, disclosed herein is a process of preparing a compound which is $d_6$-tetrabenazine polymorph Form II, comprising the step of evaporating a saturated methanol solution of $d_6$-tetrabenazine.

In certain embodiments, the methanol solution of $d_6$-tetrabenazine is evaporated slowly at ambient temperature and humidity.

In certain embodiments, the process further comprises formulating the $d_6$-tetrabenazine polymorph Form II to yield a pharmaceutical composition.

In certain embodiments, disclosed herein is a compound which is $d_6$-tetrabenazine polymorph Form II, prepared by a process comprising the step of evaporating a saturated methanol solution of $d_6$-tetrabenazine.

In certain embodiments, disclosed herein is a pharmaceutical composition comprising $d_6$-tetrabenazine polymorph Form II.

In certain embodiments, disclosed herein is a pharmaceutical composition comprising $d_6$-tetrabenazine polymorph Form II, wherein the $d_6$-tetrabenazine polymorph Form II is prepared by a process comprising the step of evaporating a saturated methanol solution of $d_6$-tetrabenazine.

In certain embodiments, disclosed herein is a method of treating a VMAT2-mediated disorder comprising the administration, to a patient in need thereof, a therapeutically effective amount of $d_6$-tetrabenazine polymorph Form II.

In certain embodiments, disclosed herein is a method of treating a VMAT2-mediated disorder comprising the administration, to a patient in need thereof, a therapeutically effective amount of $d_6$-tetrabenazine polymorph Form II prepared by a process comprising the step of evaporating a saturated methanol solution of $d_6$-tetrabenazine.

In certain embodiments, disclosed herein is a compound which is $d_6$-tetrabenazine polymorph Form II for use in the treatment of a VMAT2-mediated disorder.

In certain embodiments, disclosed herein is a pharmaceutical composition comprising a compound which is $d_6$-tetrabenazine polymorph Form II for use in the treatment of a VMAT2-mediated disorder.

In certain embodiments, disclosed herein is the use of a compound which is $d_6$-tetrabenazine polymorph Form II for the manufacture of a medicament for the treatment of a VMAT2-mediated disorder.

In certain embodiments, disclosed herein is the use of a pharmaceutical composition comprising a compound which is $d_6$-tetrabenazine polymorph Form II for the manufacture of a medicament for the treatment of a VMAT2-mediated disorder.

In certain embodiments of the present invention, compositions disclosed herein comprise compounds of structural Formula I:

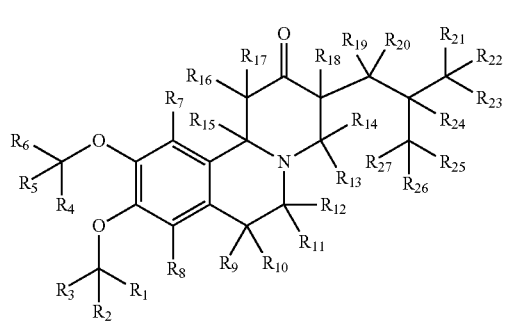

(I)

or a salt, solvate, or prodrug thereof, wherein:

$R_1$-$R_{27}$ are independently selected from the group consisting of hydrogen and deuterium; and at least one of $R_1$-$R_{27}$ is deuterium.

In certain embodiments of the present invention, compositions disclosed herein comprise compounds of structural Formula II:

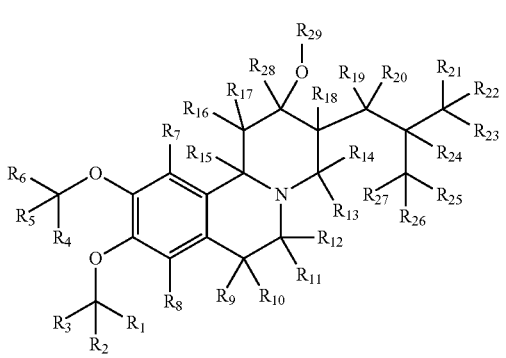

(II)

or a salt thereof, wherein:

$R_1$-$R_{28}$ are independently selected from the group consisting of hydrogen and deuterium;

$R_{29}$ is selected from the group consisting of hydrogen, deuterium, —C(O)O-alkyl and —C(O)—$C_{1-6}$alkyl, or a group cleavable under physiological conditions, wherein said alkyl or $C_{1-6}$alkyl is optionally substituted with one or more substituents selected from the group consisting of —NH—C(NH)NH$_2$, —CO$_2$H, —CO$_2$alkyl, —SH, —C(O)NH$_2$, —NH$_2$, phenyl, —OH, 4-hydroxyphenyl, imidazolyl, and indolyl, and any $R_{29}$ substituent is further optionally substituted with deuterium; and at least one of $R_1$-$R_{29}$ is deuterium or contains deuterium.

In certain embodiments of the present invention, compositions disclosed herein comprise the compound:

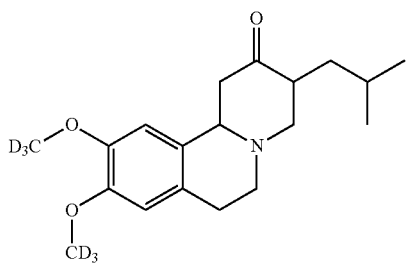 [SMILES: [2H]C([2H])([2H])Oc1cc2c(cc1OC([2H])([2H])[2H])C1CC(=O)C(CC(C)C)CN1CC2]

In certain embodiments of the present invention, compositions disclosed herein comprise the compound:

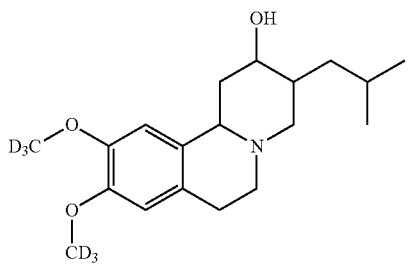 [SMILES: [2H]C([2H])([2H])Oc1cc2c(cc1OC([2H])([2H])[2H])C1CC(O)C(CC(C)C)CN1CC2]

In certain embodiments of the present invention, compositions disclosed herein comprise one or more of the following compounds:

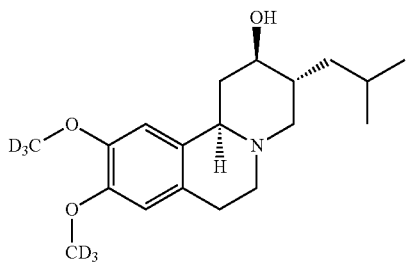

(+)-$d_6$-α-HTBZ

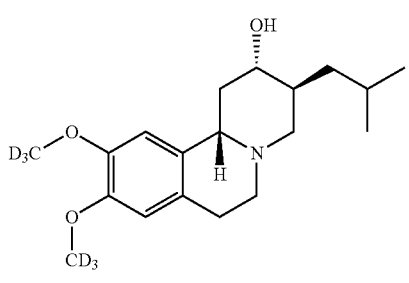

(−)-$d_6$-α-HTBZ

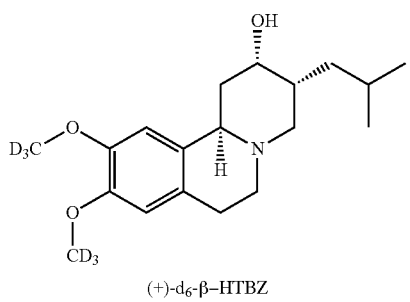

(+)-d6-β–HTBZ

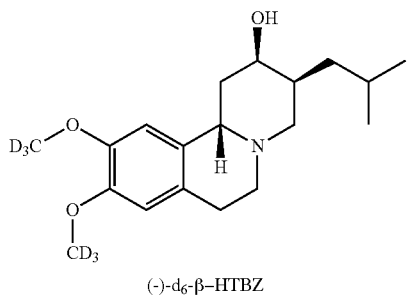

(-)-d6-β–HTBZ

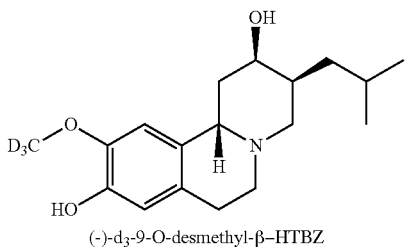

(-)-d3-9-O-desmethyl-β–HTBZ

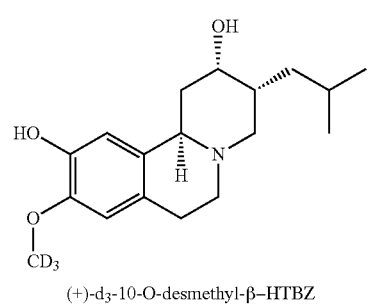

(+)-d3-10-O-desmethyl-β–HTBZ

In certain embodiments of the present invention, compositions disclosed herein comprise one or more of the following compounds:

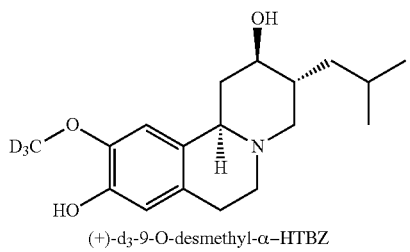

(+)-d3-9-O-desmethyl-α–HTBZ

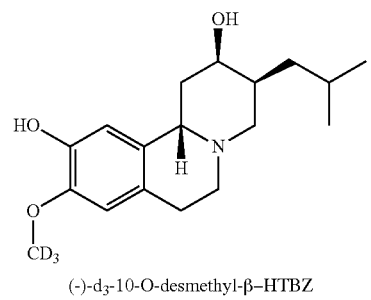

(-)-d3-10-O-desmethyl-β–HTBZ

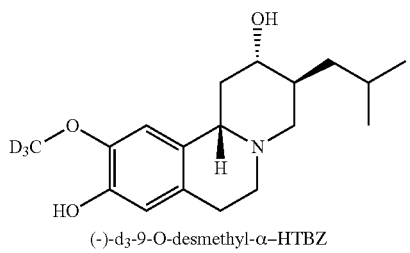

(-)-d3-9-O-desmethyl-α–HTBZ

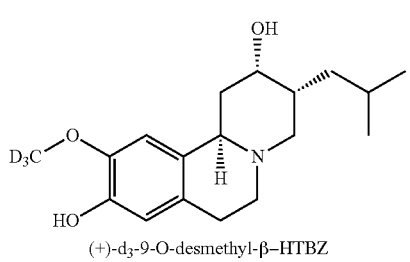

(+)-d3-9-O-desmethyl-β–HTBZ

In certain embodiments of the present invention, compositions disclosed herein comprise one or more of the following compounds:

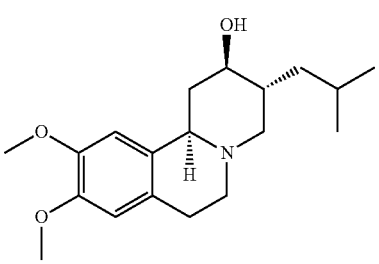

(+)-α–HTBZ

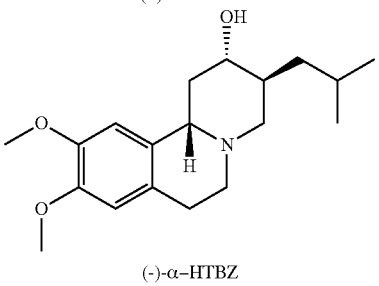

(-)-α–HTBZ

-continued

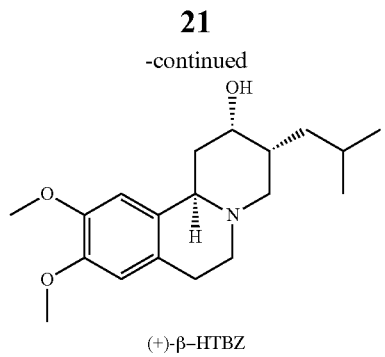
(+)-β-HTBZ

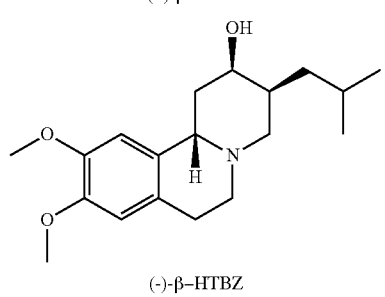
(-)-β-HTBZ

In certain embodiments of the present invention, compositions disclosed herein comprise one or more of the following compounds:

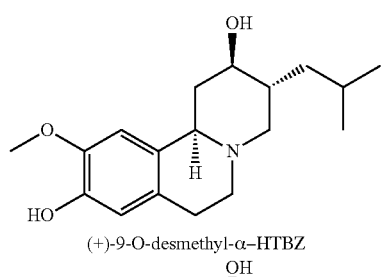
(+)-9-O-desmethyl-α-HTBZ

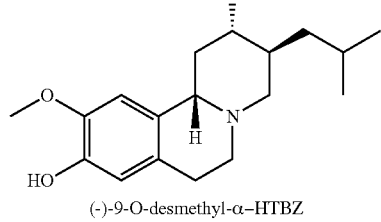
(-)-9-O-desmethyl-α-HTBZ

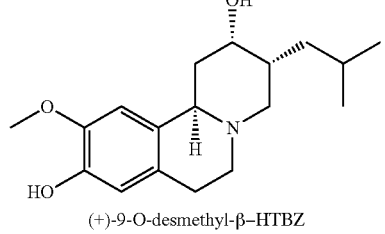
(+)-9-O-desmethyl-β-HTBZ

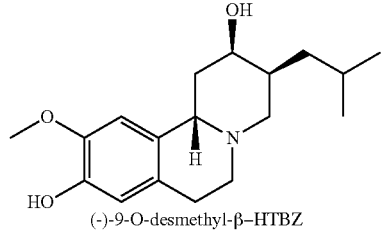
(-)-9-O-desmethyl-β-HTBZ

-continued

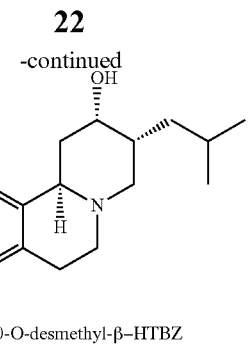
(+)-10-O-desmethyl-β-HTBZ

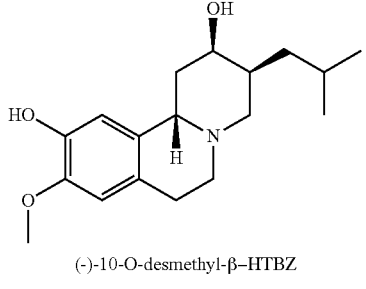
(-)-10-O-desmethyl-β-HTBZ

Certain compounds disclosed herein may possess useful VMAT2 inhibiting activity, and may be used in the treatment or prophylaxis of a disorder in which VMAT2 plays an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for inhibiting VMAT2. Other embodiments provide methods for treating a VMAT2-mediated disorder in a patient in need of such treatment, comprising administering to said patient a therapeutically effective amount of a compound or composition according to the present invention. Also provided is the use of certain compounds disclosed herein for use in the manufacture of a medicament for the prevention or treatment of a disorder ameliorated by the inhibition of VMAT2.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ ... to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The terms $d_6$-tetrabenazine and (+/−)-cis-$d_6$-tetrabenazine refer to a racemic mixture of (3R,11bR)-1,3,4,6,7,11b-hexahydro-9,10-di(methoxy-$d_3$)-3-(2-methylpropyl)-2H-benzo[a]quinolizin-2-one and (3S,11bS)-1,3,4,6,7,11b-hexahydro-9,10-di(methoxy-$d_3$)-3-(2-methylpropyl)-2H-benzo[a]quinolizin-2-one, which have the following structures:

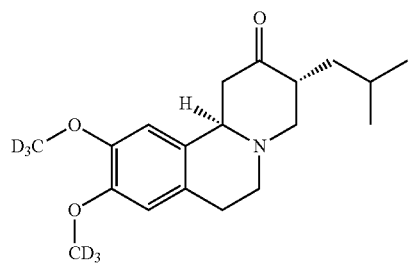

(3R,11bR)-1,3,4,6,7,11b-hexahydro-9,10-di(methoxy-$d_3$)-3-(2-methylpropyl)-2H-benzo[a]quinolizin-2-one

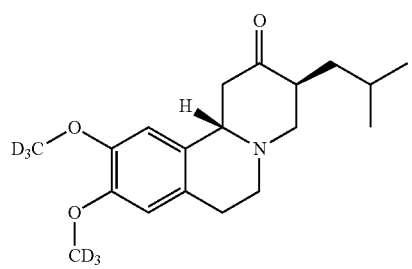

(3S,11bS)-1,3,4,6,7,11b-hexahydro-9,10-di(methoxy-$d_3$)-3-(2-methylpropyl)-2H-benzo[a]quinolizin-2-one The term (+/−)-trans-$d_6$-tetrabenazine refers to a racemic mixture of (3R,11bS)-1,3,4,6,7,11b-hexahydro-9,10-di(methoxy-$d_3$)-3-(2-methylpropyl)-2H-benzo[a]quinolizin-2-one and (3S,11bR)-1,3,4,6,7,11b-hexahydro-9,10-di(methoxy-$d_3$)-3-(2-methylpropyl)-2H-benzo[a]quinolizin-2-one, which have the following structures:

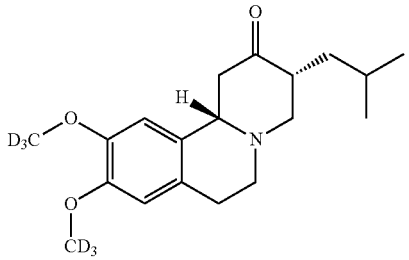 [SMILES: [2H]C([2H])([2H])Oc1cc2c(cc1OC([2H])([2H])[2H])[C@@H]1CC(=O)[C@H](CC(C)C)CN1CC2]

(3R,11bS)-1,3,4,6,7,11b-hexahydro-9,10-di(methoxy-$d_3$)-3-(2-methylpropyl)-2H-benzo[a]quinolizin-2-one

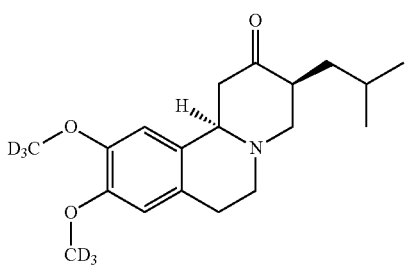 [SMILES: [2H]C([2H])([2H])Oc1cc2c(cc1OC([2H])([2H])[2H])[C@H]1CC(=O)[C@@H](CC(C)C)CN1CC2]

(3S,11bR)-1,3,4,6,7,11b-hexahydro-9,10-di(methoxy-$d_3$)-3-(2-methylpropyl)-2H-benzo[a]quinolizin-2-one The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_1$-$R_{29}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The terms "treat," "treating," and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent," "preventing," and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "chronic hyperkinetic movement disorders" refers to disorders characterized by non-purposeful, repetitive, disordered motor acts, variously termed "compulsive", "rhythmical", or "stereotyped." In humans, chronic hyperkinetic movement disorders can be psychogenic (e.g., tics), idiopathic (as in, e.g., Tourette's syndrome and Parkinson's Disease, genetic (as in, e.g., the chorea characteristic of Huntington's Disease), infectious (as in, e.g., Sydenham's Chorea), or, as in tardive dyskinesia, drug-induced. Unless otherwise stated, "chronic hyperkinetic movement disorders" refers to and includes all psychogenic, idiopathic, genetic, and drug-induced movement disorders.

The term "stereotyped" refers to a repeated behavior that appears repetitively with slight variation or, less commonly, as a complex series of movements.

The term "VMAT2" refers to vesicular monoamine transporter 2, an integral membrane protein that acts to transport monoamines—particularly neurotransmitters such as dopamine, norepinephrine, serotonin, and histamine—from cellular cytosol into synaptic vesicles.

The term "VMAT2-mediated disorder," refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The terms "active ingredient," "active compound," and "active substance" refer to a compound, which is administered, alone or in combination with one or more pharmaceutically acceptable excipients or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use," Stah and Wermuth, Ed., (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

References to a compound of a formula and subgroups thereof include ionic forms, polymorphs, pseudopolymorphs, amorphous forms, and solvates thereof. "Crystalline form," "polymorph," and "novel form" may be used interchangeably herein, and are meant to include all crystalline and amorphous forms of the compound, including, for example, polymorphs, pseudopolymorphs, solvates (including hydrates), co crystals, unsolvated polymorphs (including anhydrates), conformational polymorphs, and amorphous forms, as well as mixtures thereof, unless a particular crystalline or amorphous form is referred to. In some embodiments, references to a compound include polymorphs, solvates, and/or co crystals thereof. In some embodiments, references to a compound of a formula and subgroups thereof include polymorphs thereof. Similarly, the term "salts" includes polymorphs of salts of compounds.

Pharmaceutical Formulations

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc., New York, N.Y., 2002; Vol. 126).

The compositions include those suitable for oral administration. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In certain embodiments, diluents are selected from the group consisting of mannitol powder, spray dried mannitol, microcrystalline cellulose, lactose, dicalcium phosphate, tricalcium phosphate, starch, pregelatinized starch, compressible sugars, silicified microcrystalline cellulose, and calcium carbonate.

In certain embodiments, surfactants are selected from the group consisting of Tween 80, sodium lauryl sulfate, and docusate sodium.

In certain embodiments, binders are selected from the group consisting of povidone (PVP) K29/32, hydroxypropylcellulose (HPC), hydroxypropylmethylcellulose (HPMC), ethylcellulose (EC), corn starch, pregelatinized starch, gelatin, and sugar.

In certain embodiments, lubricants are selected from the group consisting of magnesium stearate, stearic acid, sodium stearyl fumarate, calcium stearate, hydrogenated vegetable oil, mineral oil, polyethylene glycol, polyethylene glycol 4000-6000, talc, and glyceryl behenate.

In certain embodiments, sustained release polymers are selected from the group consisting of POLYOX® (poly(ethylene oxide), POLYOX® N60K grade, Kollidon® SR, HPMC, HPMC (high viscosity), HPC, HPC (high viscosity), and Carbopol®.

In certain embodiments, extended/controlled release coating are selected from a group of ethylcellulose polymers, such as ETHOCEL™ and Surelease® Aqueous Ethylcellulose Dispersions.

In certain embodiments, antioxidants are selected from a group consisting of butylated hydroxyanisole (BHA), butylated hydroxytoluene (BHT), sodium ascorbate, and α-tocopherol.

In certain embodiments, tablet coatings are selected from the group of Opadry® 200, Opadry® II, Opadry® fx, Opadry® amb, Opaglos® 2, Opadry® tm, Opadry®, Opadry® NS, Opalux®, Opatint®, Opaspray®, Nutraficient®.

Preferred unit dosage formulations are those containing an effective dose, as herein below recited, or an appropriate fraction thereof, of the active ingredient.

Compounds may be administered orally at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Indications

Disclosed herein are methods of treating a VMAT2-mediated disorder comprising administering to a subject having or suspected of having such a disorder, a therapeutically effective amount of a compound or composition as disclosed herein or a pharmaceutically acceptable salt, solvate, or prodrug thereof.

VMAT2-mediated disorders, include, but are not limited to, chronic hyperkinetic movement disorders, Huntington's disease, hemiballismus, senile chorea, tic disorders, tardive dyskinesia, dystonia, Tourette's syndrome, depression, cancer, rheumatoid arthritis, psychosis, multiple sclerosis, asthma, and/or any disorder which can lessened, alleviated, or prevented by administering a VMAT2 inhibitor.

In certain embodiments, a method of treating a VMAT2-mediated disorder comprises administering to the subject a therapeutically effective amount of a compound or composition as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome $P_{450}$ or monoamine oxidase isoform in the subject; (4) decreased metabolism via at least one polymorphically-expressed cytochrome $P_{450}$ isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described by Li et al. *Rapid Communications in Mass Spectrometry* 2005, 19, 1943-1950; Jindal, et al., *Journal of Chromatography, Biomedical Applications* 1989, 493(2), 392-7; Schwartz, et al., *Biochemical Pharmacology* 1966, 15(5), 645-55; Mehvar, et al., *Drug Metabolism and Disposition* 1987, 15(2), 250-5; Roberts et al., *Journal of Chromatography, Biomedical Applications* 1981, 226(1), 175-82; and any references cited therein or any modifications made thereof.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al. (*British Journal of Clinical Pharmacology*, 2000, 49, 343-351). The inhibition of the $MAO_A$ isoform is measured by the method of Weyler et al. (*J. Biol Chem.* 1985, 260, 13199-13207). The inhibition of the $MAO_B$ isoform is measured by the method of Uebelhack et al. (*Pharmacopsychiatry*, 1998, 31, 187-192).

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to, change from baseline in the chorea score of the Unified Huntington's Disease Rating Scale (UH-DRS).

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of VMAT2-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more anti-psychotics, including, but not limited to, chlorpromazine, levomepromazine, promazine, acepromazine, triflupromazine, cyamemazine, chlorproethazine, dixyrazine, fluphenazine, perphenazine, prochlorperazine, thiopropazate, trifluoperazine, acetophenazine, thioproperazine, butaperazine, perazine, periciazine, thioridazine, mesoridazine, pipotiazine, haloperidol, trifluperidol, melperone, moperone, pipamperone, bromperidol, benperidol, droperidol, fluanisone, oxypertine, molindone, sertindole, ziprasidone, flupentixol, clopenthixol, chlorprothixene, thiothixene, zuclopenthixol, fluspirilene, pimozide, penfluridol, loxapine, clozapine, olanzapine, quetiapine, tetrabenazine, sulpiride, sultopride, tiapride, remoxipride, amisulpride, veralipride, levosulpiride, lithium, prothipendyl, risperidone, clotiapine, mosapramine, zotepine, pripiprazole, and paliperidone.

In certain embodiments, the compounds disclosed herein can be combined with one or more benzodiazepines ("minor tranquilizers"), including, but not limited to alprazolam, adinazolam, bromazepam, camazepam, clobazam, clonazepam, clotiazepam, cloxazolam, diazepam, ethyl loflazepate, estizolam, fludiazepam, flunitrazepam, halazepam, ketazolam, lorazepam, medazepam, dazolam, nitrazepam, nordazepam, oxazepam, potassium clorazepate, pinazepam, prazepam, tofisopam, triazolam, temazepam, and chlordiazepoxide.

In certain embodiments, the compounds disclosed herein can be combined with olanzapine or pimozide.

The compounds disclosed herein can also be administered in combination with other classes of compounds, including, but not limited to, anti-retroviral agents; CYP3A inhibitors; CYP3A inducers; protease inhibitors; adrenergic agonists; anti-cholinergics; mast cell stabilizers; xanthines; leukotriene antagonists; glucocorticoids treatments; local or general anesthetics; non-steroidal anti-inflammatory agents (NSAIDs), such as naproxen; antibacterial agents, such as amoxicillin; cholesteryl ester transfer protein (CETP) inhibitors, such as anacetrapib; anti-fungal agents, such as isoconazole; sepsis treatments, such as drotrecogin-α; steroidals, such as hydrocortisone; local or general anesthetics, such as ketamine; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothiazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporine; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating VMAT2-mediated disorders in a subject in need of such treatment comprising administering to said subject an amount of a compound disclosed herein effective to reduce or prevent said disorder in the subject, in combination with at least one additional agent for the treatment of said disorder. In a related aspect, certain embodiments provide therapeutic compositions comprising at least one compound disclosed herein in combination with one or more additional agents for the treatment of VMAT2-mediated disorders.

General Synthetic Methods for Preparing Compounds

The compounds as disclosed herein can be prepared by methods known to one of skill in the art and routine modifications thereof, and/or following procedures similar to those described in US 20100130480 (paragraphs [0093]-[0121]), US 20120003330 (paragraphs [0104]-[0162]), WO 2005077946; WO 2008/058261; EP 1716145; Lee et al., *J. Med. Chem.*, 1996, (39), 191-196; Kilbourn et al., *Chirality*, 1997, (9), 59-62; Boldt et al., *Synth. Commun.*, 2009, (39), 3574-3585; Rishel et al., *J. Org. Chem.*, 2009, (74), 4001-4004; DaSilva et al., *Appl. Radiat. Isot.*, 1993, 44(4), 673-676; Popp et al., *J. Pharm. Sci.*, 1978, 67(6), 871-873; Ivanov et al., *Heterocycles* 2001, 55(8), 1569-1572; U.S. Pat. No. 2,830,993; U.S. Pat. No. 3,045,021; WO 2007130365; WO 2008058261, which are hereby incorporated in their entirety, and references cited therein and routine modifications thereof.

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

In certain embodiments, specific examples of compounds of the present invention include a compound selected from the list described in paragraph [0122] of US 20100130480 and paragraph [0163] of US 20120003330, which are hereby incorporated by reference.

Changes in the in vitro metabolic properties of certain of the compounds disclosed herein as compared to their non-isotopically enriched analogs and methods of determining such changes have been described in paragraph [0125] of US 20100130480 and paragraphs [0165]-[0185] of US 20120003330, which are hereby incorporated by reference.

The invention is further illustrated by the following examples.

FORMULATION EXAMPLES

Examples 1-5, and other Examples described herein, may be made by the methods disclosed in FIG. 1.

Example 1

15 mg $d_6$-Tetrabenazine Gastro-Erosional Extended Release (Small Tablet)

Formulation A

Table 1 below discloses the elements of a 350 mg total weight gastro-erosional granulation formulation tablet comprising 15 mg (RR, SS)-1,3,4,6,7,11b-hexahydro-9,10-di(methoxy-$d_3$)-3-(2-methylpropyl)-2H-benzo[a]quinolizin-2-one.

TABLE 1

| Material | mg/tab | % |
| --- | --- | --- |
| $d_6$-Tetrabenazine (milled) | 15.0 | 4.3 |
| Mannitol Powder | 185.4 | 53.0 |
| Microcrystalline Cellulose | 61.8 | 17.7 |
| PVP K29/32 | 14.0 | 4.0 |
| Tween 80 (Polysorbate 80) | 3.8 | 1.1 |
| Mannogem ® EZ (spray dried mannitol) | 31.5 | 9.0 |
| POLYOX ® N60K | 35.0 | 10.0 |
| Magnesium Stearate | 3.5 | 1.0 |
| Totals: | 350.0 | 100.0 |

$d_6$-Tetrabenazine (milled) is combined along with Mannitol Powder, Microcrystalline Cellulose, PVP K29/32 and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol and POLYOX® N60K into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 350 mg.

Example 2

7.5 mg $d_6$-Tetrabenazine Gastro-Erosional Extended Release (Small Tablet)

Formulation A

Table 2 below discloses the elements of a 350 mg total weight gastro-erosional granulation formulation tablet comprising 7.5 mg $d_6$-tetrabenazine.

TABLE 2

| Material | mg/tab | % |
| --- | --- | --- |
| $d_6$-Tetrabenazine (milled) | 7.5 | 2.1 |
| Mannitol Powder | 191.0 | 54.6 |
| Microcrystalline Cellulose | 63.7 | 18.2 |
| PVP K29/32 | 14.0 | 4.0 |
| Tween 80 (Polysorbate 80) | 3.8 | 1.1 |
| Mannogem EZ (spray dried mannitol) | 31.5 | 9.0 |
| POLYOX ® N60K | 35.0 | 10.0 |
| Magnesium Stearate | 3.5 | 1.0 |
| Totals: | 350.0 | 100.0 |

Same process as described for Example 1.

Example 3

15 mg $d_6$-Tetrabenazine Gastro-Retentive Extended Release (Large Tablet)

Formulation B

Figure 2:
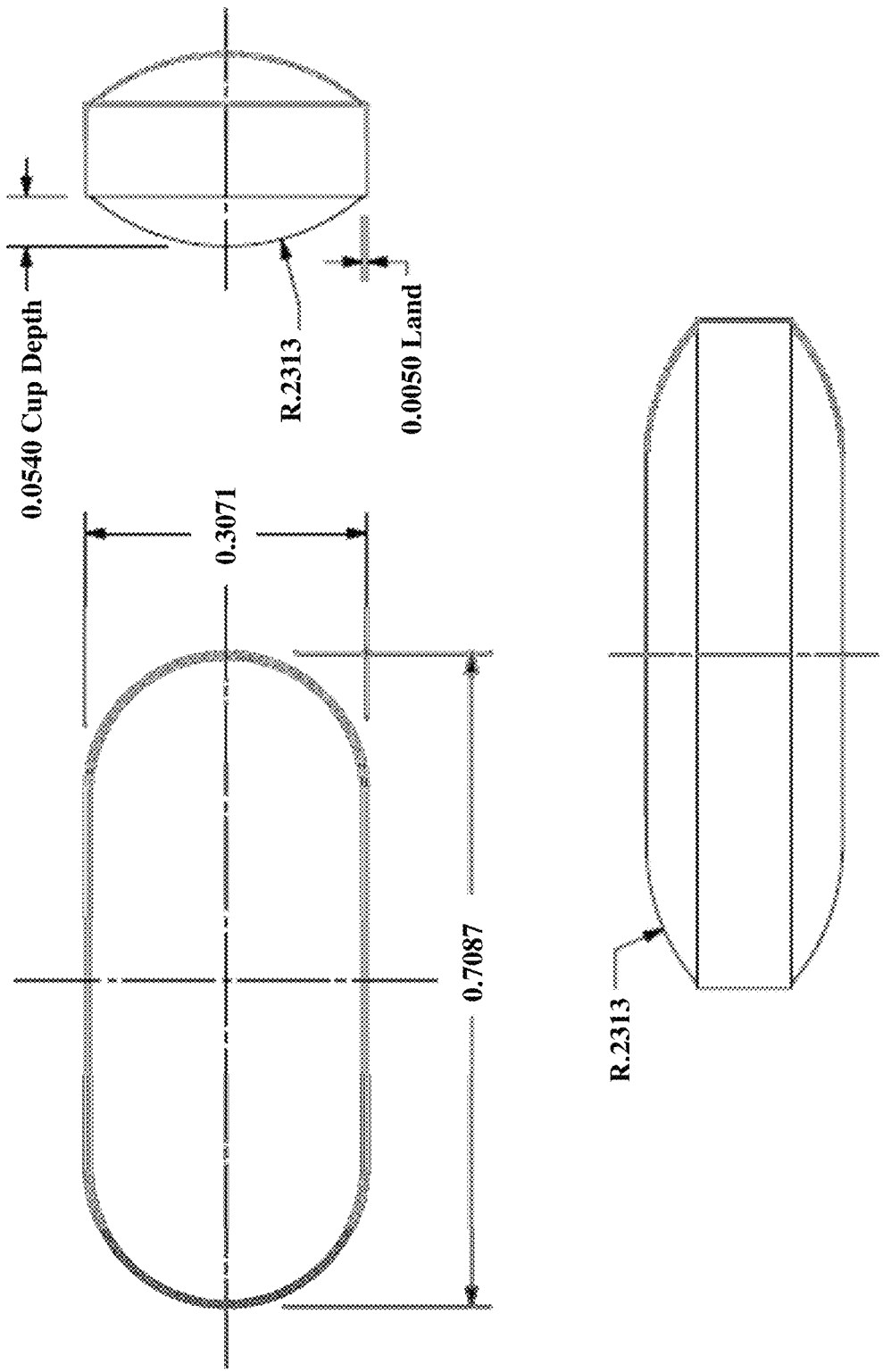
FIG. 2: Dimensions of Gastro-Retentive Extended Release Large Tablet.

Table 3 below discloses the elements of a 700 mg total weight gastro-retentive formulation tablet comprising 15 mg $d_6$-tetrabenazine. The gastro-retentive tablet is an elongated capsule having dimensions of approximately 0.7087 in. long by 0.3071 in. wide, having rounded ends with a cup depth of 0.0540 in. on each opposing side, as shown in FIG. 2.

TABLE 3

| Material | mg/tab | % |
| --- | --- | --- |
| $d_6$-Tetrabenazine (milled) | 15.0 | 2.1 |
| Mannitol Powder | 357.5 | 51.1 |
| Microcrystalline Cellulose | 119.0 | 17.0 |
| PVP K29/32 | 26.0 | 3.7 |
| Tween 80 (Polysorbate 80) | 7.5 | 1.1 |
| Mannogem EZ (spray dried mannitol) | 45.5 | 6.5 |
| POLYOX ® N60K | 122.5 | 17.5 |
| Magnesium Stearate | 7.0 | 1.0 |
| Totals: | 700.0 | 100.0 |

Same Process as described for Example 1. But theoretical compression weight is 700 mg.

Example 4

7.5 mg $d_6$-Tetrabenazine Gastro-Retentive Extended Release (Large Tablet)

Formulation B

Table 4 below discloses the elements of a 700 mg total weight gastro-retentive formulation tablet comprising 7.5 mg $d_6$-tetrabenazine. The gastro-retentive tablet is an elongated capsule having dimensions of approximately 0.7087 in. long by 0.3071 in. wide, having rounded ends with a cup depth of 0.0540 in. on each opposing side, as shown in FIG. 2.

TABLE 4

| Material | mg/tab | % |
| --- | --- | --- |
| $d_6$-Tetrabenazine (milled) | 7.5 | 1.1 |
| Mannitol Powder | 363.0 | 51.9 |
| Microcrystalline Cellulose | 121.0 | 17.3 |
| PVP K29/32 | 26.0 | 3.7 |
| Tween 80 (Polysorbate 80) | 7.5 | 1.1 |
| Mannogem ® EZ (spray dried mannitol) | 45.5 | 6.5 |
| POLYOX ® N60K | 122.5 | 17.5 |
| Magnesium Stearate | 7.0 | 1.0 |
| Totals: | 700.0 | 100.0 |

Same Process as described for Example 1. But theoretical compression weight is 700 mg.

Example 5

6 mg $d_6$-Tetrabenazine Immediate Release Tablet

Table 5 below discloses the elements of a 125 mg total weight immediate-release tablet comprising 6 mg $d_6$-tetrabenazine.

TABLE 5

| Material | mg/tab | % |
| --- | --- | --- |
| $d_6$-Tetrabenazine (milled) | 6.0 | 4.8 |
| Mannitol Powder | 75.0 | 60.0 |
| Microcrystalline Cellulose | 25.0 | 20.0 |
| Sodium Starch Glycolate | 2.5 | 2.0 |
| PVP K29/32 | 6.0 | 4.8 |
| Tween 80 (Polysorbate 80) | 1.0 | 0.8 |
| Mannogem ® EZ (spray dried mannitol) | 5.8 | 4.6 |
| Sodium Starch Glycolate | 2.5 | 2.0 |
| Magnesium Stearate | 1.2 | 1.0 |
| Totals: | 125.0 | 100.0 |

$d_6$-Tetrabenazine (milled) is combined along with Mannitol Powder, Microcrystalline Cellulose, Sodium Starch Glycolate, PVP K29/32 and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol and Sodium Starch Glycolate into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 125 mg.

Examples 6-8

6 mg, 12 mg, and 18 mg $d_6$-Tetrabenazine Gastro-Erosional Extended Release (Small Tablet)

Table 6 discloses additional strengths of the sustained release 350 mg tablet formulation containing anti-oxidants and an aqueous film coating.

TABLE 6

| Material | mg/tab | % | mg/tab | % | mg/tab | % |
|---|---|---|---|---|---|---|
| $d_6$-Tetrabenazine (milled) | 6.0 | 1.7 | 12.0 | 3.4 | 18.0 | 5.1 |
| Mannitol Powder | 191.3 | 54.7 | 186.9 | 53.4 | 180.5 | 51.6 |
| Microcrystalline Cellulose | 64.2 | 18.3 | 62.6 | 17.9 | 63.0 | 18.0 |
| PVP K29/32 | 14.0 | 4.0 | 14.0 | 4.0 | 14.0 | 4.0 |
| BHA | 0.5 | 0.1 | 0.5 | 0.1 | 0.5 | 0.1 |
| Tween 80 (Polysorbate 80) | 4.0 | 1.1 | 4.0 | 1.1 | 4.0 | 1.1 |
| Mannogem ® EZ (spray dried mannitol) | 31.1 | 8.9 | 31.1 | 8.9 | 31.1 | 8.9 |
| POLYOX ® N60K | 35.0 | 10.0 | 35.0 | 10.0 | 35.0 | 10.0 |
| BHT | 0.4 | 0.1 | 0.4 | 0.1 | 0.4 | 0.1 |
| Magnesium Stearate | 3.5 | 1.0 | 3.5 | 1.0 | 3.5 | 1.0 |
| Totals: | 350.0 | 100.0 | 350.0 | 100.0 | 350.0 | 100.0 |
| Core Tablets: | 350.0 | 97.1 | 350.0 | 97.1 | 350.0 | 97.1 |
| Opadry II 85F184 22 White | 10.5 | 2.9 | 10.5 | 2.9 | 10.5 | 2.9 |
| Totals (Coated Tablets): | 360.5 | 100.0 | 360.5 | 100.0 | 360.5 | 100.0 |

$d_6$-Tetrabenazine (milled) is combined along with Mannitol Powder, Microcrystalline Cellulose, PVP K29/32, BHA and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol, BHT and POLYOX® N60K into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 350 mg. The tablet cores are then placed into a side vented, fully perforated coating pan where they are coated with a 20% solids dispersion of Opadry® II 85F18422 White in Water until a theoretical weight gain of 3% is obtained.

The following examples may be made with varying amounts of $d_6$-tetrabenazine, and increasing proportionally the amount of filler material. Those skilled in the art will easily be able to vary the proportions of glidants, fillers/diluents, binders, disintegrants, and other ingredients in order to optimize the formulation and its method of manufacture.

Example 9

$d_6$-Tetrabenazine 50 mg Tablets $d_6$-Tetrabenazine tablets of total individual weights of 250 mg and containing 25 mg of $d_6$-tetrabenazine are prepared according to the dry granulation method set out below. The tablets all contain $d_6$-tetrabenazine and other excipients in a matrix containing the release retarding agent hydroxypropylmethylcellulose.

Three different formulations are employed, each differing only with respect to the grade of hydroxypropylmethylcellulose used. The three grades are (a) HPMC (K4M), (b) HPMC (K100 LV) and (c) HPMC (E15LV), the properties of each of which are set out above.

TABLE 7

| Ingredient | Function | 250 mg tablet |
|---|---|---|
| $d_6$-Tetrabenazine | Active agent | 25 mg, 20% (w/w) |
| Lactose | Diluent | 103.9 mg, 31.6% (w/w) |
| Starch | Binder/Disintegrant | 40.5 mg, 16.2% (w/w) |
| (a) HPMC (K4M); or (b) HPMC (K100 LV); or (c) HPMC (E15LV) | Controlled-release agent | 75 mg, 30% (w/w) |
| Talc | Glidant | 4 mg, 1.6% (w/w) |

$d_6$-Tetrabenazine, lactose, starch and the chosen grade of HPMC are sifted through a 30 mesh hand sieve into a suitable container. The powders are then mixed in a Hobart mixer for 10 minutes with the kneader forward on slow speed. The talc is transferred through a 30 mesh hand sieve and into a suitable container and the magnesium stearate was transferred and sifted through a 60 mesh hand sieve into a suitable container. The sifted talc and magnesium stearate is added to $d_6$-tetrabenazine, lactose, starch and HPMC in the Hobart mixer and all ingredients are mixed for 2 minutes with the kneader forward on slow speed to form the granulate. The granulate blend is then scaled in polyethylene containers that have been double lined with polyethylene bags. The 250 mg tablets are formed by compression using an 8 mm round, flat, beveled edge punch with a single break line for both the upper and lower punches. The compressed 250 mg tablets are packed into 85 ml HDPE bottles with inner polypropylene caps containing a liner consisting of Suryln/aluminum/polyethylene/bleached kraft membrane.

Example 10

Preparation of Tablets Containing 25 Mg $d_6$-Tetrabenazine in a Matrix Including Polyethylene Oxide and Hydroxypropylmethylcellulose and Polyoxyalkylene Block Copolymer For the manufacture of a 4 kg batch of 25 mg $d_6$-tetrabenazine tablets, half the required amount of microcrystalline cellulose, half the required amount of lactose, half the required amount of polyethylene oxide (PEO), half the required amount of hydroxypropylmethylcellulose (HPMC) and half the required amount of polyoxyalkylene block copolymer (Pluronic®) are filled into a Pharmatech AB-050 V Shell blender. Subsequently, $d_6$-tetrabenazine, with the remaining microcrystalline cellulose, lactose, PEO, HPMC and Pluronic® are added to the Blender. The blend is then mixed at 25 rpm for 10 minutes without the use of an intensifier bar. Following the 10 minutes blending, the magnesium stearate is added to the blend, and the blend further tumbled in the V Blender for one minute at 25 rpm without the use of the intensifier. The tablet blend is discharged from the V Blender and compressed into tablets using a Riva Pi colla Rotary tablet press model B/10 fitted with 17 mm×9 mm caplet tooling. Compression parameters are adjusted in order to achieve a tablet weight of 650 mg and hardness of 80-120N.

Example 11

Preparation of Tablets Containing $d_6$-Tetrabenazine in a Matrix Including Polyethylene Oxide and Hydroxypropylmethylcellulose and Polyoxyalkylene Block Copolymer PVA Granulation Method A. Preparation of $d_6$-tetrabenazine Granules In an alternative to the procedure described in Example 10, $d_6$-tetrabenazine is granulated prior to mixing with other tablet excipients, in order to improve powder flow during compression. Granulation can be achieved through either wet or dry granulation. In one embodiment of the invention, in order to manufacture a 30 kg batch of 50 mg $d_6$-tetrabenazine tablets, $d_6$-tetrabenazine is first wet granulated with lactose and polyvinyl alcohol (PVA) as a binder in an Aeromatic Fielder MP3/2/3 fluidized bed granulator. In brief, the granulation binder solution is prepared by dispersing the PVA in cold water which is subsequently heated to approximately 60° C. to solubilize the PVA. The solution is then allowed to cool for at least 2 hours. The granulation solution is then top-sprayed onto an 18 kg fluidized bed of $d_6$-tetrabenazine and lactose (58.41:41.59 ratio of lactose: $d_6$-tetrabenazine), fluidized in an Aeromatic Fielder MP3/2/3 fluidized bed granulator with the following process conditions:

TABLE 8

| Process Parameter | Setting |
| --- | --- |
| Product Temperature | 25-26° C. |
| Inlet Air Temperature | 65° C. |
| Air velocity | 250 m3/h |
| Atomising Air Pressure | 1 bar |
| Spray Rate | 70 g/min |

Following application of 252 g of PVA to the fluidized bed, spraying is stopped and the granules further fluidized to dry the granulates to a moisture content of approximately 1.5% w/w.

B. Preparation of Tablets Containing $d_6$-Tetrabenazine

To blend the $d_6$-tetrabenazine granules with the other tablet excipients, half the required amount of microcrystalline cellulose, half the required amount of lactose, half the required amount of PEO, half the required amount of HPMC and half the required amount of the Pluronic® are filled into a Pharmatech AB-400 V Shell blender. Subsequently, the $d_6$-tetrabenazine granules, with the remaining microcrystalline cellulose, lactose, PEO, HPMC and Pluronic® are added to the Blender. The 30 kg blend is then mixed at 25 rpm for 10 minutes without the use of an intensifier bar. Following the 10 minutes blending, the magnesium stearate is added to the blend, and the blend further tumbled in the V Blender for one minute at 25 rpm without the use of the intensifier. The tablet blend is discharged from the V Blender and compressed into tablets using a Fette 1200 tablet press fitted with 17 mm×9 mm caplet tooling. Compression parameters are adjusted in order to achieve a tablet weight of 650 mg and hardness of 80-120 N.

Example 12

Preparation of Tablets Containing a $d_6$-Tetrabenazine: Eudragit® E Extrudate

A. Manufacture of 30:70 $d_6$-Tetrabenazine:Eudragit® E Extrudate

Each heating zone of an APV Baker 19 mm twin-screw extruder is heated to a target temperature of 70° C., 140° C., 140° C., 130° C., and 100° C. for each of heating zones 1, 2, 3, 4 and 5 respectively. The extruder twin screws are then rotated at 140 rpm and a 4.6 kg blend of $d_6$-tetrabenazine and Eudragit® E, preblended in a Pharmatech AB-050 V blender for 5 minutes, is fed into the extruder hopper until all five heating zone temperatures are within 5° C. of the target temperature. Extrusion of the blend is continued at 140 rpm and milled extrudate is collected on a stainless steel tray.

B. Preparation of Tablets Containing the Extrudate

In order to manufacture a 4 kg batch of 50 mg $d_6$-tetrabenazine tablets including the melt extrusion of (A) above, half the required amount of microcrystalline cellulose, half the required amount of lactose, half the required amount of PEO, half the required amount of HPMC and half the required amount of Pluronic® are filled into a Pharmatech AB-050 V Shell blender. Subsequently, $d_6$-tetrabenazine extrudate, with the remaining microcrystalline cellulose, lactose, PEO, HPMC and Pluronic® are added to the blender. The blend is then mixed at 25 rpm for 10 minutes without the use of an intensifier bar. Following the 10 minutes blending, the magnesium stearate is added to the blend, and the blend is further tumbled in the V Blender for one minute at 25 rpm without the use of the intensifier. The tablet blend is discharged from the V Blender and compressed into tablets using a Riva Pi colla Rotary tablet press model B/10 fitted with 17 mm×9 mm caplet tooling. Compression parameters are adjusted in order to achieve a tablet weight of 650 mg and hardness of 80-120 N.

Example 13

The Formulations of Examples 13A to 13C in the Table Below May be Prepared by the Method Described in Example 11

Example 13A is a 650 mg 17 mm×9 mm tablet matrix formulation hardness 60-80N) including 50 mg $d_6$-tetrabenazine, 10% w/w 5,000,000 MW Polyethylene oxide (PEO WSR Coag.), 10% w/w 4,000 cps HPMC (Methocel K4M) together with 20% polyoxyalkylene block copolymer (Pluronic® F127) as a drug release modifier.

Example 13B is a tablet identical in size and shape and hardness to 5 A, has the same levels of K4M and PEO WSR Coag., but differs in that the Pluronic® F127 is replaced with lactose as a drug release modifier.

Example 13C is a tablet identical in size and shape and hardness to 5A, has the same levels of Methocel K4M and PEO WSR Coag, but differs from both 5A and 5B in that both Pluronic® F127 and lactose are present in the formulation.

The ingredients of the formulations of each of Examples 13A to 13C are set out in the table below as percentages.

TABLE 9

| Components of Tablet Formulation | Example 13A | Example 13B | Example 13C |
| --- | --- | --- | --- |
| $d_6$-Tetrabenazine | 7.7 | 7.7 | 7.7 |
| PEO WSR Coagulant | 10 | 10 | 10 |

TABLE 9-continued

| Components of Tablet Formulation | Example 13A | Example 13B | Example 13C |
|---|---|---|---|
| HPMC K4M | 10 | 10 | 10 |
| Lactose monohydrate | — | 35.7 | 25.65 |
| Microcrystalline Cellulose | 51.3 | 35.7 | 25.65 |
| Magnesium Stearate | 1 | 1 | 1 |
| Pluronic ® F127 | 20 | — | 20 |
| TOTAL | 100 | 100 | 100 |

Example 14

Examples 14A and 14B are Similar to Those Presented in Example 13, but Use a Higher Viscosity Grade of HPMC (100,000 cps)

TABLE 10

| Components of Tablet Formulation | Example 14A | Example 14B |
|---|---|---|
| $d_6$-Tetrabenazine | 7.7 | 7.7 |
| PEO WSR Coagulant | 10 | 10 |
| HPMC K4M | 10 | 10 |
| Lactose monohydrate | 25.65 | — |
| Microcrystalline Cellulose | 25.65 | 71.3 |
| Magnesium Stearate | 1 | 1 |
| Pluronic ® F127 | 20 | — |
| TOTAL | 100 | 100 |

Example 15

The following tables provide examples of formulations of different drug potency including $d_6$-tetrabenazine and Pluronic®. The formulations shown below may be prepared by first granulating the drug with a binder (in this case polyvinyl alcohol) to aid powder flow during compression.

TABLE 11

| Components of Tablet | 3.125 mg | | 6.25 mg | | 12.5 mg | |
|---|---|---|---|---|---|---|
| Formulation | mg | % | mg | % | mg | % |
| $d_6$-Tetrabenazine | 3.125 | 0.48 | 6.25 | 0.96 | 12.5 | 1.92 |
| Polyethylene Oxide | 65 | 10 | 65 | 10 | 65 | 10 |
| Hypomellose | 65 | 10 | 65 | 10 | 65 | 10 |
| Pluronic ® F127 | 130 | 20 | 130 | 20 | 130 | 20 |
| Microcrystalline Cellulose | 191.3 | 29.43 | 188.24 | 28.96 | 184.79 | 28.43 |
| Lactose monohydrate | 191.3 | 29.43 | 188.3 | 28.96 | 184.79 | 28.43 |
| Polyvinyl Alcohol | 0.71 | 0.11 | 0.71 | 0.11 | 1.42 | 0.22 |
| Magnesium Stearate | 6.5 | 1 | 6.5 | 1 | 6.5 | 1 |
| TOTAL | 650 | 100 | 650 | 100 | 650 | 100 |

TABLE 12

| Components of Tablet | 50 mg | | 37.5 mg | | 50 mg | |
|---|---|---|---|---|---|---|
| Formulation | mg | % | Mg | % | Mg | % |
| $d_6$-Tetrabenazine | 25 | 3.85 | 37.5 | 5.77 | 50 | 7.69 |
| Polyethylene Oxide | 65 | 10 | 65 | 10 | 65 | 10 |
| Hypomellose | 65 | 10 | 65 | 10 | 65 | 10 |
| Pluronic ® F127 | 130 | 20 | 130 | 20 | 130 | 20 |
| Microcrystalline Cellulose | 178.5 | 27.5 | 171.8 | 26.4 | 165.9 | 25.5 |
| Lactose monohydrate | 178.5 | 27.5 | 171.8 | 26.4 | 165.9 | 25.5 |
| Polyvinyl Alcohol | 1.68 | 0.26 | 2.52 | 0.39 | 1.68 | 0.26 |
| Magnesium Stearate | 6.5 | 1 | 6.5 | 1 | 7 | 1 |
| TOTAL | 650 | 100 | 650 | 100 | 700 | 100 |

Example 16

Gastric Retentive Formulations

The following table sets out some examples of gastric retentive formulations according to the present invention. The following formulations are of different drug potency and may be made by direct compression, i.e. in the absence of polyvinyl alcohol. The skilled person will appreciate that the formulations set out below will demonstrate that the rate and extent of drug dissolution is independent of drug potency in the formulation.

TABLE 13

| Components of Tablet | 3.125 mg | | 6.25 mg | | 12.5 mg | |
|---|---|---|---|---|---|---|
| Formulation | mg | % | mg | % | mg | % |
| $d_6$-Tetrabenazine | 3.125 | 0.48 | 6.25 | 0.96 | 12.5 | 1.93 |
| PEO Coagulant | 65 | 10 | 65 | 10 | 65 | 10 |
| HPMC K15M | 65 | 10 | 65 | 10 | 65 | 10 |
| Pluronic ® F127 | 130 | 20 | 130 | 20 | 130 | 20 |
| Microcrystalline Cellulose | 188.95 | 29.07 | 186.21 | 28.65 | 180.04 | 27.7 |
| Lactose monohydrate | 191.4 | 29.44 | 192.1 | 29.55 | 191.0 | 29.38 |
| Magnesium Stearate | 6.5 | 1 | 6.5 | 1 | 6.5 | 1 |
| TOTAL | 650 | 100 | 650 | 100 | 650 | 100 |

TABLE 14

| Components of Tablet | 25 mg | | 37.5 mg | | 50 mg | |
|---|---|---|---|---|---|---|
| Formulation | mg | % | mg | % | mg | % |
| $d_6$-Tetrabenazine | 25 | 3.85 | 37.5 | 5.77 | 50 | 7.15 |
| PEO Coagulant | 65 | 10 | 65 | 10 | 70 | 10 |
| HPMC K15M | 65 | 10 | 65 | 10 | 70 | 10 |

TABLE 14-continued

| Components of Tablet Formulation | 25 mg mg | 25 mg % | 37.5 mg mg | 37.5 mg % | 50 mg mg | 50 mg % |
|---|---|---|---|---|---|---|
| Pluronic ® F127 | 130 | 20 | 130 | 20 | 140 | 20 |
| Microcrystalline Cellulose | 167.56 | 25.78 | 155.53 | 23.93 | 158.2 | 22.6 |
| Lactose monohydrate | 178.44 | 27.45 | 190.47 | 29.30 | 204.79 | 22.26 |
| Magnesium Stearate | 6.5 | 1 | 6.5 | 1 | 7 | 1 |
| TOTAL | 650 | 100 | 650 | 100 | 700 | 100 |

Example 17

The Following Table Sets Out Some Examples of Formulations Containing Various Combinations of $d_6$-Tetrabenazine, PEO, HPMC and Poloxamer

TABLE 15

| Components of Tablet Formulation % w/w of 650 mg tablet | A | B | C | D | E | F | G |
|---|---|---|---|---|---|---|---|
| $d_6$-Tetrabenazine | 7.7 | 7.7 | 7.7 | 7.7 | 7.7 | 7.7 | 7.7 |
| PEO WSR N-60K | — | 20 | — | — | — | 15 | — |
| PEO WSR Coagulant | 10 | — | 15 | 10 | 10 | 10 | 30 |
| Methocel K100M | — | — | 15 | 15 | 10 | — | — |
| Methocel K15M | — | — | — | — | — | — | 10 |
| Methocel K4M | 10 | 20 | — | — | — | 15 | — |
| Pluronic ® F68 | — | — | — | 7.7 | 20.5 | — | — |
| Pluronic ® F127 | — | 20 | 20 | — | — | 10 | 20 |
| Avicel ® pH 101 | 51.3 | 15.65 | 20.65 | 58.6 | 63.5 | 41.3 | 15.65 |
| Lactose monohydrate | — | 15.65 | 20.65 | — | — | — | 15.65 |
| Magnesium Stearate | 1 | 1 | 1 | 1 | 1 | 1 | 1 |

Example 18

The Following Table Sets Out Some Examples of Tablet Formulation Containing $d_6$-Tetrabenazine:Eudragit® Melt Extrudates

TABLE 16

| Ingredient % w/w | A | B |
|---|---|---|
| $d_6$-Tetrabenazine/Eudragit ® E (30:70) extrudate | 25.6 | — |
| $d_6$-Tetrabenazine/Eudragit ® 40:60 extrudate | — | 19.25 |
| PEO WSR Coagulant | 10 | 10 |
| HPMC K4M | 10 | 10 |
| Lactose monohydrate | 26.7 | 29.9 |
| Microcrystalline Cellulose | 26.7 | 29.9 |
| Magnesium Stearate | 1 | 1 |

Example 19

The Following Table Sets Out Examples of Tablet Formulations Containing Granules Including $d_6$-Tetrabenazine and Hydroxymethyl Cellulose and Hydroxyethylcellulose $d_6$-Tetrabenazine is blended with Methocel K100LV CR Premium, Methocel K15M Premium, Natrosol250HHX and Flowlac in a Diosna P1-6 high shear mixer for approximately 5 minutes with the chopper motor set at approximately 600 rpm and the mixer motor set at approximately 400 rpm. The blend is granulated with 2-propanol for approximately 5 minutes and the granules are dried in a Casburt laminar flow drying oven at a temperature of 40° C. for 18 h and screened through a 800 μm screen. The granules and the Ethocel 100FP are blended in a V-type PK Blendmaster with a mixing time of approximately 5 minutes with set speeds for the blender shell and intensifier bar. Magnesium stearate is added to the blend and the mixture is further blended for approximately 1.5 min with set speed for the blender shell and the intensifier bar turned off. The blend is compressed into tablets.

TABLE 17

| Ingredient % w/w | A | B | C | D |
|---|---|---|---|---|
| $d_6$-Tetrabenazine | 25 | 25 | 25 | 25 |
| Methocel K100LV CR Premium (Hydroxypropylmethylcellulose) | 7.5 | 15 | — | — |
| Methocel K15M Premium (Hydroxypropylmethylcellulose) | 8 | — | 15 | 15 |
| Natrosol 250 HHX (Hydroxyethylcellulose) | 3.5 | 3.5 | 3.5 | 3.5 |
| Flowlac 100 (Lactose) | 50 | 50.5 | 50.5 | 50.5 |
| Poloxamer F127 (Surfactant) | — | — | — | 15 |
| Ethocel 100FP Premium (Ethylcellulose) | 5 | 5 | 5 | 5 |
| Magnesium Stearate | 1 | 1 | 1 | 1 |

Example 20

Unitary Osmotic System Formulation

To form the following unitary osmotic system formulation, all tablet ingredients are granulated except D-mannitol and lubricant. D-mannitol and lubricant are then added, and compressed using conventional means. The core is then coated with solution using the vented pan coating process, to form a semipermeable membrane around core.

TABLE 18

| Tablet Core Ingredients | % of Tablet |
|---|---|
| $d_6$-Tetrabenazine | 22 |
| Lactose | 42 |
| Colloidal Silicon Dioxide | 0.74 |
| Polyvinyl alcohol | 5.48 |
| D-Mannitol | 29.04 |
| Sodium Stearyl Fumarate | 0.74 |
| Semipermeable Membrane Ingredients | % of Coating |
| Cellulose Acetate | 45 |
| Hydroxypropyl Cellulose | 40 |
| Acetyl Triethyl Citrate | 5 |
| Sodium Chloride | 10 |
| Organic Solvents (evaporated in process) | — |

Example 21

Multiparticulate Osmotic System Formulation

To form the following multiparticulate osmotic system formulation, $d_6$-tetrabenazine micro sphere ingredients are blended under high shear and processed using Ceform™ processing technology. Microspheres are then placed in a Wurster-based fluidized bed coater and sustained release coating applied.

TABLE 19

| Microsphere Ingredients | % of Sphere |
|---|---|
| $d_6$-Tetrabenazine | 22 |
| Compritol ATO 888 | 35 |
| Fumaric acid (fine powder) | 8 |
| Gelucire 50/13 35 | 35 |

| Sustained Release Coating Ingredients | % of Coating |
|---|---|
| Ethyl Cellulose Prem. Std. 45 cps/10 cps 1:1 | 56 |
| Hydroxypropyl cellulose | 32 |
| Talc- micronized | 12 |
| Isopropranol/Acetone (evaporated in process) | — |

Example 22

Hydrophobic Core Controlled Release System (Lipid)

To form the following lipid-based hydrophobic core controlled release system, granulate of the drug, Lubritab, Fumaric Acid, HPMC and HPC are melted above 80 degrees C. in jacketed high shear mixer. The granulate is then congealed and screened/milled/sized; lubricant is then added and the mixture compressed into tablets. Finally, cosmetic coat is applied to tablets using a vented coating pan.

TABLE 20

| Mini-Tablet Core Ingredients | % of Tablet |
|---|---|
| $d_6$-Tetrabenazine | 25 |
| Hydrogenated Vegetable Oil (Lubritab) | 32.5 |
| Hyprocellulose K100LV | 18.5 |
| Hydroxypropyl cellulose | 18.5 |
| Fumaric Acid | 5 |
| Magnesium Stearate | 0.5 |

| Tablet Coating Ingredients | % of Coating |
|---|---|
| Opadry (Clear) 5% solution | 100 |
| Purified Water (evaporated in process) | — |

Example 23

Hydrophobic Core Controlled Release System (Wax)

To form the following wax-based hydrophobic core controlled release system, granulate the drug, carnauba wax, citric acid and stearyl alcohol are melted at 95-100 degrees C. in jacketed high shear mixer. The granulate is then congealed and screened/milled/sized; lubricant is then added and the mixture compressed into tablets. Finally, cosmetic coat is applied to tablets using a vented coating pan.

TABLE 21

| Tablet Core Ingredients | % of Tablet |
|---|---|
| $d_6$-Tetrabenazine | 29.35 |
| Carrauba Wax | 35.5 |
| Stearyl alcohol | 24.65 |
| Citric Acid | 10 |
| Magnesium Stearate | 0.5 |

| Tablet Coating Ingredients | % of Coating |
|---|---|
| Opadry (Clear) 5% solution | 100 |
| Purified Water (evaporated) | — |

Example 24

Hydrophobic Core Controlled Release System (Insoluble Polymer)

To form the following insoluble polymer-based hydrophobic core controlled release system, $d_6$-tetrabenazine and silicon dioxide are granulated using PVA solution in a fluid bed granulator using top-spray method. The granulate, ethyl cellulose, Ludipress, citric acid, and lubricant are then compressed into tablets using rotary compression.

TABLE 22

| Tablet Core Ingredients | % of Tablet |
|---|---|
| $d_6$-Tetrabenazine | 44 |
| Colloidal Silicon Dioxide | 0.74 |
| Polyvinyl alcohol | 19.48 |
| Ethyl Cellulose | 27 |
| Fumaric Acid | 5 |
| Ludipress | 3.04 |
| Sodium Stearyl Fumarate | 0.74 |

| Tablet Coating Ingredients | % of Coating |
|---|---|
| Opadry (Clear) 5% solution | 100 |
| Purified Water (evaporated) | — |

Example 25

Hydrophobic Coat (Lipid)

$d_6$-Tetrabenazine, citric acid and lactose are granulated with colloidal silicon dioxide using PVA solution, under top-spray fluid bed process. Lubricant is added to granulate and compress using conventional rotary process. Mini-tablets are then coated with molten lipid-based coating in Wurster fluid-bed processor outfitted with hot melt coating apparatus.

TABLE 23

| Mini-Tablet Core Ingredients | % of Tablet |
|---|---|
| $d_6$-Tetrabenazine | 38 |
| Lactose | 55.16 |
| Colloidal Silicon Dioxide | 0.96 |
| Polyvinyl alcohol | 4.92 |
| Citric Acid | 5 |
| Sodium Stearyl Fumarate | 0.96 |

| Mini-Tablet Coating Ingredients | % of Coating |
|---|---|
| Glyceryl monostearate | 72.25 |
| Polyethylene Glycol 8000 | 24.75 |

Example 26

Hydrophobic Coat (Wax)

$d_6$-Tetrabenazine and lactose are granulated with colloidal silicon dioxide using PVA solution, under top-spray fluid bed process. Lubricant is added to granulate and compress using conventional rotary process. Tablets are then coated with molten wax-based coating in Wurster fluid-bed processor outfitted with hot melt coating apparatus.

TABLE 24

| Mini-Tablet Core Ingredients | % of Tablet |
| --- | --- |
| $d_6$-Tetrabenazine | 53 |
| Lactose | 40.16 |
| Colloidal Silicon Dioxide | 0.96 |
| Polyvinyl alcohol | 4.92 |
| Sodium Stearyl Fumarate | 0.96 |

| Mini-Tablet Coating Ingredients | % of Coating |
| --- | --- |
| Hydrogenated Castor Oil (Castorwax) | 72.25 |
| Polyethylene Glycol 8000 | 24.75 |

Example 27

Hydrophobic Coat (Insoluble Polymer)

$d_6$-Tetrabenazine and lactose are granulated with colloidal silicon dioxide using PVA solution, under top-spray fluid bed process. Lubricant is added to granulate and compress using conventional rotary process. Tablets are then coated with solvent in Wurster fluid-bed processor outfitted with hot melt coating apparatus.

TABLE 25

| Tablet Core Ingredients | % of Tablet |
| --- | --- |
| $d_6$-Tetrabenazine | 53 |
| Lactose | 40.16 |
| Colloidal Silicon Dioxide | 0.96 |
| Polyvinyl alcohol | 4.92 |
| Sodium Stearyl Fumarate | 0.96 |

| Tablet Coating Ingredients | % of Coating |
| --- | --- |
| Ethylcellulose | 64.09 |
| Hydroxypropyl Cellulose | 26.82 |
| Dibutyl Sebacate | 9.09 |
| Isopropanol/Acetone (evaporated) | — |

Example 28

Hydrophilic Core (Swellable)

All tablet ingredients except Eudragit EC© and lubricant are granulated in top spray fluid bed granulator. Eudragit EC© and lubricant are then added and compressed into tablets using conventional means. Finally, cosmetic coat is applied to tablets using a vented coating pan.

TABLE 26

| Tablet Core Ingredients | % of Tablet |
| --- | --- |
| $d_6$-Tetrabenazine | 30.12 |
| Colloidal Silicon Dioxide | 0.66 |
| Polyvinyl alcohol | 4 |
| Hypromellose K100LV | 20 |
| Eudragit RL © powder | 44.26 |
| Sodium Stearyl Fumarate | 0.96 |

| Tablet Coating Ingredients | % of Coating |
| --- | --- |
| Opadry (Clear) 5% solution | 100 |
| Purified Water (evaporated) | — |

Example 29

Hydrophilic Core (Soluble Polymer)

All tablet ingredients except HPMC and lubricant are granulated in top spray fluid bed granulator. HPMC and lubricant are then added and compressed into tablets using conventional means. Finally, cosmetic coat is applied to tablets using a vented coating pan.

TABLE 27

| Tablet Core Ingredients | % of Tablet |
| --- | --- |
| $d_6$-Tetrabenazine | 30 |
| Colloidal Silicon Dioxide | 0.66 |
| Polyvinyl alcohol | 1 |
| Hydroxypropyl Methylcellulose | 57.38 |
| Ethyl cellulose | 10 |
| Sodium Stearyl Fumarate | 0.96 |

| Tablet Coating Ingredients | % of Coating |
| --- | --- |
| Opadry (Clear) 5% solution | 100 |
| Purified Water (evaporated) | — |

Example 30

Hydrophilic Coat (Swellable)

$d_6$-Tetrabenazine and fumaric acid with colloidal silicon dioxide are granulated using PVA solution, under the top-spray fluid bed process. Lubricant is added to granulate and compress using conventional rotary process. Coating is applied to tablets using vented coating pan.

TABLE 28

| Tablet Core Ingredients | % of Tablet |
| --- | --- |
| $d_6$-Tetrabenazine | 40.15 |
| Lactose | 48.01 |
| Colloidal Silicon Dioxide | 0.96 |
| Fumaric Acid | 5 |
| Polyvinyl alcohol | 4.92 |
| Sodium Stearyl Fumarate | 0.96 |

| Tablet Coating Ingredients | % of Coating |
| --- | --- |
| Eudragit RS © | 14 |
| Eudragit RL © | 56 |
| Acetyl Triethyl Citrate | 15 |
| Talc | 15 |
| Alcoholic/Acetone Solvents (evaporates) | — |

Example 31

Hydrophilic Coat (Soluble Polymer)

$d_6$-Tetrabenazine and lactose are granulated with colloidal silicon dioxide using PVA solution, under the top-spray fluid bed process. Lubricant is added to granulate and compress using conventional rotary process. A sufficient amount of aqueous coating is used to coat the tablets in a conventional vented coating pan to sustain drug release.

TABLE 29

| Tablet Core Ingredients | % of Tablet |
| --- | --- |
| $d_6$-Tetrabenazine | 36.16 |
| Lactose | 60 |
| Colloidal Silicon Dioxide | 0.96 |
| Polyvinyl alcohol | 1.92 |
| Sodium Stearyl Fumarate | 0.96 |

| Tablet Coating Ingredients | % of Coating |
| --- | --- |
| Hydroxymethyl Cellulose | 62 |
| Hydroxyethyl Cellulose | 38 |
| Water (evaporated) | — |

Example 32

$d_6$-Tetrabenazine AQ Coated Tablet $d_6$-Tetrabenazine, lactose, and citric acid are granulated with colloidal silicon dioxide using PVA solution, under the top-spray fluid bed process. Lubricant is added to granulate and compress using conventional rotary process. The tablet is then coated with an aqueous-based coating dispersion/suspension in conventional vented coating pan.

TABLE 30

| Tablet Core Ingredients | % of Tablet |
| --- | --- |
| $d_6$-Tetrabenazine | 23 |
| Lactose | 57.16 |
| Colloidal Silicon Dioxide | 0.96 |
| Polyvinyl alcohol | 4.92 |
| Kollidon CL | 8 |
| Citric Acid | 5 |
| Sodium Stearyl Fumarate | 0.96 |

| Tablet Coating Ingredients | % of Coating |
| --- | --- |
| Eudragit NE30D | 40.03 (as dry) |
| Hydroxypropyl Methylcellulose 6 cps | 23.01 |
| Polyethylene Glycol8000 | 11.26 |
| Talc 400 | 20.26 |
| Titanium dioxide | 4.31 |
| Simethicone | 1.13 |

Example 33

Delayed Release System (Reverse Enteric Coat, Hydrophillic Core)

$d_6$-Tetrabenazine is granulated with colloidal silicon dioxide using PVA solution, under top-spray fluid bed process. Hypromellose, Ludipress, and lubricant are added to the granulate and compressed using a conventional rotary process. Tablets are then coated with a reverse-enteric coating in conventional vented coating pan using an alcohol-based solution.

TABLE 31

| Tablet Core Ingredients | % of Tablet |
| --- | --- |
| $d_6$-Tetrabenazine | 60 |
| Colloidal Silicon Dioxide | 0.74 |
| Polyvinyl alcohol | 5 |
| Hypromellose | 30 |
| Ludipress | 3.52 |
| Sodium Stearyl Fumarate | 0.74 |

| Tablet Coating Ingredients | % of Coating |
| --- | --- |
| Eudragit E100 | 66.9 |
| Acetyl Triethyl Citrate | 10 |
| Talc 400 | 23.1 |

Example 34

$d_6$-Tetrabenazine Sustained-Release (SR) Formulations, 12.5 Mg and 25 Mg

Sustained-release (SR) formulation that uses multiparticulate to improve solubility/delivery of the drug, and these drug-loaded particles are incorporated and released from a matrix tablet system by a combination of gelation and erosion of tablet. Drug-loaded particles can be ceform, shearform, extrusion-spheronization beads, layered beads, or other multiparticulate technology.

Drug and microsphere excipients are blended, and the multiparticulates processed to encapsulate the drug. Multiparticulates are then blended with other tablet excipients and compressed by standard means into a tablet. For strengths of $d_6$-tetrabenazine at 12.5 mg (375 mg total tablet weight) & 25 mg (750 mg total tablet weight), tablet sizes are formulated to be dose-proportional.

TABLE 32

| Ceform Microsphere Ingredients | % of Spheres |
| --- | --- |
| $d_6$-Tetrabenazine | 24 |
| Precirol ATO 5 (glycerol palmitostearate) | 38 |
| Milled Gelucire 50/13 pellets (stearyl macrogoglycerides) | 38 |

| Tablet Excipients | % of Tablet |
| --- | --- |
| Drug-loaded CEFORM Microspheres | 30 |
| Polyox (polyethyleneoxide) WSRNF750 | 20 |
| Encompress (dibasic calcium phosphate dihydrate) | 49 |
| Magnesium Stearate | 1 |

Example 35

$d_6$-Tetrabenazine Controlled Release Formulations (7.5 mg, 12.5 mg, 15 mg and 25 mg)

$d_6$-Tetrabenazine, lactose DC, starch 1500 & HPMC (K100LV) are sieved via a 30 mesh screen (approximately 600 Micron) into suitable containers. The sieved powders are then blended in a suitable Mixer for 10 minutes at slow speed. The talc is sieved through a 30 mesh screen (approximately 600 Micron) and the magnesium stearate sieved through a 60 mesh screen (approximately 250 Micron). The talc and magnesium stearate are added to the mixer and blended for 2 minutes at slow speed. The powder blend is compressed on a rotary tab letting machine, using flat bevelled edge punches.

TABLE 33

| Ingredients % w/w | 25 mg | 12.5 mg | 15 mg | 7.5 mg |
| --- | --- | --- | --- | --- |
| $d_6$-Tetrabenazine | 20 | 10 | 12 | 6 |
| Lactose Monohydrate DC | 30.96 | 31.56 | 39.16 | 35.66 |

TABLE 33-continued

| Ingredients % w/w | 25 mg | 12.5 mg | 15 mg | 7.5 mg |
|---|---|---|---|---|
| Starch 1500 | 16.2 | 25.9 | 16.2 | 25.9 |
| Methocel K100LV | 30 | 30 | 30 | 30 |
| Aerosil 200 | 0.6 | 0.3 | 0.4 | 0.2 |
| Talc | 1.6 | 1.6 | 1.6 | 1.6 |
| Magnesium Stearate | 0.64 | 0.64 | 0.64 | 0.64 |

Example 36

Controlled-Release (CR) Drug Layered Bead (Multiparticulate) Examples, Solvent and Aqueous-Based 1. $d_6$-Tetrabenazine Sustained Release Capsules $d_6$-Tetrabenazine-loaded beads may be prepared from the following ingredients.

TABLE 34

| $d_6$-Tetrabenazine-loaded Beads | % w/w |
|---|---|
| $d_6$-Tetrabenazine | 10 |
| Hypromellose 2910 (6 cps) USP | 2 |
| Triacetin USP | 0.4 |
| Citric Acid | 0.6 |
| Sodium Lauryl Sulfate (SLS) | 0.4 |
| Sugar Spheres USP (20-25 mesh) | 86.4 |
| Water USP (evaporated) | — |

The coating composition containing the hypromellose, triacetin, citric acid, and sodium lauryl sulfate is prepared as a 10% aqueous suspension. The suspension is applied to sugar spheres using standard Wurster-based air suspension coating using conditions suitable for Hypromellose-based coating (inlet target 50-70° C.).

Compression of beads into tablets (either immediate release or SR matrix type tablets) is contemplated. $d_6$-tetrabenazine-loaded beads made by using layering technique on sugar spheres are preferred, but one can use drug-loaded granules, floatable particles, extruded/spheronized pellets, Ceform microspheres, or other multiparticulates for drug core component as well. The typical bead size is from about 2 millimeters to about 0.1 mm in diameter or longest dimension before coating. Solubizers and acids (or absence thereof) can also be used in the core or in the coating component of the drug-loaded beads.

Second-coated sustained release beads can be prepared from drug spheres having the following composition. The coating composition is prepared as a 15% alcohol/acetone solution that includes the two types of ethylcellulose, the hydroxypropyl cellulose, and the triethyl citrate. The solution is applied to $d_6$-tetrabenazine loaded sugar spheres using standard Wurster-based air suspension coating using conditions suitable for Ethocel-based coatings (inlet target 45-65° C.).

The functional coating polymers for SR coating can be solvent or aqueous-based, cellulosics, methacrylics, pH independent, or pH dependent in nature. In addition to polymer application on drug layered beads, $d_6$-tetrabenazine beads manufactured by extrusion/spheronization can also be used as a substrate.

TABLE 35

| Sustained Release (SR) $d_6$-Tetrabenazine Beads | % w/w |
|---|---|
| Tetrabezaine Loaded Sugar Spheres | 84.75 |
| Ethylcellulose Std 45 Premium NF | 6.58 |
| Ethylcellulose Std 10 Premium NF | 2.19 |
| Hydroxypropyl Cellulose NF | 4.38 |
| Triethyl Citrate NF | 2.1 |
| Ethanol/Acetone 40:60 (evaporated) | — |

Immediate Release Overcoated SR Tetrabenzaine Beads (Optional)

A final immediate release (IR) coating (identical to first coating described in (A) above but employed at a different coating percentage) is optionally applied to SR $d_6$-tetrabenazine spheres to provide a pulsed immediate release drug component. Percentage of dose from IR portion could be from 0-70%, 5-50%, or 10-30%. The $d_6$-tetrabenazine-loaded beads could also be supplied in a capsule containing both IR and SR beads in selected dosage fractions.

Capsule Filling of $d_6$-Tetrabenazine-Containing Beads (SR, SR/IR, IR)

The aqueous-based coated beads can then be filled into hard gelatin capsules of a suitable size. The capsule shell can be any pharmaceutically acceptable capsule shell but is preferably a hard gelatin capsule shell and is of suitable size for containing from about 5 mg to about 30 mg of $d_6$-tetrabenazine. Conventional machinery and technique are used in filling the capsule shells.

2. $d_6$-Tetrabenazine Aqueous-Based Sustained Release Capsules $d_6$-Tetrabenazine-loaded beads may be prepared as disclosed above.

Second-coated sustained release beads having the following composition can be prepared from drug spheres having the following composition.

TABLE 36

| $d_6$-Tetrabenazine-Loaded Beads | % w/w |
|---|---|
| Tetrabezaine Loaded Sugar Spheres | 82 |
| Eudragit NE30D (as dry weight) | 6.4 |
| Hypromellose 2910 6 cps NF | 2.6 |
| Talc | 9 |
| Purified Water (evaporated) | — |

The aqueous-based coating composition containing the Eudragit, hypomellose and talc can be prepared as a 20% aqueous dispersion. The dispersion can then applied to $d_6$-tetrabenazine loaded sugar spheres using standard Wurster-based air suspension coating and conditions suitable for Eudragit NE 30D-based coatings (product temperature target 25-35° C.). The functional coating polymers for SR coating can be solvent or aqueous-based, cellulosics, methacrylics, pH independent, or pH dependent in nature.

Immediate Release Overcoated SR Tetrabenzaine Beads (Optional)

A final immediate release (IR) coating (identical to first coating described in (A) above but employed at a different coating percentage) is optionally applied to SR $d_6$-tetrabenazine spheres to provide a pulsed immediate release drug component. Percentage of dose from IR portion could be from 0-70%, 5-50%, or 10-30%. The $d_6$-tetrabenazine-loaded beads could also be supplied in a capsule containing both IR and SR beads in selected dosage fractions.

Capsule Filling of $d_6$-Tetrabenazine-Containing Beads (SR, SR/IR, IR)

The aqueous-based coated beads can then be filled into hard gelatin capsules of a suitable size. The capsule shell can be any pharmaceutically acceptable capsule shell but is preferably a hard gelatin capsule shell and is of suitable size for containing from about 10 mg to about 60 mg of $d_6$-tetrabenazine. Conventional machinery and technique are used in filling the capsule shells.

Compression of beads into tablets (either immediate release or SR matrix type tablets) is also contemplated. $d_6$-tetrabenazine-loaded beads using layering technique on sugar spheres may be used, but one can alternatively use drug-loaded granules, floatable particles, extruded/spheronised pellets, Ceform microspheres, or other multiparticulates for drug core component as well. Typical bead size is from about 2 millimeters to about 0.1 mm in diameter or longest dimension before coating. Other solubizers and acids (or absence thereof) can also be used in the core or coating component of the drug-loaded beads.

Pharmacokinetic Studies
Immediate Release Formulations

A Phase 1 pharmacokinetic study was conducted in 24 healthy extensive and intermediate CYP2D6 metabolizer volunteers receiving oral 25 mg doses of $d_6$-tetrabenazine or tetrabenazine to compare the relative bioavailability and pharmacokinetics of single oral doses of $d_6$-tetrabenazine and its metabolites $d_6$-α-HTBZ and $d_6$-β-HTBZ with their non-deuterated equivalents (tetrabenazine, α-HTBZ and (β-HBZ) as well as the corresponding O-desmethyl metabolites of α-HTBZ and β-HTBZ. Subjects received a single oral dose of 25 mg of $d_6$-tetrabenazine or tetrabenazine after an overnight fast, as a powder in capsule, in Period 1 and following washout of at least 7 days. Patients were crossed over to receive the other treatment in Period 2. In each period, plasma samples were collected over 72 hours post-dose.

The in vivo metabolism of α-HTBZ and β-HTBZ was significantly attenuated following $d_6$-tetrabenazine administration, resulting in a more than doubling of the systemic exposure to total (α+β)-HTBZ when compared to exposure following tetrabenazine administration. Pharmacokinetic results are shown below in Table 37 and FIG. 3, results are presented as Mean (% CV) for $C_{max}$, AUC and $t_{1/2}$ ($AUC_{last}$ presented for parent drug as $AUC_{inf}$ not calculable), and as Mean (range) for Tmax. The increased exposure was principally attributable to increases in half-life and was associated with proportional reductions in O-desmethyl metabolites of HTBZ.

TABLE 37

Summary of Pharmacokinetic Parameters after Single Oral Dose of $d_6$-Tetrabenazine 25 mg or Tetrabenazine 25 mg

| Parameter | $d_6$-Tetraben-azine | Tetraben-azine | $d_6$-(α + β)-HTBZ | (α + β)-HTBZ |
|---|---|---|---|---|
| $C_{max}$ (ng/mL) | 0.327 (85.3) | 0.314 (111.0) | 74.6 (37.1) | 61.6 (38.2) |
| $T_{max}$ (hr) | 0.67 (0.33-1.50) [a] | 0.67 (0.33-2.00) [b] | 1.50 (0.67-2.00) | 1.00 (0.67-2.50) |
| $AUC_{inf}$ (ng hr/mL) | 0.30 (101.9) | 0.26 (168.2) | 542 (53.8) | 261 (69.6) |
| $t_{1/2}$ (hr) | N.C. | N.C. | 8.62 (38.2) | 4.82 (50.8) |

| Parameter | $d_6$-α-HTBZ | α-HTBZ | $d_6$-β-HTBZ | β-HTBZ |
|---|---|---|---|---|
| $C_{max}$ (ng/mL) | 46.1 (30.4) | 41.2 (36.0) | 29.6 (49.4) | 20.5 (51.5) |
| $T_{max}$ (hr) | 1.5 (0.67-2.52) | 1.00 (0.67-2.00) | 1.50 (0.67-2.50) | 1.00 (0.67-2.50) |
| $AUC_{inf}$ (ng hr/mL) | 373 (39.3) | 189 (59.2) | 171 (94.0) | 74.0 (99.5) |
| $t_{1/2}$ (hr) | 8.97 (34.7) | 5.47 (51.4) | 5.00 (79.7) | 2.95 (57.2) |

| Parameter | $d_3$-9-O-desmethyl-α-HTBZ[e] | 9-O-desmethyl-α-HTBZ[f] | $d_3$-9-O-desmethyl-β-HTBZ[e] | 9-O-desmethyl-β-HTBZ[f] |
|---|---|---|---|---|
| $C_{max}$ (ng/mL) | 2.15 (52.5) | 5.05 (38.6) | 6.29 (31.7) | 15.7 (27.3) |
| $T_{max}$ (hr) | 3.02 (1.50-16.0) | 2.00 (0.67-4.00) | 1.75 (0.67-8.02) | 1.75 (0.67-4.00) |
| $AUC_{last}$ (ng hr/mL) | 21.0 (37.2) | 42.5 (47.1) | 92.4 (29.6) | 205 (32.6) |
| $AUC_{inf}$ (ng hr/mL) | N.C. | 49.9 (59.8) [c] | 114 (24.6) [d] | 220 (31) |
| $t_{1/2}$ (hr) | N.C. | 6.95 (47.1) [c] | 16.9 (31.4) [d] | 16.2 (22.9) |

| Parameter | $d_3$-10-ODM-β-HTBZ[e] | 10-ODM-β-HTBZ[f] |
|---|---|---|
| $C_{max}$ (ng/mL) | 0.59 (73.9) | 1.63 (37.2) |
| $T_{max}$ | 1.50 | 1.25 |

TABLE 37-continued

Summary of Pharmacokinetic Parameters after Single Oral
Dose of d$_6$-Tetrabenazine 25 mg or Tetrabenazine 25 mg

| (hr) | (1.00-2.00) [c] | (0.67-2.90) |
|---|---|---|
| AUC$_{last}$ | 0.7 | 3.0 |
| (ng hr/mL) | (111) | (46.3) |
| AUC$_{inf}$ | N.C. | N.C. |
| (ng hr/mL) | | |
| t$_{1/2}$ (hr) | N.C. | N.C. |

[a] n = 18
[b] n = 15
[c] n = 8
[d] n = 12
[e] Test article: d$_6$-Tetrabenazine
[f] Test article: Tetrabenazine
N.C. = not calculable Relative Bioavailability of Deuterated and Non-Deuterated Metabolites.

The effect of deuteration on key pharmacokinetic parameters was evaluated by comparing d$_6$-tetrabenazine (test) to tetrabenazine (reference) using an analysis of variance (ANOVA) model for a two-period crossover including factors Sequence, Treatment, Period and Subject. Pharmacokinetic parameters were log-transformed before analysis. Point estimates and 2 one-sided 95% confidence limits (CL) were constructed and then back-transformed. The estimate of the effect of deuteration on these parameters for α-HTBZ, β-HTBZ and total (α+β)-HTBZ is shown in Table 38.

TABLE 38

Ratio of Mean Pharmacokinetic Parameters After Single Oral
Dose of d$_6$-Tetrabenazine 25 mg or Tetrabenazine 25 mg

| Analyte | Parameter | Ratio of LS Means (%) | Lower 95% CL (%) | Upper 95% CL (%) |
|---|---|---|---|---|
| α-HTBZ | C$_{max}$ (ng/mL) | 113.7 | 100.0 | 129.3 |
| | AUC$_{last}$ (hr*ng/mL) | 214.8 | 195.1 | 236.7 |
| | AUC$_{inf}$ (hr*ng/mL) | 213.6 | 194.0 | 235.0 |
| | t$_{1/2}$ (hr) | 174.7 | 156.5 | 195.0 |
| β-HTBZ | C$_{max}$ (ng/mL) | 145.8 | 126.2 | 168.5 |
| | AUC$_{last}$ (hr*ng/mL) | 240.1 | 219.9 | 262.2 |
| | AUC$_{inf}$ (hr*ng/mL) | 235.8 | 216.7 | 256.5 |
| | t$_{1/2}$ (hr) | 153.0 | 138.3 | 169.3 |
| Total (α + β)- HTBZ | C$_{max}$ (ng/mL) | 121.7 | 106.3 | 139.2 |
| | AUC$_{last}$ (hr*ng/mL) | 222.5 | 206.0 | 240.3 |
| | AUC$_{inf}$ (hr*ng/mL) | 222.2 | 205.9 | 239.7 |
| | t$_{1/2}$ (hr) | 188.0 | 167.4 | 211.1 |

Extended Release Formulations

Figure 3:
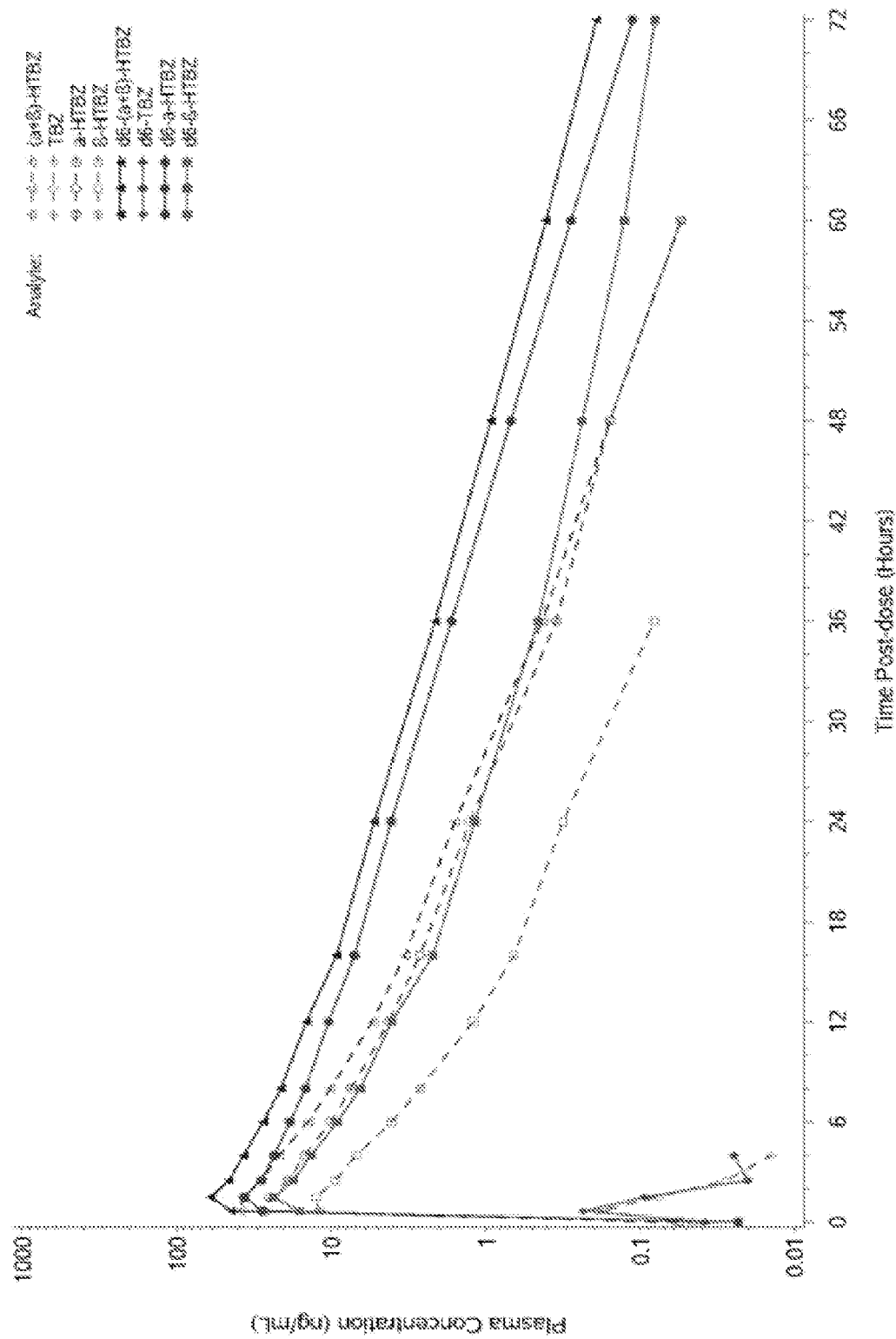
FIG. 3: Results of pharmacokinetic study of immediate-release d$_6$-tetrabenazine and its metabolites d$_6$-α-HTBZ and d$_6$-β-HTBZ compared to non-deuterated equivalents (tetrabenazine, α-HTBZ and β-HBZ) as well as the corresponding O-desmethyl metabolites.
Figure 4:
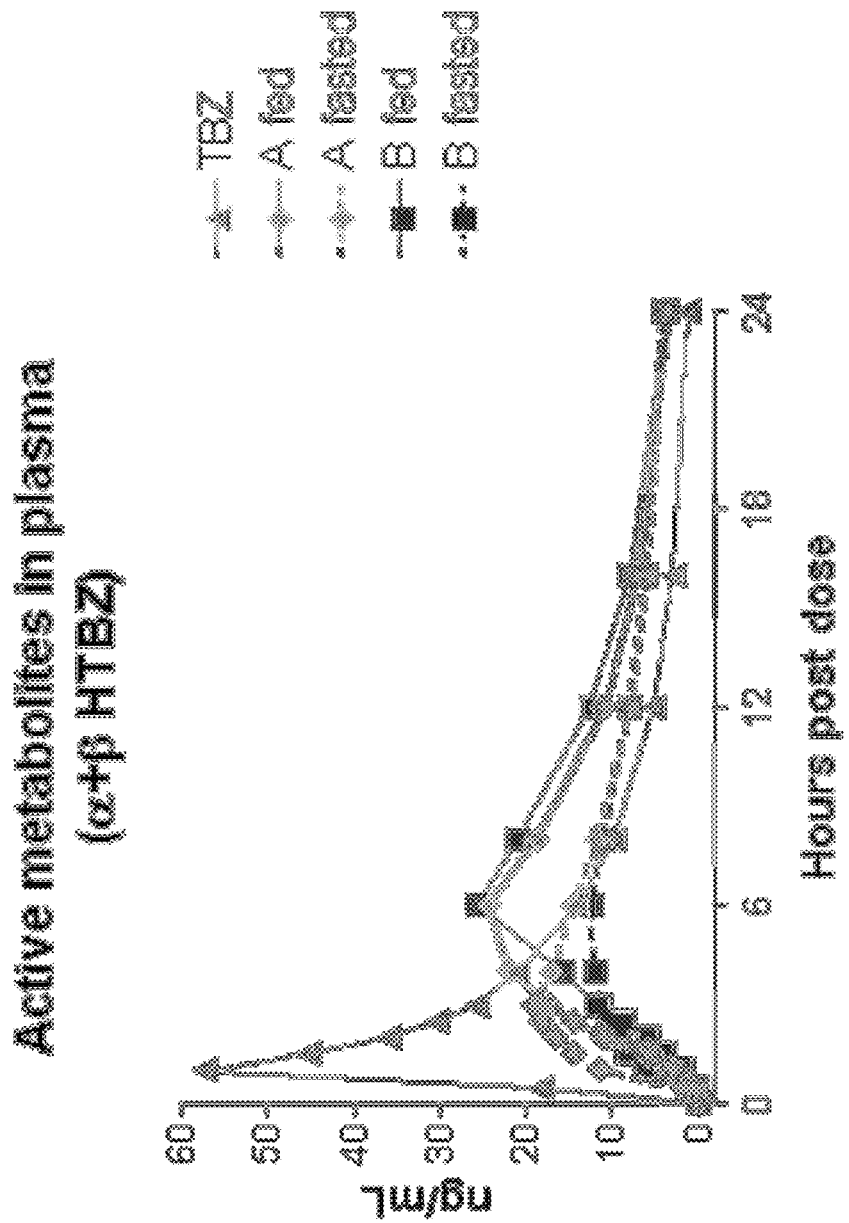
FIG. 4: Mean plasma concentrations of total (α+β)-HTBZ in each of a TBZ-fasted group, a Formulation A fed group, a Formulation B fed group, a Formulation A fasted group, and a Formulation B fasted group.
Figure 5:
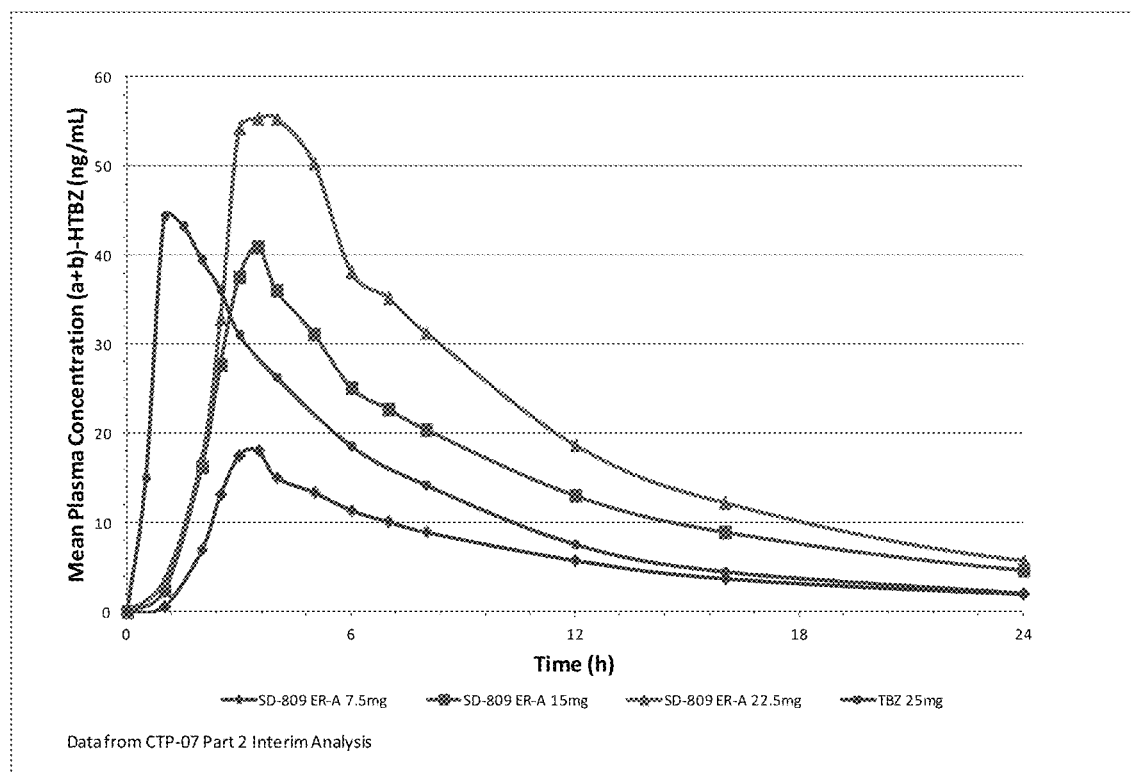
FIG. 5: Single dose mean plasma concentrations of total (α+β)-HTBZ from 3 dose levels of d$_6$-tetrabenazine ER and one dose level of tetrabenazine.
Figure 6:
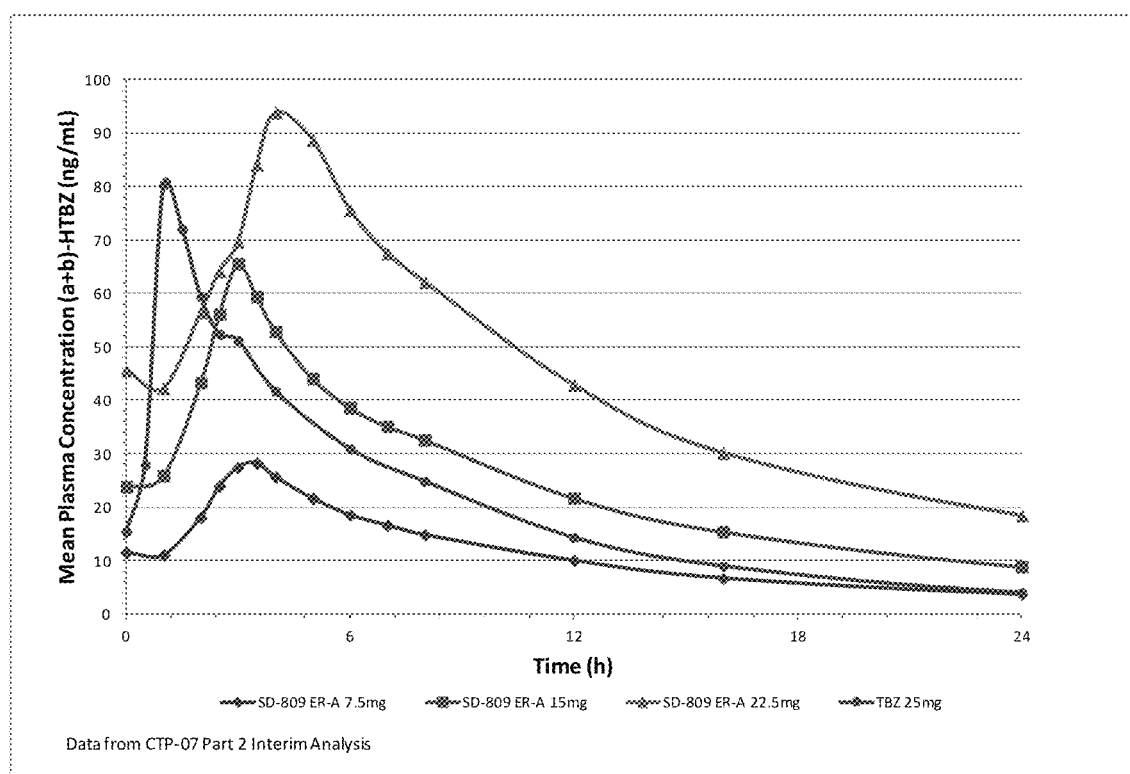
FIG. 6: Steady state plasma concentrations of total (α+β)-HTBZ from 3 dose levels of d$_6$-tetrabenazine ER and one dose level of tetrabenazine.

A Phase 1 randomized, open, 5-way crossover study was conducted in healthy CYP2D6 extensive metabolizers (EMs) and intermediate metabolizers (IMs). Subjects (n=24 total) were administered a single dose of either Formulation A (15 mg d$_6$-tetrabenazine in a round tablet, 350 mg), Formulation B (15 mg d$_6$-tetrabenazine in an oval tablet, 700 mg), or tetrabenazine (25 mg in an immediate release tablet). Administration was either in a fasted state (at least 10 hours) or in a fed state (post-high-fat and high-calorie meal/breakfast following a fast of at least 10 hours). Blood samples for measurements of plasma analytes including total (α+β)-HTBZ were taken at periodic intervals up to 24 hours post dose. Results are shown in FIG. 3 and below in Table 39, showing pharmacokinetic parameters for d$_6$-Total (α+β)-HTBZ or Total HTBZ. In vitro, Formulation A released a substantial portion of d$_6$-tetrabenazine by approximately 4 hours; Formulation B released a substantial portion d$_6$-tetrabenazine by approximately 8 hours. In each cell, the top value is the mean, the middle value is the standard deviation, and the bottom is the percentage interpatient variability (% CV).

TABLE 39

Pharmacokinetic Parameters After Single Oral Dose of d$_6$-Tetrabenazine Extended Release Formulations or Tetrabenazine 25 mg

| | A - Fasted 15 mg | B - Fasted 15 mg | A - Fed 15 mg | B - Fed 15 mg | TBZ - Fasted 25 mg |
|---|---|---|---|---|---|
| C$_{max}$ (ng/mL) | 22.52 | 14.49 | 33.32 | 28.72 | 65.14 |
| | (8.18) | (6.02) | (11.09) | (11.33) | (21.25) |
| | 36.3 | 41.6 | 33.3 | 39.5 | 32.6 |
| T$_{max}$ (hr) | 2.65 | 4.21 | 4.79 | 6.27 | 1.13 |
| | (1.85) | (2.84) | (1.70) | (1.94) | (0.37) |
| | 69.9 | 67.4 | 35.5 | 30.9 | 32.8 |
| T$_{half}$ (hr) | 9.35 | 10.03 | 6.99 | 6.98 | 4.46 |
| | (2.25) | (1.61) | (1.59) | (1.33) | (2.53) |
| | 24.1 | 16.0 | 22.7 | 19.1 | 56.7 |
| AUC$_t$ (hr*ng/mL) | 262.3 | 241.9 | 295.1 | 305.6 | 251.0 |
| | (119.4) | (118.5) | (139.3) | (143.8) | (172.8) |
| | 45.5 | 49.0 | 47.2 | 47.1 | 68.9 |
| AUC$_{inf}$ (hr*ng/mL) | 272.7 | 258.7 | 304.1 | 314.5 | 257.0 |
| | (122.0) | (122.3) | (140.9) | (145.5) | (177.0) |
| | 44.7 | 47.3 | 46.3 | 46.3 | 68.9 |

Relative Bioavailability of Deuterated and Non-Deuterated Metabolites.

In an additional analysis, an analysis of variance was conducted to compare the relative pharmacokinetic properties of the extended-release formulations A and B administered in either a fasted or fed state. Administration of d$_6$-tetrabenazine 15 mg with either ER formulation achieved systemic exposure to total (α+β)-HTBZ that was comparable to or slightly higher than that after tetrabenazine 25 mg, but with C$_{max}$ values that were markedly lower. Half lives of the deuterated HTBZ metabolites were longer than those observed for tetrabenazine. Similar findings were observed for α-HTBZ, and β-HTBZ. The ratio of LS means (test/reference) for total HBTZ is given as a percentage below in Table 40. ND indicates no data.

TABLE 40

Pharmacokinetic Parameters After Single Oral Dose of $d_6$-Tetrabenazine Extended Release Formulations

|  | A - Fasted | A - Fed | B - Fasted | B - Fed |
|---|---|---|---|---|
| $C_{max}$ (ng/mL) | 34.4 | 51.4 | 21.7 | 43.3 |
| $AUC_t$ (hr*ng/mL) | 113.5 | ND | 102.6 | ND |
| $AUC_{inf}$ (hr*ng/mL) | 115.5 | 127.7 | 105.6 | 131.2 |
| $t_{1/2}$ (hr) | 222.7 | 167.6 | 240.4 | 168.8 |

An additional Phase 1 study was conducted in healthy CYP2D6 extensive metabolizers (EMs) and intermediate metabolizers (IMs). Subjects (n=30 total) were administered a single dose of Formulation A (6, 12, 18, or 24 mg $d_6$-tetrabenazine in a round tablet. Administration was either in a fed state (post-standard or high-fat meal). Blood samples for measurements of plasma analytes including total (α+β)-HTBZ were taken at periodic intervals up to 24 hours post dose. Results are shown below in Table 41, showing pharmacokinetic parameters for $d_6$-Total (α+β)-HTBZ or Total HTBZ. In each cell, the top value is the mean, the middle value is the standard deviation, and the bottom is the percentage interpatient variability (% CV).

TABLE 41

Pharmacokinetic Parameters After Single Oral Dose of $d_6$-Tetrabenazine Extended Release Formulation

|  | 6 mg - Standard Meal | 12 mg - Standard Meal | 18 mg - Standard Meal | 24 mg - Standard Meal | 18 mg - High-fat Meal |
|---|---|---|---|---|---|
| $C_{max}$ (ng/mL) | 15.5 (3.5) 22 | 32.1 (8.1) 25 | 47.8 (12.0) 25 | 60.9 (13.8) 23 | 49.0 (8.1) 17 |
| $T_{max}$ (hr) | 3.74 (0.99) 26 | 3.90 (1.27) 33 | 3.63 (0.85) 23 | 3.92 (1.19) 30 | 4.09 (1.25) 30 |
| $T_{half}$ (hr) | 8.64 (1.84) 21 | 9.79 (2.45) 25 | 10.2 (3.3) 33 | 10.4 (2.4) 23 | 10.2 (2.5) 24 |
| $AUC_t$ (hr*ng/mL) | 122 (46) 38 | 279 (114) 41 | 407 (163) 40 | 569 (225) 40 | 425 (127) 30 |
| $AUC_{inf}$ (hr*ng/mL) | 132 (47) 35 | 289 (115) 40 | 419 (165) 39 | 580 (229) 39 | 436 (129) 30 |

Steady-State Pharmacokinetics

An open-label single and multiple ascending dose study of $d_6$-tetrabenazine ER in comparison to tetrabenazine was performed. Subjects (n=12) were administered either $d_6$-tetrabenazine ER at dosage levels of 7.5 mg, 15 mg, and 22.5 mg, or tetrabenazine (25 mg in an immediate release tablet). Administration was by a single dose or repeated doses up to 3 days twice daily. Blood samples for measurements of plasma total (α+β)-HTBZ were taken at periodic intervals up to 24 hours post dose. Single dose results are shown in FIG. 3 and below in Table 42, showing pharmacokinetic parameters for $d_6$-Total (α+β)-HTBZ or Total HTBZ. In each cell, the top value is the mean, the middle value is the standard deviation, and the bottom is the percentage interpatient variability (% CV).

TABLE 42

Pharmacokinetic Parameters After a Single Oral Dose of $d_6$-Tetrabenazine Extended Release Formulation

|  | $d_6$-Tetrabenazine ER 7.5 mg | $d_6$-Tetrabenazine ER 15 mg | $d_6$-Tetrabenazine ER 22.5 mg | TBZ - 25 mg |
|---|---|---|---|---|
| $C_{max}$ (ng/mL) | 21.37 6.78 31.7% | 45.33 8.31 18.3% | 67.49 16.72 24.8% | 55.49 21.88 39.4% |
| $T_{max}$ (hr) | 3.17 0.68 21.6% | 3.21 0.45 14.0% | 3.79 0.84 22.2% | 1.42 0.63 44.7% |
| $T_{half}$ (hr) | 7.18 1.35 18.8% | 7.66 1.36 17.7% | 8.38 2.17 22.0% | 5.60 1.98 35.3% |
| $AUC_{(0-12)}$ (hr*ng/mL) | 110.2 32.1 29.2% | 250.4 64.0 25.6% | 370 123.7 33.4% | 247.0 136.3 55.2% |
| $AUC_{inf}$ (hr*ng/mL) | 176.2 69.3 39.4% | 408.3 147.2 36.1% | 610 291 47.0% | 322.0 220.8 68.6% |

Steady-state dosing results are shown in FIG. 3 and below in Table 43, showing pharmacokinetic parameters for $d_6$-Total (α+β)-HTBZ or Total HTBZ. In each cell, the top value is the mean, the middle value is the standard deviation, and the bottom is the percentage interpatient variability (% CV).

TABLE 43

Pharmacokinetic Parameters After Multiple Oral Doses of $d_6$-Tetrabenazine Extended Release Formulation

|  | $d_6$-Tetrabenazine ER 7.5 mg | $d_6$-Tetrabenazine ER 15 mg | $d_6$-Tetrabenazine ER 22.5 mg | TBZ - 25 mg |
|---|---|---|---|---|
| $C_{max}$ (ng/mL) | 31.5 8.16 26% | 72.0 14.5 21% | 111.0 47.2 43% | 94.9 29.16 31% |
| $T_{max}$ (hr) | 3.17 0.49 16% | 2.78 0.41 15% | 3.75 0.79 21% | 1.34 0.62 46% |
| $T_{half}$ (hr) | 8.8 1.97 22% | 9.06 2.53 28% | 9.50 2.32 21% | 6.30 1.97 31.2% |
| $AUC_{(0-12)}$ (hr*ng/mL) | 203 69.2 34% | 443 125.8 28% | 769 357 46% | 415.8 237.9 57.2% |

Polymorphs

Example 37

$d_6$-Tetrabenazine Form I $d_6$-Tetrabenazine was dissolved in 3 volumes of ethanol, then the mixture was heated until the solid was dissolved. The solution was stirred and cooled to room temperature at the rate of 20° C./h. Then the mixture was stirred at 0° C. for 1 h. The precipitated solid was isolated by filtration and dried under to give $d_6$-tetrabenazine, Form I. Characteristic X-ray powder diffraction peaks are shown in Table 44 and FIG. 9.

TABLE 44

| Pos. [°2Th.] | d-spacing | Rel. Int. [%] |
|---|---|---|
| 8.2971 | 10.65669 | 100.00 |
| 9.7596 | 9.06279 | 1.08 |
| 11.5878 | 7.63674 | 2.51 |

TABLE 44-continued

| Pos. [°2Th.] | d-spacing | Rel. Int. [%] |
|---|---|---|
| 11.9854 | 7.38428 | 1.40 |
| 13.9395 | 6.35319 | 2.20 |
| 16.8229 | 5.27022 | 0.39 |
| 17.7086 | 5.00859 | 0.65 |
| 20.0394 | 4.43099 | 2.70 |
| 20.6309 | 4.30526 | 0.65 |
| 22.0276 | 4.03532 | 1.57 |
| 22.9053 | 3.88265 | 0.84 |
| 23.3083 | 3.81642 | 0.74 |
| 23.6760 | 3.75798 | 2.83 |
| 24.4118 | 3.64636 | 1.01 |
| 27.4839 | 3.24535 | 0.36 |
| 33.5077 | 2.67442 | 1.24 |
| 39.6425 | 2.27355 | 0.29 |
| 42.2841 | 2.13743 | 1.37 |
| 43.8696 | 2.06210 | 0.25 |

A sample of $d_6$-tetrabenazine Form I was analyzed by thermogravimetric analysis. The results are shown in FIG. 7. A sample of $d_6$-tetrabenazine Form I was analyzed by differential scanning calorimetry. The results are shown in FIG. 8.

Example 38

$d_6$-Tetrabenazine Form II $d_6$-Tetrabenazine was dissolved in methanol and precipitated by slow evaporation at ambient temperature and humidity to give $d_6$-tetrabenazine, Form II. Characteristic X-ray powder diffraction peaks are shown in Table 45 and FIG. 12.

TABLE 45

| Pos. [°2Th.] | d-spacing | Rel. Int. [%] |
|---|---|---|
| 8.2971 | 10.65669 | 100.00 |
| 9.7596 | 9.06279 | 1.08 |
| 11.5878 | 7.63674 | 2.51 |
| 11.9854 | 7.38428 | 1.40 |
| 13.9395 | 6.35319 | 2.20 |
| 16.8229 | 5.27022 | 0.39 |
| 17.7086 | 5.00859 | 0.65 |
| 20.0394 | 4.43099 | 2.70 |
| 20.6309 | 4.30526 | 0.65 |
| 22.0276 | 4.03532 | 1.57 |
| 22.9053 | 3.88265 | 0.84 |
| 23.3083 | 3.81642 | 0.74 |
| 23.6760 | 3.75798 | 2.83 |
| 24.4118 | 3.64636 | 1.01 |
| 27.4839 | 3.24535 | 0.36 |
| 33.5077 | 2.67442 | 1.24 |
| 39.6425 | 2.27355 | 0.29 |
| 42.2841 | 2.13743 | 1.37 |
| 43.8696 | 2.06210 | 0.25 |

A sample of $d_6$-tetrabenazine Form II was analyzed by thermogravimetric analysis. The results are shown in FIG. 10. A sample of $d_6$-tetrabenazine Form II was analyzed by differential scanning calorimetry. The results are shown in FIG. 11.

From the foregoing description, one skilled in the art can ascertain the essential characteristics of this invention, and without departing from the spirit and scope thereof, can make various changes and modifications of the invention to adapt it to various usages and conditions.

What is claimed is:

1. A pharmaceutical composition comprising, in a solid dosage form for oral delivery of between about 100 mg and about 1 g total weight:
between about 2% and about 18% of a mixture of compounds of structural Formula I

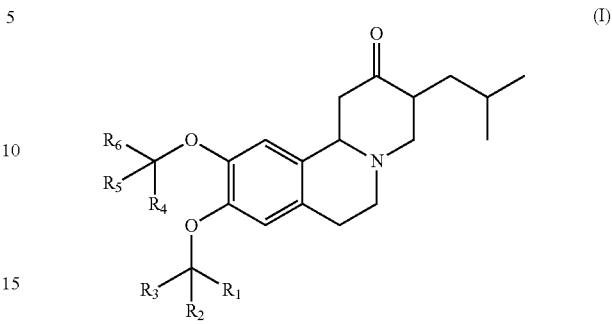

or a salt thereof, wherein:
$R_1$-$R_6$ are independently selected from the group consisting of hydrogen and deuterium, and the composition has deuterium enrichment of at least 10% in the compounds of Formula I;
between about 60% and about 70% mannitol;
between about 15% and about 25% microcrystalline cellulose;
between about 1% and about 10% of a polyvinylpyrrolidone;
between about 0.5% and about 2% of a polysorbate;
between about 5% and about 20% of a poly(ethylene oxide) polymer; and
between about 0.5% and about 2% of magnesium stearate.

2. The pharmaceutical composition as recited in claim 1 wherein said polyvinylpyrrolidone has an average molecular weight of about 58,000 and a K-value of 29 to 32.

3. The pharmaceutical composition as recited in claim 1 wherein said polysorbate is polyoxyethylene (20) sorbitan monooleate.

4. The pharmaceutical composition as recited in claim 1 wherein said poly(ethylene oxide) polymer is poly(ethylene) oxide polymer PEG-45M.

5. The pharmaceutical composition as recited in claim 1 further comprising an anti-oxidant.

6. The pharmaceutical composition as recited in claim 5 wherein said anti-oxidant is selected from the group consisting of butylated hydroxyanisole and butylated hydroxytoluene.

7. The pharmaceutical composition as recited in claim 1 further comprising an aqueous film coating.

8. The pharmaceutical composition as recited in claim 7 wherein said aqueous film coating comprises polyvinyl alcohol, titanium dioxide, polyethylene glycol, talc, and a FD&C color additive.

9. The pharmaceutical composition as recited in claim 1 wherein the total weight is about 350 mg.

10. The pharmaceutical composition as recited in claim 1 comprising from about 5 mg to about 30 mg of said mixture of compounds of structural Formula I.

11. The pharmaceutical composition as recited in claim 10 comprising about 6 mg of said mixture of compounds of structural Formula I.

12. The pharmaceutical composition as recited in claim 10 comprising about 12 mg of said mixture of compounds of structural Formula I.

13. The pharmaceutical composition as recited in claim 10 comprising about 15 mg of said mixture of compounds of structural Formula I.

14. The pharmaceutical composition as recited in claim 10 comprising about 18 mg of said mixture of compounds of structural Formula I.

15. The pharmaceutical composition as recited in claim 1 comprising, in a solid dosage form for oral delivery of about 350 mg total weight:
- about 15 milligrams of said mixture of compounds of structural Formula I;
- about 62.0% mannitol;
- about 17.7% microcrystalline cellulose;
- about 4.0% of polyvinylpyrrolidine having an average molecular weight of about 58,000 and a K-value of 29 to 32;
- about 1.1% of polyoxyethylene (20) sorbitan monooleate;
- about 10.0% of poly(ethylene) oxide polymer PEG-45M; and
- about 1.0% of magnesium stearate.

16. The pharmaceutical composition as recited in claim 15 further comprising an anti-oxidant selected from the group consisting of butylated hydroxyanisole and butylated hydroxytoluene.

17. The pharmaceutical composition as recited in claim 16 further comprising an aqueous film coating.

18. The pharmaceutical composition as recited in claim 17 wherein said aqueous film coating comprises polyvinyl alcohol, titanium dioxide, polyethylene glycol, talc, and a FD&C color additive.

19. The pharmaceutical composition as recited in claim 1 comprising, in a solid dosage form for oral delivery of about 350 mg total weight:
- about 6 milligrams of said mixture of compounds of structural Formula I;
- about 63.6% mannitol;
- about 18.3% microcrystalline cellulose;
- about 4.0% of polyvinylpyrrolidine having an average molecular weight of about 58,000 and a K-value of 29 to 32;
- about 1.1% of polyoxyethylene (20) sorbitan monooleate;
- about 10.0% of poly(ethylene) oxide polymer PEG-45M;
- about 1.0% of magnesium stearate;
- about 0.1% of butylated hydroxyanisole; and
- about 0.1% of butylated hydroxytoluene.

20. The pharmaceutical composition as recited in claim 19 further comprising an aqueous film coating.

21. The pharmaceutical composition as recited in claim 20 wherein said aqueous film coating comprises polyvinyl alcohol, titanium dioxide, polyethylene glycol, talc, and a FD&C color additive.

22. The pharmaceutical composition as recited in claim 1 comprising, in a solid dosage form for oral delivery of about 350 mg total weight:
- about 12 milligrams of said mixture of compounds of structural Formula I;
- about 62.3% mannitol;
- about 17.9% microcrystalline cellulose;
- about 4.0% of polyvinylpyrrolidine having an average molecular weight of about 58,000 and a K-value of 29 to 32;
- about 1.1% of polyoxyethylene (20) sorbitan monooleate;
- about 10.0% of poly(ethylene) oxide polymer PEG-45M;
- about 1.0% of magnesium stearate;
- about 0.1% of butylated hydroxyanisole; and
- about 0.1% of butylated hydroxytoluene.

23. The pharmaceutical composition as recited in claim 22 further comprising an aqueous film coating.

24. The pharmaceutical composition as recited in claim 23 wherein said aqueous film coating comprises polyvinyl alcohol, titanium dioxide, polyethylene glycol, talc, and a FD&C color additive.

25. The pharmaceutical composition as recited in claim 1 comprising, in a solid dosage form for oral delivery of about 350 mg total weight:
- about 18 milligrams of said mixture of compounds of structural Formula I;
- about 60.5% mannitol;
- about 18.0% microcrystalline cellulose;
- about 4.0% of polyvinylpyrrolidine having an average molecular weight of about 58,000 and a K-value of 29 to 32;
- about 1.1% of polyoxyethylene (20) sorbitan monooleate;
- about 10.0% of poly(ethylene) oxide polymer PEG-45M;
- about 1.0% of magnesium stearate;
- about 0.1% of butylated hydroxyanisole; and
- about 0.1% of butylated hydroxytoluene.

26. The pharmaceutical composition as recited in claim 25 further comprising an aqueous film coating.

27. The pharmaceutical composition as recited in claim 26 wherein said aqueous film coating comprises polyvinyl alcohol, titanium dioxide, polyethylene glycol, talc, and a FD&C color additive.

* * * * *